US009149564B2

(12) United States Patent
Jin et al.

(10) Patent No.: US 9,149,564 B2
(45) Date of Patent: Oct. 6, 2015

(54) ARTICLES COMPRISING LARGE-SURFACE-AREA BIO-COMPATIBLE MATERIALS AND METHODS FOR MAKING AND USING THEM

(75) Inventors: Sungho Jin, San Diego, CA (US); Seunghan Oh, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1508 days.

(21) Appl. No.: 12/305,887

(22) PCT Filed: Jun. 22, 2007

(86) PCT No.: PCT/US2007/071947
§ 371 (c)(1), (2), (4) Date: Aug. 9, 2010

(87) PCT Pub. No.: WO2008/066965
PCT Pub. Date: Jun. 5, 2008

(65) Prior Publication Data

US 2010/0303722 A1 Dec. 2, 2010

Related U.S. Application Data

(60) Provisional application No. 60/816,221, filed on Jun. 23, 2006.

(51) Int. Cl.
*A61K 49/00* (2006.01)
*A01N 63/00* (2006.01)
(Continued)

(52) U.S. Cl.
CPC ................ *A61L 27/54* (2013.01); *A61L 27/30* (2013.01); *A61L 27/3839* (2013.01);
(Continued)

(58) Field of Classification Search
None
See application file for complete search history.

(56) References Cited

U.S. PATENT DOCUMENTS 4,604,847 A 8/1986 Moulding, Jr. et al.
5,989,027 A * 11/1999 Wagner et al. ................ 433/173
(Continued)

FOREIGN PATENT DOCUMENTS

GB 2 184 458 * 6/1987 ............ C25D 17/12
WO WO 2005/025630 * 3/2005 ............. A61L 27/18
WO WO-2005/065282 7/2005
WO WO-2006/116752 11/2006

OTHER PUBLICATIONS

Roszek et al.; "Nanotechnology in medical applications: state-of-the-art in materials and devices"; RIVM report 265001001; 2005; p. 67 of 123.*
(Continued)

*Primary Examiner* — Jeffrey T Palenik
(74) *Attorney, Agent, or Firm* — Gregory P. Einhorn; Greer, Burns & Crain, Ltd.

(57) ABSTRACT

The present invention provides articles of manufacture comprising biocompatible nanostructures comprising significantly increased surface area for, e.g., organ, tissue and/or cell growth, e.g., for bone, tooth, kidney or liver growth, and uses thereof, e.g., for in vitro testing of drugs, chemicals or toxins, or as in vivo implants, including their use in making and using artificial tissues and organs, and related, diagnostic, screening, research and development and therapeutic uses, e.g., as drug delivery devices. The present invention provides biocompatible nanostructures with significantly increased surface area, such as with nanotube and nanopore array on the surface of metallic, ceramic, or polymer materials for enhanced cell and bone growth, for in vitro and in vivo testing, cleansing reaction, implants and therapeutics. The present invention provides optically transparent or translucent cell-culturing substrates. The present invention provides biocompatible and cell-growth-enhancing culture substrates comprising elastically compliant protruding nanostructure substrates coated with Ti, $TiO_2$ or related metal and metal oxide films.

34 Claims, 41 Drawing Sheets

(51) Int. Cl.
*A61F 2/00* (2006.01)
*A61L 27/54* (2006.01)
*A61L 27/30* (2006.01)
*A61L 27/38* (2006.01)

(52) U.S. Cl.
CPC ..... *A61L 2300/254* (2013.01); *A61L 2300/256* (2013.01); *A61L 2300/258* (2013.01); *A61L 2300/406* (2013.01); *A61L 2300/414* (2013.01); *A61L 2300/43* (2013.01); *A61L 2300/624* (2013.01)

(56) References Cited

U.S. PATENT DOCUMENTS

| | | | | |
|---|---|---|---|---|
| 7,235,295 | B2 * | 6/2007 | Laurencin et al. | 428/364 |
| 2004/0206448 | A1 * | 10/2004 | Dubrow | 156/276 |
| 2006/0229715 | A1 | 10/2006 | Istephanous et al. | |

OTHER PUBLICATIONS

Ghicov et al., Electrochemistry Communications (2005) 7:505-509.
Gong et al., Journal of Materials Research (2001) 16(12):3331-3334.
International Preliminary Report on Patentability for PCT/US2007/071947, issued on Jan. 6, 2009, 7 pages.
International Search Report for PCT/US2007/071947, mailed on Sep. 25, 2008, 3 pages.
Lakshmi et al., Chemistry of Materials (1997) 9:2544-2550.
Macak et al., Angew Chem Int Ed (2005) 44:2100-2102.
Macak et al., Angew Chem Int Ed (2005) 44:7463-7465.
Macak et al., Electrochimica Acta (2005) 50:3679-3684.
Meng et al., Thin Solid Films (1993) 226:22.
Miao et al., Nano Letters (2002) 2(7):717-720.
Oh et al., Biomaterials (2005) 26:4938-4943.
Oh et al., Journal of Biomedical Materials Research (2006) 78A:97-103.
Pankhurst et al., Journal of Physics D: Appl Phys (2003) 36:R167-R181.
Robbie et al., J Vacuum Science & Technology (1995) 13(3):1032.
Rodriguez et al., Adv Mater (2000) 12(5):341.
Tartaj et al., Journal of Physics D: Appl Phys (2003) 36:R182-R197.
Thornton, J Vac Sci Technol (1986) A4(6):3059.
Written Opinion of the International Searching Authority for PCT/US2007/071947, mailed on Sep. 25, 2008, 6 pages.
Ye et al., Adv Mater (2003) 15:316.
Ye et al., Mater Chem (2004) 14:908.

* cited by examiner

Array of protruding large-surface-area hairy, mesh-screen, or particulate shaped Ti members bonded onto Ti implant surface and processed to exhibit TiO$_2$ nanotube or nanopore surface for rapid culture of cells One detection element Bio chip substrate

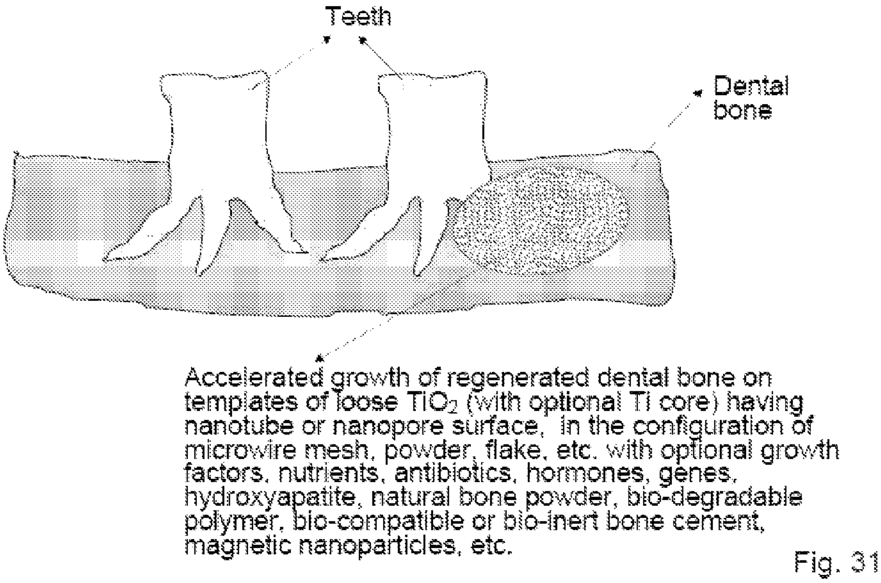

Fig. 31

Accelerated growth of regenerated dental bone on templates of loose $TiO_2$ (with optional Ti core) having nanotube or nanopore surface, in the configuration of microwire mesh, powder, flake, etc. with optional growth factors, nutrients, antibiotics, hormones, genes, hydroxyapatite, natural bone powder, bio-degradable polymer, bio-compatible or bio-inert bone cement, magnetic nanoparticles, etc.

ARTICLES COMPRISING LARGE-SURFACE-AREA BIO-COMPATIBLE MATERIALS AND METHODS FOR MAKING AND USING THEM

CROSS-REFERENCE TO RELATED APPLICATIONS

This United States utility patent application is the §371 national phase of PCT international patent application no. PCT/US2007/071947, having an international filing date of Jun. 22, 2007, which claims benefit of priority to U.S. Provisional Patent Application Ser. No. 61/816,221, filed Jun. 23, 2006. The aforementioned applications are expressly incorporated herein by reference in their entirety and for all purposes.

FIELD OF THE INVENTION

The present invention provides articles of manufacture comprising biocompatible nanostructures comprising significantly increased surface area for, e.g., organ, tissue and/or cell growth, e.g., for bone, tooth, kidney or liver growth, and uses thereof, e.g., for in vitro testing of drugs, chemicals or toxins, or as in vivo implants, including their use in making and using artificial tissues and organs, and related diagnostic, screening, research and development and therapeutic uses, e.g., as drug delivery devices. The present invention provides biocompatible nanostructures with significantly increased surface area, such as with nanotube and nanopore array on the surface of metallic, ceramic, or polymer materials for enhanced cell and bone growth, for in vitro and in vivo testing, cleansing reaction, implants and therapeutics. The present invention provides optically transparent or translucent cell-culturing substrates. The present invention provides biocompatible and cell-growth-enhancing culture substrates comprising elastically compliant protruding nanostructure substrates coated with Ti, $TiO_2$ or related metal and metal oxide films.

BACKGROUND OF THE INVENTION

It is known that the nano-scaled materials exhibit extraordinary electrical, optical, magnetic, chemical and biological properties, which cannot be achieved by micro-scaled or bulk counterparts. The development of nano-scaled materials has been intensively pursued in order to utilize such properties for various technical applications including biomedical and nano-bio applications.

Two-dimensional and three-dimensionally cultured cells are useful not only for liver cell related applications, but for producing a number of other cells in a healthy and accelerated manner. There are needs to supply or implant various types of cells including bone cells, liver cells, kidney cells, blood vessel cells, skin cells, periodontal cells, stem cells, and other human or animal organ cells.

There is a critical need for an artificial liver device that can remove toxins and improve immediate and long-term survival of patients suffering from liver disease. An artificial liver device can be useful as a temporary artificial liver for patients awaiting a liver transplant, and also provide support for post-transplantation patients until the grafted liver functions adequately to sustain the patient. One of the major roadblocks to the development of an effective artificial liver device is the lack of a satisfactory liver cell line that can provide the functions of a liver.

A fast growth and supply of cells especially rare cells, such as stem cell enrichment, can be crucial for many potential therapeutic applications as well as for enhancing the speed of advances in stem cell science and technology. In addition, fast detection and diagnosis of disease cells or possible bio-terror cells (such as epidemic diseases, anthrax or SARS) from a very small or trace quantity of available cells can be accomplished if the cell growth speed can be accelerated.

SUMMARY

The invention provides new biomaterials structures having macro-micro-nano combined features strongly bonded onto and protruding above the surface of the structure, e.g., an implant or cell-growth substrate surface of the invention. The invention also provides an alternative embodiment of large-surface-area, free-standing configuration of loose crumbled wire mesh, short fiber or loose powder configurations instead of having them bonded/attached onto a solid implant or substrates.

The invention provides compositions comprising large-surface-area, thin, macro or microscale members comprising hairy, gauge, wire, woven wire, spring, ribbon or particulate array configurations of Ti or other related metals, alloys and/or ceramics that are directly and strongly bonded onto a Ti-base or alloy-base implants or cell-growth substrates; and in one aspect, with the surface of each of the members having a high density array of titanium oxide nanotube or titanium oxide covered nanopore surface.

In alternative aspects, the thickness (or "thinness", depending on the context) of a coating on the surface of any product of manufacture of this invention (including implants, devices, etc.) can be in the range from about 1 to 100 nm, 1 to 50 nm, or about 1 to 20 nm, or in alternative embodiments: at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 or more nm. The thickness or "thinness" (both referencing the amount (or vertical dimension) of coating on a surface) can be even, or not even, over any particular portion, or all of a surface of a product of manufacture of this invention. The coating can be multi-laminar (multilayered) with one or a mixture of compounds, as described herein.

An alternative embodiment comprises loose, short-fibers or particles of Ti with a large-surface-area, high density array of titanium oxide nanotubes or titanium oxide covered nanopores.

Biomaterials of the invention can exhibit enhanced cell adhesion and accelerated cell growth characteristics as well as enhanced bone growth. In one embodiment, the thin Ti members and or in another aspect, the base Ti-base implants, can have a cell-adhesion-improving and cell-growth-accelerating surface nanostructure of $TiO_2$ nanotubes or $TiO_2$-covered nanopores with a density of at least about $0.25\times10^8/cm^2$, or in another aspect, at least about $1\times10^8/cm^2$, or at least between about $0.2\times10^8/cm^2$ to $2\times10^8/cm^2$.

In alternative aspects, the invention provides micro-nano or macro-nano combined biomaterials implants with protruding structural features above the implant surface; and in alternative embodiments these can provide advantageous characteristics for bio applications such as further improved stability, biocompatibility and mechanical lock-in reliability at the implant-cultured bone/cell interface, as well as substantially accelerated cell/bone growth accelerating characteristics due to the $TiO_2$ nanotube and related structures.

Exemplary biomaterials used to practice this invention include: (i) a surface structure with fast-growing cells or bones encircling or surrounding micro or macro members; in one aspect this provides significantly enhanced mechanical lock-in structure for improved mechanical strength on tensile or shear strain; (ii) bonded Ti members having compliant or springy structures which can accommodate strains/stresses during the early stage of bone growth to reduce a risk of catastrophic bone-implant interface failure; (iii) structures comprising micro/macro Ti members such as mesh screens, ribbons or wire arrays strongly bonded serving as on Ti implant surface, which in alternative aspects can serve as efficient, high-density structural reinforcement within the grown bone, (iv) loose configured Ti short-fibers, fragments, particles with high-density surface nanostructure of $TiO_2$ nanotubes or $TiO_2$-covered nanopores, which in alternative aspects can serve as efficient and convenient additives to bone-growth-accelerating composites or cements, for repair of orthopedic or dental bones; (v) micro-nano or macro-nano combined structures, which in alternative embodiments can comprise growth factors and/or other biological agents such as antibiotics, genes, proteins, drugs, magnetic nanoparticles added inside the nanopores or nanotubes for, e.g., further accelerated cell growth, healthy cell growth, drug release for various therapeutic uses; (vi) the added micro or macro Ti members with large surface area, which in alternative aspects allows easier growth of three-dimensional cell, organ or bone structures; (vii) biocompatible $TiO_2$-nanotube type, $TiO_2$-nanofiber type or $TiO_2$-nanopore type surfaces, which in alternative aspects can also be applied onto the surface of other non-Ti-based implants of metallic, ceramic, semiconductor, or polymer materials by thick film coating followed by anodization and optional crystallization heat treatment.

These structures of the invention can be useful for rapid production of healthy cells including liver cells, bone cells, kidney cells, blood vessel cells, skin cells, periodontal cells, stem cells and other rare cells, as well as rapid formation/growth of strongly adherent bones. In one aspect, structures the invention can be useful for reliable and faster orthopedic or dental bone repair, for preparation of partial or full implant organs for in vivo insertion, or ex vivo operation as an artificial liver or kidney, for externally controllable drug release and therapeutic treatments, for efficient toxicity testing of drugs and chemicals, and for diagnosis/detection of disease or forensic cells.

The invention also provides various methods of manufacture, methods of cell culturing, method of implant applications using the inventive, cell/bone-growth accelerating biomaterials of this invention.

The invention also provides products of manufacture, e.g., as drug delivery devices, comprising a biocompatible surface comprising (a) a least a portion of its surface area comprising (i) thin, macro or microscale members comprising hairy, gauge, wire, woven wire, spring, ribbon, powder or particulate array configurations, or comprising a Ti or other related metal material, an alloy and/or a ceramic; (ii) loose, short-fibers or particles of Ti; (iii) micro-wires or micro-ribbons; (iv) spring-like fiber or mesh screen shapes comprising a Ti or other related metal material, an alloy and/or a ceramic; or (v) structures as illustrated in FIGS. 1, 2, 5, 6, 7, 8, 9, 10, 11, 12, 13, 14, 15 and/or 16; and, (b) (i) a biocompatible vertically aligned nanotube array structure on a biocompatible substrate comprising a laterally separated nanotube arrangement; (ii) a lock-in nanostructure comprising a plurality of nanopores or nanotubes, wherein the nanopore or nanotube entrance has a smaller diameter or size than the rest (the interior) of the nanopore or nanotube to exhibit a re-entrant configuration; (iii) a dual structured biomaterial comprising (A) micro- or macro-pores, wherein the micro or macro pores has an average diameter, or equivalent diameter if the pores are not circular, in the range of between about 0.5-1,000 μm, or between about 1-100 μm, and optionally the entrances of the micro or macro pores have a smaller diameter or size than the rest (the interior) of the micro or macro pores; and, (B) a surface area covered with nanotubes, optionally $TiO_2$ nanotubes, having an average pore diameter in the range of between about 30-600 nm; (iv) a biomaterial having a surface comprising a plurality of enlarged diameter nanopores and/or nanotubes, wherein the nanopores and/or nanotubes comprise at least 150 nm, or optionally at least 200 nm, or at least 400 nm; (v) an array comprising a solid substrate and a plurality of vertically aligned, laterally spaced, nanotubes associated with the substrate, wherein each nanotube comprises a nanopore; (vii) an array comprising a solid substrate and a plurality of vertically aligned, laterally spaced, nanotubes associated with the substrate, wherein each nanotube comprises a nanopore and wherein the array comprises a cell, wherein optionally the cell is suitable for implantation, and optionally the cell is suitable for implantation and regeneration of an organ or a dental tissue in a subject; (viii) an array comprising a solid substrate and a plurality of vertically aligned, laterally spaced, nanotubes associated with the substrate, wherein each nanotube comprises a nanopore and wherein the array comprises a cells suitable for implantation and regeneration of a bone and/or a joint tissue in a subject; (ix) an array comprising a solid substrate and a plurality of vertically aligned, laterally spaced, nanotubes associated with the substrate, wherein each nanotube comprises a nanopore and wherein the array comprises one or more biologically active agents selected from the group consisting of therapeutic drugs, growth factors, proteins, enzymes, hormones, nucleic acids, RNA, DNA, genes, vectors, antibiotics or antibodies, small molecules, radioisotopes and magnetic nanoparticles; (x) a two or a three-dimensional array comprising (A) a solid substrate comprising Ti wires, ribbons or rods, or any combination thereof; and (B) a plurality of vertically aligned, laterally spaced, nanotubes associated with the substrate, wherein each nanotube comprises a nanopore; (xi) a product of manufacture comprising a size-randomized and shape-randomized nanopore- or nanotube-comprising surface made by a method comprising the following steps (A) providing a composition comprising a Ti or Ti oxide surface, (B) depositing a semi-wettable coating on the Ti or Ti oxide surface by employing lithographic patterning or by a thin film deposition technique, wherein the coating decomposes into nano- or micro-islands of local etch masks, and (C) chemical etching or electrochemical anodization of the etch-masked surface, thereby generating a size-randomized and shape-randomized nanopore- or nanotube-comprising surface; or (xii) a combination thereof. In one aspect of the product of manufacture, the thin, macro or microscale members and/or the nanotube array structure comprise Ti and Ti oxide, Zr, Hf, Nb, Ta, Mo, W and/or their alloys or oxides of these metals, and/or alloys; and optionally having a thickness of at least 5 nm; and optionally having a coating coverage of at least 80% of the nanotube or nanopore surfaces, wherein the matrix material comprises Ti, Zr, Hf, Nb, Ta, Mo, W, and/or their oxides, or alloys of these metals and oxides, and/or Si, Si oxide, Al, Al oxide, carbon, diamond, noble metals, Au, Ag, Pt and/or their alloys, polymer or plastic materials, or composite metals, ceramics and/or polymers.

Alternative embodiments of the products of manufacture of the invention are optically transparent or translucent cell-culturing substrates with nano imprint patterned nanostructures. In this aspect, optical transparency of a cell culture substrate is an important characteristic, as it allows a microscopic examination of the cell behavior using inverted microscope with transmitted light illumination. The surface of such a nanostructure is coated with an optically transparent or translucent, very thin film of Ti or Ti-base alloys (e.g., Ti—Al—V alloys), other refractory metals (e.g., Zr, Nb, Hf, Ta, W and their alloys), or $TiO_2$, $Nb_2O_5$, $ZrO_2$, $HfO_2$, $Ta_2O_5$, $W_2O_3$ or mixed alloy oxide. In alternative aspects, the thickness of the Ti or $TiO_2$ related coating is between about 1 to 50 nm, or between about 1 to 20 nm. The related coating can comprise (i) a Ti, Zr, Hf, Nb, Ta, Mo and/or W metal; (ii) an oxide of (i); (iii) an alloy of (i); (iv) a Si, a Si oxide, an Al, an Al oxide, a carbon, a diamond, a noble metal, an Au, an Ag, a Pt and/or an Al, Au, an Ag, a Pt alloy, a polymer or a plastic material, a composite metal, a ceramic, a polymer and/or a combination thereof.

Alternative embodiments of the products of manufacture of the invention comprise an elastically compliant nanostructure substrate coated with Ti, $TiO_2$ or related metal and metal oxide or nitride films, which can comprise (i) a Ti, Zr, Hf, Nb, Ta, Mo and/or W metal; (ii) an oxide of (i); (iii) an alloy of (i); (iv) a Si, a Si oxide, an Al, an Al oxide, a carbon, a diamond, a noble metal, an Au, an Ag, a Pt and/or an Al, Au, an Ag, a Pt alloy, a polymer or a plastic material, a composite metal, a ceramic, a polymer and/or a combination thereof. As the stress or strain that the growing/propagating cells experience has a tremendous effect on the cell growth behavior. By providing elastically soft substrate which is made even more flexible by virtue of added surface nanostructure, a further enhanced cell growth is obtained.

The invention provides products of manufacture comprising a biocompatible surface, wherein at least a portion of, or all of, the surface area of the biocompatible surface comprises or is covered or coated by structures comprising:

(A)(i) a plurality of thin, macro or microscale members in a hairy, a gauge, a wire, a woven wire, a spring, a ribbon, a powder, a flake shaped structure and/or a particulate array configuration, wherein the thin, a macro or a microscale member comprises a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic, wherein the plurality of thin, macro or microscale members are fixed or loosely placed, or a combination thereof, on the biocompatible surface;

(ii) a plurality of loose, short-fibers, or flake shaped structures, or particles of Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic, wherein optionally the fibers or particles are straight, curved and/or bent, and optionally the spring-like fibers or mesh screen shapes are fixed or loosely placed, or a combination thereof, on the biocompatible surface;

(iii) a plurality of micro-wires, micro-fibers or micro-ribbons, wherein optionally the wires, ribbons or fibers are straight, curved and/or bent, wherein optionally the micro-wires, micro-fibers or micro-ribbons are fixed or loosely placed, or a combination thereof, on the biocompatible surface;

(iv) a plurality of spring-like fibers or mesh screen shapes comprising a Ti or metal material, an alloy and/or a ceramic, wherein optionally the spring-like fibers or mesh screen shapes are fixed or loosely placed, or a combination thereof, on the biocompatible surface;

(v) a structure as illustrated in FIGS. 1, 2, 5, 6, 7, 8, 9, 10, 11, 12, 13, 14, 15 and/or 16;

(vi) any of the structures of (i) to (v) in the form of a high-surface-area wire array, a mesh screen array, a particle assembly array or a combination thereof;

(vii) any combination of the structures of (i) to (vi), and optionally wherein any combination of the structures of (i) to (vi) are fixed or loosely placed as a loose deposit, a loose powder, a loose film, a loose particle, a loose short-fiber or a loose flake, or any combination thereof, on the biocompatible surface;

and the biocompatible surface comprises structures comprising:

(B) (i) a biocompatible vertically aligned nanotube array structure on a biocompatible substrate comprising a laterally separated nanotube arrangement;

(ii) a lock-in nanostructure comprising a plurality of nanopores or nanotubes, wherein the nanopore or nanotube entrance has a smaller diameter or size than the rest (the interior) of the nanopore or nanotube to exhibit a re-entrant configuration;

(iii) a dual structured biomaterial comprising (A) micro- or macro-pores, wherein the micro or macro pores has an average diameter, or equivalent diameter if the pores are not circular, in the range of between about 0.5 to 1,000 μm, or between about 1 to 100 μm, and optionally the entrances of the micro or macro pores have a smaller diameter or size than the rest (the interior) of the micro or macro pores; and, (B) a surface area covered with nanotubes, optionally $TiO_2$ nanotubes, having an average pore diameter in the range of between about 30 to 600 nm;

(iv) a plurality of enlarged diameter nanopores and/or nanotubes, wherein the nanopores and/or nanotubes comprise at least 150 nm, or optionally at least 200 nm, or at least 400 nm;

(v) an array comprising a solid substrate and a plurality of vertically aligned, laterally spaced, nanotubes associated with the substrate, wherein each nanotube comprises a nanopore;

(vii) an array comprising a solid substrate and a plurality of vertically aligned, laterally spaced, nanotubes associated with, or built into or onto, the substrate, wherein each nanotube comprises a nanopore, and the array comprises a cell, wherein optionally the cell is suitable for implantation, and optionally the cell is suitable for implantation and regeneration of an organ or a dental tissue in a subject;

(viii) an array comprising a solid substrate and a plurality of vertically aligned, laterally spaced, nanotubes associated with the substrate, wherein each nanotube comprises a nanopore and wherein the array comprises a cell suitable for implantation and regeneration of a bone and/or a joint tissue in a subject;

(ix) an array comprising a solid substrate and a plurality of vertically aligned, laterally spaced, nanotubes associated with the substrate, wherein each nanotube comprises a nanopore and wherein the array comprises one or more biologically active agents selected from the group consisting of a therapeutic drug, a growth factor, a protein, an enzyme, a hormone, a nucleic acid, an RNA, a DNA, a gene, a vector, a phage, an antibiotic, an antibody, a small molecule, a radioisotope and a magnetic nanoparticle or particle;

(x) a two or a three-dimensional array comprising (A) a solid substrate comprising Ti, Zr, Hf, Nb, Ta, Mo and/or W wires, ribbons or rods, or any combination thereof; and (B) a plurality of vertically aligned, laterally spaced, nanotubes associated with the substrate, wherein each nanotube comprises a plurality of nanopores;

(xi) a product of manufacture comprising a size-randomized and shape-randomized nanopore- or nanotube-comprising surface made by a method comprising the following steps (A) providing a composition comprising a Ti, Zr, Hf, Nb, Ta, Mo and/or W metal surface; a Ti, Zr, Hf, Nb, Ta, Mo and/or W alloy surface; and/or, a Ti, Zr, Hf, Nb, Ta, Mo and/or W oxide or nitride, and/or stainless steel or ceramic, (B) depositing a semi-wettable coating on a metal, alloy or oxide surface of (A) by employing lithographic patterning or by a thin film deposition technique, wherein the coating decomposes into nano- or micro-islands of local etch masks, and (C) chemical etching or electrochemical anodization of the etch-masked surface, thereby generating a size-randomized and shape-randomized nanopore- or nanotube-comprising surface;

(xii) an elastically compliant nanostructure substrate comprising any combination of (i) to (xi), and/or a structure of (A);

(xiii) any combination of (A) or (B)(i) to (xii), and/or a structure of (A), comprising or configured as an optically transparent or translucent cell-culturing substrate, which optionally is a nano imprint patterned nanostructure;

(xiv) any combination of (A) or (B)(i) to (xiii), in the form of a particle aggregate or a mesoporous structure, or comprising a nanowire or ribbon forest, or comprising directionally etched porous materials or a porous thin film;

(xv) any combination of (A) or (B) (i) to (xiv), wherein the structures partially or completely coating the biocompatible surfaces have a thickness of at least about 1, 2, 3, 4, 5, 6, 7, 8, 9 or 10 or more nm, or a thickness of between about 1 to 10 nm., or a thickness of between about 1 to 15 nm., or a thickness of between about 1 to 20 nm.; or (xvi) any combination of any of these structural embodiments of the invention.

In alternative embodiments of the products of manufacture of the invention, the thin, macro or microscale members and/or the nanotube array structure, or a structure of the invention, comprises a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic. In alternative embodiments, the thin, macro or microscale members and/or the nanotube array structure have a thickness of at least about 1, 2, 3, 4, 5, 6, 7, 8, 9 or 10 or more nm, or a thickness of between about 1 to 10 nm., or a thickness of between about 1 to 15 nm., or a thickness of between about 1 to 20 nm.

In alternative embodiments, at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or all, of the biocompatible surface or the nanotube or nanopore surface comprises or is covered or coated by a structure of the invention.

In alternative embodiments, the matrix material, or a structure of the invention, comprises (i) a Ti, Zr, Hf, Nb, Ta, Mo and/or W metal; (ii) an oxide of (i); (iii) an alloy of (i); (iv) a Si, a Si oxide, an Al, an Al oxide, a carbon, a diamond, a noble metal, an Au, an Ag, a Pt and/or an Al, Au, an Ag, a Pt alloy, a polymer or a plastic material, a composite metal, a ceramic, a polymer and/or a combination thereof.

In alternative embodiments, the products of manufacture of the invention further comprise a bone cell, a liver cell, a kidney cell, a blood vessel cell, a skin cells, a periodontal cell or a periodontal tissue cell, a stem cell, an organ cell, or wherein the cell is a bone cell, a liver cell, a kidney cell, a blood vessel cell, a skin cells, an organ cell; or, further comprising a plurality of cells, wherein the cells comprise bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof. The cell can be a human or an animal cell, or the product of manufacture further comprises a human or an animal cell.

In alternative embodiments, the products of manufacture of the invention further comprise a hydroxyapatite, a biodegradable polymer, or a bio-compatible or bio-inert bone cement; or further comprising a biological agent, wherein optionally the biological agent comprises a growth factor, a collagen, a nucleic acid, an antibiotic, a hormone, a drug, a magnetic particle, a metallic particle, a ceramic particle, a polymer particle, a drug delivery particle.

The invention provides drug delivery devices comprising a product of manufacture of the invention. The invention provides orthopedic implants or dental implants comprising a product of manufacture of the invention, and optionally the orthopaedic (orthopedic) implant or dental implant comprises a plurality of cells, and optionally the cells comprise bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof.

The invention provides disease detection devices comprising a product of manufacture of the invention.

The invention provides artificial tissue or organs comprising a product of manufacture of the invention, and optionally the artificial tissue or organ comprises a plurality of cells, and optionally the cells comprise bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof.

The invention provides bioreactors comprising a product of manufacture of the invention. The invention provides biomimetic arrays, or artificially constructed cell cultures, comprising a product of manufacture of the invention, and optionally also comprising at least a cell for performing drug or chemical toxicity testing, and optionally the cell is a liver cell or liver parenchymal cells.

The invention provides methods for evaluating a drug or a chemical, a pesticide or herbicide, a toxin, a poison, a pharmaceutical, a cosmetic, a polymer or an injection fluid, comprising applying the drug, chemical, toxin, poison, pharmaceutical, pesticide or herbicide, cosmetic, polymer or injection fluid to a biomimetic array, or artificially constructed cell culture, comprising use of a product of manufacture of this invention, wherein optionally method comprises the testing of a new drug or a chemical for safety and/or toxicity issues, and optionally the chemical comprises a toxin, a poison, an allergen, a biological warfare agent, an infectious disease agent or an irritating agent.

The invention provides methods for diagnosing or detecting a disease comprising implanting a product of manufacture of the invention in a subject, wherein optionally the implant is a biochip comprising a disease detection compound or device.

The invention provides methods for detecting an infectious disease agent, or a biological warfare or a bio-terror agent, the method comprising providing a product of manufacture of the invention, wherein the product of manufacture comprises an infectious disease agent, biological warfare or bio-terror agent detection compound or device, and optionally the product of manufacture is a implant.

The invention provides systems for growing and harvesting selected cells, the system comprising: (a) a product of manufacture of the invention operably associated with a device for removing the cells or tissue from the product of manufacture; and (b) a computer operably associated with a), wherein the computer comprises instructions for automatically contacting the cells with a suitable growth media and for harvesting the mature cells.

The invention provides methods for treating a cell proliferation disorder, the method comprising: (a) implanting a product of manufacture of the invention, into a subject, wherein the product of manufacture comprises a biological agent for treating the cell proliferation disorder, and optionally the product of manufacture is implanted at or near the site of a cell proliferation disorder; and (b) contacting the product of manufacture with magnetic agitation, wherein optionally the agitation accelerates biological agent release; and optionally provides magnetic hyperthermia treatment at the site of implantation, and optionally the magnetic agitation comprises external stimulation of the magnetic nanoparticles by alternating current (AC) magnetic field; and optionally the biological agent is released from the array by mechanical agitation/movement of the magnetic particles or by heating of the composition resulting from the AC magnetic field.

The invention provides methods for selectively releasing a biological agent in a subject, the method comprising (a) implanting a product of manufacture of the invention, in a subject, wherein the product of manufacture comprises a biological agent in a colloidal composition; and, (b) contacting the product of manufacture with ultrasonic or magnetic agitation of the colloidal composition, wherein the biological agent is released from the product of manufacture; and optionally the magnetic nanoparticle is selected from the group consisting of iron-oxide particles of magnetite ($Fe_3O_4$) or maghemite (γ-Fe2O3), and optionally the magnetic nanoparticle is about 5 to 50 nm in average diameter.

The invention provides methods for accelerating the growth of cells, the method comprising contacting the cells with a product of manufacture of the invention, in the presence of a nutrient fluid suitable for sustaining growth of the cells.

The invention provides multi-functional implant devices comprising a product of manufacture of the invention, wherein the product of manufacture comprises a biologically active agent selected from the group consisting of a pharmaceutical composition, a therapeutic drug, a cancer drug, a growth factor, a protein, an enzyme, a hormone, a nucleic acid, an antibiotic, an antibody, a nanoparticle and a biologically active material. In one aspect, of the multi-functional implant device, the product of manufacture comprises a colloidal liquid comprising the biologically active agent, and the product of manufacture is designed for externally controlled release of the colloidal liquid upon application of ultrasonic or magnetic stimulation; and optionally the colloidal liquid comprises a biologically active agent and magnetic nanoparticles; and the magnetic nanoparticles are selected from the group consisting of biocompatible iron-oxide particles of magnetite ($Fe_3O_4$) and maghemite ($\gamma$-$Fe_2O_3$); and optionally the size of the magnetic nanoparticles is from about 5 to 50 nm in diameter. In one aspect, of the multi-functional implant device, the product of manufacture comprises nanotubes, and a cap is deposited at the upper end of a nanotube by an oblique incident sputter deposition on a stationary or a rotating substrate; and optionally the cap is narrowed such that a colloidal liquid is retained in the nanotube before external stimulation for controlled release.

The invention provides methods of externally controlled release of a colloidal liquid into a subject comprising applying external stimulation by alternating current magnetic field to the multi-functional implant device of the invention, wherein the magnetic field causes agitation, movement and heat production from the magnetic nanoparticles comprised in the colloidal liquid resulting in its release from the implant device.

The invention provides methods for ameliorating or treating cancer, wherein the multi-functional implant device of the invention is implanted into a subject at the site of cancer; and optionally external stimulation is applied resulting in the local delivery of anti-cancer drugs and magnetic hyperthermia treatment.

The invention provides methods of cell proliferation comprising a product of manufacture of the invention, and adherent cells, wherein upon adhesion the cells are induced to proliferate; and optionally the cells are grown in vivo, ex vivo or in vitro, and optionally after proliferation, the cells are harvested.

The invention provides analytical diagnostic biochips comprising a product of manufacture of the invention, wherein the biochip is used for the rapid diagnosis or detection of diseased cells, cells involved in an infectious or an epidemic disease or exposed to a chemical or a toxic agent, or cells exposed to a biological warfare agent, or cells that are related to forensic investigations.

The invention provides methods for making a product of manufacture of the invention, comprising simple dropping of the structures of the invention onto the biocompatible surface, and bonding the structures onto the surface under compression or by utilizing electric arc spot welding or heating to high temperature for diffusion bonding.

The invention provides nano-patterned, see-through cell culture substrates comprising a polymer, polycarbonate, plastic or glass base coated with is covered or coated by a structure comprising: (i) a plurality of thin, macro or microscale members in a hairy, a gauge, a wire, a woven wire, a spring, a ribbon, a powder, a flake shaped structure and/or a particulate array configuration, wherein the thin, a macro or a microscale member comprises a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic, wherein the plurality of thin, macro or microscale members are fixed or loosely placed, or a combination thereof, on the biocompatible surface; (ii) a plurality of loose, short-fibers, or flake shaped structures, or particles of Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic, wherein optionally the fibers or particles are straight, curved and/or bent, and optionally the spring-like fibers or mesh screen shapes are fixed or loosely placed, or a combination thereof, on the biocompatible surface; (iii) a plurality of micro-wires, micro-fibers or micro-ribbons, wherein optionally the wires, ribbons or fibers are straight, curved and/or bent, wherein optionally the micro-wires, micro-fibers or micro-ribbons are fixed or loosely placed, or a combination thereof, on the biocompatible surface; (iv) a plurality of spring-like fibers or mesh screen shapes comprising a Ti or metal material, an alloy and/or a ceramic, wherein optionally the spring-like fibers or mesh screen shapes are fixed or loosely placed, or a combination thereof, on the biocompatible surface; (v) a structure as illustrated in FIGS. 1, 2, 5, 6, 7, 8, 9, 10, 11, 12, 13, 14, 15 and/or 16; (vi) any of the structures of (i) to (v) in the form of a high-surface-area wire array, a mesh screen array, a particle assembly array or a combination thereof; (vii) any combination of the structures of (i) to (vi), and optionally any combination of the structures of (i) to (vi) are fixed or loosely placed, or a combination thereof, on the biocompatible surface.

The invention provides optically transparent or translucent cell-culturing substrates with nano imprint patterned nanostructure comprising a product of manufacture of the invention. The invention provides biocompatible and cell-growth-enhancing culture substrates comprising an elastically compliant protruding nanostructure substrate coated with Ti, $TiO_2$ or related metal and metal oxide films (e.g., comprising a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic), wherein the nanostructure comprises a product of manufacture of the invention.

The invention provides methods of making a porous biomaterial surface nanostructure capable of controlled delivery of biological agents using a product of manufacture of the invention, by additional oblique incidence sputtering or evaporation, quick electroplating, quick electroless plating, or quick dipping in adhesives for partially capping the entrance of the pores to reduce the pore-entrance-diameter, followed by inserting biological agent into the nanopores. In alternative aspect, the biological agent is selected from a list of a growth factor, a collagen, a nucleic acid, an antibiotic, a hormone, a drug, magnetic particles, metallic particles, ceramic particles, polymer particles and a combination thereof; or the magnetic particles, metallic particles, ceramic particles, or polymer particles are pre-inserted before the pore diameter reducing cap material is deposited to minimize inadvertent release of the particles outside the biomaterial surface; or the biomaterial surface nanostructure with nanotube, nanowire, or nanopore configuration is made from a substrate material comprising Ti, Zr, Hf, Nb, Ta, Mo or W metal material, a Ti, Zr, Hf, Nb, Ta, Mo or W alloy, or a combination thereof, by a method comprising one or more of processes selected from DC or RF sputter deposition, oblique incident evaporation, chemical vapor deposition, laser surface melting and solidification, RF surface melting and solidification, chemical etching, patterned-mask-guided chemical, reactive ion etching and a combination thereof; or the porous biomaterial is in bulk or thick film configuration and is made of non refractory metal related materials comprising silicon, polymer, plastic, glass or ceramic material, and the surface of the biomaterial is pre-coated with a biocompatible, cell-culture-enhancing thin film layer comprising Ti, Zr, Hf, Nb, Ta, Mo or W metal material, a Ti, Zr, Hf, Nb, Ta, Mo or W alloy, Ti, Zr, Hf, Nb, Ta, Mo or W oxide, or Ti, Zr, Hf, Nb, Ta, Mo or W nitride, and wherein the pre-coating is made by a method comprising a physical deposition method comprising sputtering, evaporation or atomic layer deposition, or a chemical deposition method selected from CVD deposition, electrodeposition or electroless deposition; or wherein the porous biomaterial surface is in a configuration of macro-, micro- or nano-particle aggregate and is made by a method comprising sintering or gluing of particles, which optionally can comprise a mesoporous carbon, mesoporous silicon, mesoporous metal, mesoporous ceramic or mesoporous polymer onto a rigid surface.

The invention provides methods of remote-operating drug delivery system comprising an array of magnetic nano-ribbon, magnetic micro-ribbon, magnetic nanowire, magnetic micro-wire, carbon nanotubes coated with magnetic material by applying remote magnetic field to sequentially move the magnetic elements.

The invention provides methods of making loose particle, flake, or fiber based large-surface-area, biocompatible, cell-culture-enhancing or bone-growth-enhancing surface having a nanotube covered structure comprising: (a) selecting a material comprising Ti, Zr, Hf, Nb, Ta, Mo or W metal material; a Ti, Zr, Hf, Nb, Ta, Mo or W alloy; or Ti, Zr, Hf, Nb, Ta, Mo or W oxide, or Ti, Zr, Hf, Nb, Ta, Mo or W nitride; and, (b) introducing a relative rotational, lateral or shaking movement between the particles, flakes or fibers and the electrode so that the surface of the Ti and refractory metal loose particles is anodized to form nanotube-covered surface.

The invention provides methods of making loose particle, flake, or fiber based large-surface-area, biocompatible, cell-culture-enhancing or bone-growth-enhancing surface having a nanotube covered structure, comprising: (a) applying a sodium hydroxide or potassium hydroxide chemical reaction with the particle material comprising Ti, Zr, Hf, Nb, Ta, Mo or W metal material, or a Ti, Zr, Hf, Nb, Ta, Mo or W alloy, to form a sodium titanate or related nanotube or nanofiber array structure on the particle surface; (b) providing hydrothermal treatment to convert the sodium titanate or related nanotube or nanofiber array into oxide nanotube array; and (c) heat treating to convert amorphous nanotube or nanofiber into crystalline structure.

The invention provides methods of making loose particle, flake, or fiber based large-surface-area, biocompatible, cell-culture-enhancing or bone-growth-enhancing surface having a nanotube covered structure, comprising: (a) by selecting a sheet, ribbon or wire material comprising Ti, Zr, Hf, Nb, Ta, Mo or W metal material, a Ti, Zr, Hf, Nb, Ta, Mo or W alloy, Ti, Zr, Hf, Nb, Ta, Mo or W oxide; (b) anodizing the refractory metal wire or sheet to form a partially or fully penetrating metal oxide nanotube structure, optionally crystallizing the oxide to anatase or rutile phase; and (c) breaking up the oxidized material into loose powders or fibers, optionally filling the nanotube pores with biological agents for accelerated cell or bone growth, or for therapeutic drug release purpose.

The invention provides nano-patterned, see-through cell culture substrate structures comprising a transparent thermosetting polymer, transparent thermoplastic polymer, transparent UV-light-curable polymer, or transparent glass base which is covered or coated with an optically transparent or translucent, and very thin film of material comprising Ti, Zr, Hf, Nb, Ta, Mo or W metal material, a Ti, Zr, Hf, Nb, Ta, Mo or W alloy, a Ti, Zr, Hf, Nb, Ta, Mo or W oxide, or Ti, Zr, Hf, Nb, Ta, Mo or W nitride. In alternative aspects of the nano-patterned, see-through cell culture substrate structures, the nano-patterned or micro-patterned surface microstructure of the substrate has either pillars, tubes, lines, or pores with approximately 10 nm to approximately 500 μm feature size; or, the nano-pattern is periodic or the nanopattern is random in size, shape or distribution; or the thermosetting polymer is selected from polydimethylsiloxane (PDMS), polymethyl methacrylate (PMMA), melamine, Bakelite and epoxy resins; or the said thermoplastic polymer is selected from polyethene, polypropene, polystyrene, or poly vinyl chloride; or the UV-curable polymer is selected from polydimethylsiloxane (PDMS) and polymethyl methacrylate (PMMA); or the optical transparency is at least 20%, or at least 40%, of the light sent through the substrate; or the thicknesses (thinnesses) of the transparent or translucent coatings (e.g., Ti or $TiO_2$ related alloys, oxides, etc) is in a range of about 1 to 50 nm.

The invention provides methods of fabricating the nano-patterned, see-through cell culture substrate of claim 43, comprising the step of imprinting using a stamp with pre-patterned surface, or nanoscale surface etching using solvents or chemicals. In alternative aspects, the nano-patterning is carried out by a method comprising permanent mechanical impressing of a nano-patterned stamp on soft substrate material selected from the group consisting of uncured thermosetting polymer, heated and softened thermoplastic polymer, or heated and softened glass; or the patterning is performed by a method comprising wet resist pattern transfer onto a transparent cell culture substrate using a surface-patterned stamp followed by curing and chemical or reactive ion etching of the cell culture substrate through patterned resist layer and optional removal of the resist layer; or the patterning is performed by a method comprising impressing of a stamp into a continuous layer of liquid resist film coating on a transparent plastic or glass followed by curing and chemical or reactive ion etching through patterned resist layer and optional removal of the resist layer; or the curing of wet, patterned polymer is performed by a method comprising thermal heat curing while it is being impressed by a nano or microstamp; or the curing of wet, patterned polymer is performed by a method comprising UV light illumination curing while it is being impressed by a nano or microstamp; or the coating of an inorganic film of Ti, Ti oxide, Ti nitride and related refractory metals, oxides or nitrides on surface nano-patterned transparent substrate is carried out by a method comprising physical or chemical means including sputtering, evaporation, atomic layer deposition, chemical vapor deposition, electroless plating or electroplating.

The invention provides methods of making a biocompatible and cell-growth-enhancing culture substrate comprising an elastically compliant protruding nanostructure substrate coated with Ti, $TiO_2$ or related metal and metal oxide films, comprising: (a) providing a surface nanopatterned stamp; (b) impressing into a wet, uncured elastomer layer with the nanostamp; (c) curing the polymer while being impressed by thermal curing or UV light curing; (d) releasing and removing the stamp; (e) depositing a thin film of Ti, Zr, Hf, Nb, Ta, Mo or W metal material, a Ti, Zr, Hf, Nb, Ta, Mo or W alloy, a Ti, Zr, Hf, Nb, Ta, Mo or W oxide, or Ti, Zr, Hf, Nb, Ta, Mo or W nitride by a method comprising a physical or chemical thin film deposition method. In alternative aspects, the elastically compliant protruding nanostructure has a configuration of a periodic or a random array of nanopillars, nanoballs, nanolines or nanomesh elements, or a combination thereof.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of embodiments of the invention and are not meant to limit the scope of the invention as encompassed by the claims. The advantages, nature and additional features of the invention will appear more fully upon consideration of the illustrative embodiments described in the accompanying drawings. In the drawings:

FIG. 1*a* illustrates a hairy or gauze Ti wire mesh; FIG. 1*b* illustrates the strongly locked in bone growth possible around the compliant, hairy or mesh screen structures of this invention.

FIG. 3*a* illustrates a cell adhered and growing on an exemplary nanotube structure of this invention; FIG. 3*b* illustrates a cell adhered and growing on an exemplary nanopore structure of this invention.

FIG. 5*a* shows an exemplary protruding structure comprising hairy or mesh screen Ti wire on an implant; FIG. 5*b* shows anchoring thick film Ti deposit (1-2000 micrometer thick), optionally oblique incidence plus rotating substrate; FIG. 5*c* shows an exemplary diffusion annealed and bonded Ti layer (at 500-1300° C./0.1-100 hrs); FIG. 5*d* shows both the Ti wire surface and flat Ti surface are anodized to have $TiO_2$ nanotube or nanopore structure.

FIG. 6*a* shows an exemplary method comprising use of an induction-heating RF wave, plasma heating, e-beam heating, laser heating, torch heating and/or furnace heating; FIG. 6*b* shows the melt-bonded contact region between the mesh and substrate; FIG. 6*c* shows exemplary $TiO_2$ nanotubes on the wire surface by anodization; FIG. 6*c* shows exemplary recessed nanopores with TiO2 surface on the Ti wire surface.

FIG. 7*a* shows an exemplary method using a spot welding upper electrode in the shape of disk, plate, grid, vertical rod array, frame; in one aspect, the contact region is a noble metal, e.g., Au, Pt, Pd or alloys; FIG. 7*b* shows an exemplary spot welded Ti region; FIG. 7*c* shows exemplary $TiO_2$ nanotubes on the wire surface by anodization; FIG. 7*d* shows exemplary recessed nanopores with $TiO_2$ surface on the Ti wire surface.

FIG. 8*a* shows exemplary methods comprising spot-welded, or induction melting-bonded, e-beam bonded, laser-bonded or braze-bonded Ti wire mesh (single layer or multi-layer), having surface $TiO_2$ nanopore or nanotube array; FIG. 8*b* shows a strongly locked-in bone (or cell) growth around an exemplary woven or compliant, gauze Ti wire mesh structure of this invention.

FIG. 9*a* shows an exemplary bonded protruding hairy wire or mesh screen Ti with surface nanopore or nanotube $TiO_2$; FIG. 9*b* shows an exemplary hairy or mesh-screen Ti wire mesh with surface nanopore or nanotube $TiO_2$.

FIG. 10*a* shows an exemplary protruding Ti micro or macro particles (or a cross-sectional view of fibers) attached on Ti implant surface, by induction melt-bonding, e-beam melt bonding, laser bonding, spot-welding, braze-bonding, etc., and Ti implant with flat, round or curved surface Ti implant; FIG. 10*b* shows an exemplary surface modified Ti particles or fibers (and also the surface of the implant base itself) with anodization-induced TiO2 nanotube or nanopore surface; FIG. 10*c* shows an exemplary nanoscale+microscale structure with strongly locked-in bone growth around Ti particles or fibers.

FIG. 12*a* shows an exemplary surface modified Ti particle aggregate with anodization-induced TiO2 nanotube or nanopores on the particle surface, and an exemplary drug or biological agent (such as antibiotics, chemotherapy medicine, anti-stenosis drug, insulin, DNA, hormone, growth factor, etc.) inserted into the nanopores, with a Ti support of implant with flat, round or curved surface; FIG. 12*b* shows an exemplary surface modified Ti particle aggregate with anodization-induced TiO2 nanotube or nanopores on the particle surface with magnetic nanoparticles and drug or biological agent, and a Ti support or implant with flat, round or curved surface.

FIG. 13*a* shows an exemplary use of mesoporous carbon, mesoporous silicon, mesoporous metal, mesoporous ceramic or a mesoporous polymer aggregate; and a biocompatible substrate such as Ti, inert metal, ceramic, polymer, any material coated with biocompatible surface layer; and FIG. 13*b* shows an infiltrated (e.g., a drug or biological agent+magnetic nanoparticles), e.g., by an exemplary method comprising supercritical fluid deposition, or a boiled liquid method.

FIG. 14*a* shows an exemplary actuate-able nanowire (such as carbon nanotube forest coated with magnetic material), magnetic nano- or micro-ribbon, or magnetic nano- or micro-wire; FIG. 14*b* shows how capillary-trapped drug or biological agent is released by induced movement of magnetic wires or ribbons, and how the magnetic wire or ribbon is actuated to move by a remote magnetic field, e.g., a regular, sequential or gradient field applied; and FIG. 14*c* shows an exemplary device of the invention comprising a non-magnetic wire or ribbon forest, e.g., aligned or partially tangled, comprising a capillary-trapped drug or biological agent, and how magnetic nanoparticles can make the drug solution be released by a field-induced magnetic particle movement or by a high-frequency magnetic field heating of particles, and the movement inducing the release of the compound in the liquid (e.g., release of a drug-containing liquid).

FIG. 15*a* is meant to illustrate how a base material can be etched to form directional nano or micro-pores, where the base material can be, e.g., Al, Si, ceramics, other metals or a polymer, or it can be a single phase material, or alternatively a two-phase or composite material for ease of selective etching; FIG. 15*b* illustrates exemplary vertical pores formed in the base, e.g., a ceramic, Si, metal/alloy, or polymer material, prepared by chemical or electrochemical etching, thermal or plasma etching, utilizing differential melting point or differential vapor pressure of component phases, differential sputter etch rate or ion etch rate (crystal orientation dependent or two phase's composition-dependent), or post-thermal chemical etching of melt textured (directional solidified) structure by induction, laser or e-beam melting, or sputter/resputter process. Optionally, a biocompatible coating can be applied; FIG. 15*c* illustrate the optional use of partial capping to reduce the pore entrance size, e.g., by oblique incidence sputtering or evaporation, quick electroplating, quick electroless plating, or quick dipping in adhesives; FIG. 15*d* illustrates how drugs or biological agents can be present in aqueous solutions, as dissolved or as colloidal solutions, and optionally, also comprising magnetic nanoparticles for remote-actuated drug delivery.

FIG. 16*a* shows an exemplary porous Ti or $TiO_2$ surface made by evaporation, or by DC or RF sputtering, on a substrate; FIG. 16*b* shows this exemplary product of the invention comprising a biological agent, such as a growth factor, collagen, a hormone, a DNA or nucleic acid, etc.; FIG. 16*c* shows how magnetic or other movable functional particles and desired compositions, e.g., a drug, a DNA or nucleic acid, a growth factor, a hormones, etc., can be released by local heating, local magnetic field, electrical impulses for, e.g., controllable drug delivery, etc.

FIG. 18*a* shows an exemplary Ti or Ti alloy implant (flat, round or curved surface), optionally with $TiO_2$ nanotube or nanopore surface; and an exemplary compliant, springy, or bent Ti wire, ribbon and/or mesh screen of pure metal or alloy, with $TiO_2$ nanotube or nanopore surface (e.g., made by oblique incident evaporation, sputtering, or welding, brazing, induction-melt-bonding, e-beam melt-bonding, laser-melt-bonding, spot welding, etc), and optionally comprising $TiO_2$ nanotube or nanopore surface on the Ti wire surface, and optionally comprising spacer/protector for abrasive insertion of Ti implants (e.g., screw-like implants into bones); FIG. 18*b* shows an exemplary Ti mesh screen bonded onto Ti implant; FIG. 18*c* shows an exemplary method comprising applying pressure and electric voltage to the spot welder electrode array, and the spot welder electrode array, in this example generating bent, springy Ti wires; and FIG. 18*d* shows an exemplary spot welder electrode array in this example generating a Ti mesh screen bonded onto Ti implant.

FIG. 19*a* showing an intermediate stage of bone growth around an exemplary compliant Ti spring implant, with compliant Ti wires or ribbons with $TiO_2$ nanotube or nanopore surface; and an optional spacer/protector for abrasive insertion of Ti implants (e.g., screw-like implants); and FIG. 19*b* shows an exemplary product of the invention comprising ribbons with $TiO_2$ nanotube or nanopore surface; the compliant Ti serves as reinforcement as in a reinforced concrete.

FIG. 20*a* shows an exemplary product of the invention comprising non-Ti type, nanoporous or microporous materials (e.g., anodized $Al_2O_3$ membrane, porous Si, porous polymer), including nanopores or micropores, which optionally can be between about 20 to 2000 nm diameter; FIG. 20*b* shows an exemplary Ti, $TiO_2$ type coating, e.g., with 5 to 100 nm thick layer thick coating by sputtering, evaporation, chemical vapor deposition; FIG. 20*c* shows how cells or bones are grown in an accelerated manner on this exemplary Ti- or $TiO_2$-type coated nanopore structure.

FIG. 21*a* shows an exemplary product of the invention comprising non-Ti type substrate, e.g., comprising ceramics, polymers, plastics, Si, Au, Pt, Al, etc.; FIG. 21*b* shows an exemplary product with a configuration/shape made by macro- or micro-shaping, e.g., by photolithography, machining, shadow mask polymer coating plus chemical etching, etc.; FIG. 21*c* shows an exemplary Ti type metal coating, e.g., with Ti, Zr, Hf, Nb, Ta, Mo, W and their alloys among themselves or with other elements, by sputtering, evaporation, chemical vapor deposition, plasma spray, thermal spray, etc., FIG. 21*d* shows how cell- or bone-growth is accelerated by a coating of $TiO_2$ nanotubes or nanopores by anodization.

FIG. 23*a* shows various exemplary implants, including dental, periodontal, elbow, hip, knee and leg implants; FIG. 23*b* shows exemplary implant comprising implanted cells or organs, or an exemplary artificial liver of this invention; FIG. 23*b* shows exemplary drug-containing or drug delivery devices for, e.g., stents or other blood vessels, and exemplary devices for, e.g., insulin, etc., or therapeutic devices, e.g., for cancer treatment, etc.

FIG. 26*b* shows an exemplary chemical or biological analysis with a chemical or biological detection, e.g., based on signature reactions; and FIG. 26*c* shows a magnetic sensor technique for magnetic sensor detection, e.g., by using magnetically targeted antibody, including use of a GMR or TMR sensors as a magnetic sensor array.

FIG. 29*a* illustrates use of Ti wire or sheet; FIG. 29*b* illustrates use of anodized Ti wire or sheet with mostly $TiO_2$ surface+optional crystallization heat treatment; FIG. 29*c* illustrates use of ground, crushed or cut $TiO_2$ or related material (a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic) into powder, flake, short wire, etc.

FIG. 31 describes an exemplary dental use of $TiO_2$-nanotube-coated powders or mesh screen of $TiO_2$ (with optional Ti core) for accelerated dental bone growth; and use of an exemplary product of this invention for accelerated growth of regenerated dental bone on templates of loose $TiO_2$ (with optional Ti core) having nanotube or nanopore surface, in the configuration of microwire mesh, powder, flake, etc. with optional growth factors, nutrients, antibiotics, hormones, genes, hydroxyapatite, natural bone powder, bio-degradable polymer, bio-compatible or bio-inert bone cement, magnetic nanoparticles, etc.

FIG. 33*a* shows nano-imprint stamping, e.g., to generate pillars, lines or pores, having about a 10 nm to 500 μm feature size. FIG. 33*a* also shows as a top layer, a soft matrix (uncured thermosetting) polymer, heated thermoplastic polymer, uncured glass precursor, heat-softened glass, etc. and the bottom layer a support structure. FIG. 33*a* shows an exemplary nanoimprinting process at room temp or elevated temperature, which can be heat cured, UV cured, catalyst cured polymer and/or solidified by cooling, e.g., glass, thermoplastic polymer. FIG. 33*c* shows an exemplary nano-cavity, nanopillar or nano-grid, e.g., designed to be periodic or intentionally nonperiodic to minimize diffraction and interference of passing light. FIG. 33*c* shows an exemplary deposited thin film, e.g., as a Ti or $TiO_2$, or other bio-compatible metals, alloys, oxides, nitrides of Zr, Ta, Nb, Mo, Hf, Cr, and/or stainless steel or ceramic, and the like, deposited using, e.g., oblique or vertical sputtering, evaporation, etc.

FIG. 33*a* shows an exemplary periodic nanopattern of Ti, $TiO_2$ or related metals or oxides-coated cell culture substrate. FIG. 33*b* shows an exemplary random, or non-periodic nanopattern of Ti, $TiO_2$ or related metals or metal oxide-coated cell culture substrate.

As shown in FIG. 35*a*, the liquid resist layer can be cured by heat or UV light, or impressed on thermoplastic solid polymer. As shown in FIG. 35*b*, alternatively, one can continue an RIE Etch or apply chemical etch for substrate patterning; then one can remove the resist later and deposit thin, almost or completely transparent Ti, $TiO_2$ or related metals or oxides coating on the transparent substrate.

FIG. 36*b* shows an exemplary ink transfer by an imprinting process. FIG. 36*c* shows an exemplary patterned ink, nano- or micro-patterned "resist" array. FIG. 36*d* shows an exemplary protruding nanopillar or recessed nanopore pattern made by chemical or RIE etch. FIG. 36*e* shows an exemplary process depositing thin film Ti, $TiO_2$ or related metals or oxides, including nitrides and the like.

FIG. 38*a* shows an exemplary method for imprinting the a "nano" stamp on a wet, uncured polymer resist layer, e.g., a UV-curable or a heat-curable layer, e.g., PDMS. FIG. 38*b* shows an exemplary method to UV-cure, e.g., by UV light illumination through transparent substrate or by heating. FIG. 38*c* shows stamp release to obtain a nano-imprinted polymer pattern. FIG. 38*d* shows the results of the additional step of coating with, e.g., a thin layer of Ti or $TiO_2$, or a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic. FIG. 38*e* shows the substrate after peeling off the support structure.

Figure 1:
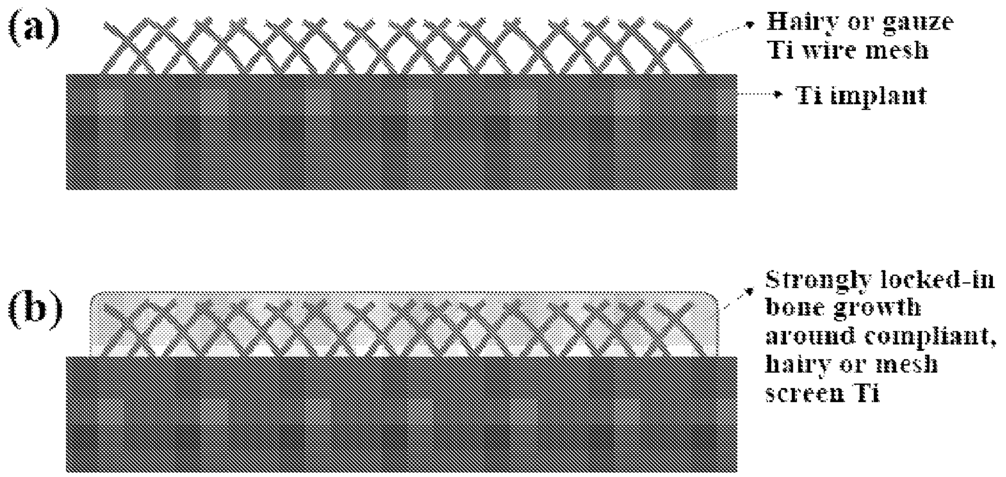
FIG. 1 schematically illustrates exemplary configurations of an extended and protruding, wire-like biocompatible structure for improved toughness, strength, and mechanical locking of bone growth around compliant, hairy-shaped or mesh-screen-shaped Ti (or Ti alloy), or any biocompatible alloy such as stainless steel, attached on the Ti implant surface (functions, e.g., like reinforced concrete).

It is to be understood that the drawings are for purposes of illustrating the concepts of the invention and are not to scale.

DETAILED DESCRIPTION

The present invention provides biocompatible nanostructures with significantly increased surface area, such as products of manufacture comprising nanotube and/or nanopore arrays on the surface of metallic, ceramic, or polymer materials for e.g., enhanced cell and bone growth, for in vitro and in vivo testing, cleansing reaction, implants and therapeutics, e.g., as drug delivery devices. In one aspect, the invention provides products of manufacture comprising biomaterials comprising Ti oxide type nanostructures with various protruding and extended biomaterial configurations; where these biomaterial configurations can enable accelerated cell growth and can be useful for, e.g., rapid acting and secure orthopedic, dental, periodontal, cell/organ implants, therapeutics, disease diagnostic, drug toxicity testing, and cell supply applications.

Exemplary substrate biomaterials or surfaces of the substrate biomaterials of the invention can comprise Ti and Ti oxide as well as alloys containing Ti or Ti oxide by at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or more weight %. Other related materials such as Zr, Hf, Nb, Ta, Mo, W, and their oxides, or alloys of these metals and oxides by at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or more weight % can also be used.

The structures of the invention can be used with any $TiO_2$ nanotubule array structure, e.g., as described in PCT Patent Application #PCT/US2006/016471, filed on Apr. 28, 2006, Jin et al. Using the structures of the invention can provide enhanced cell and bone growth, or can provide improved Ti or $TiO_2$ configurations in nanopore or nanotube configurations. The nanostructures of the invention can comprise Ti or $TiO_2$ or equivalent structures made of other materials but coated with a biocompatible Ti or $TiO_2$ film. The structures of the invention can allow enhanced cell adhesion and accelerated growth, for example by at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or 100% or faster, and or in another aspect, at least 120%, 150% or 200% or faster.

This invention provides novel, biocompatible nanostructured biomaterials, devices comprising such biomaterials, and fabrication methods thereof. The biomaterials of the invention can have a variety of advantageous structures and surface configurations, as discussed herein:

1. Biomaterials with Strongly Bonded, Protruding Features:

The invention provides products of manufacture/compositions comprising macroscopically or microscopically extended biomaterial topography, which can provide a lock-in mechanical integrity at a implant-hard tissue interface; and in one aspect, providing a $TiO_2$ nanotube type nano structure comprising on its surface one or more protrusion features (e.g., biocompatible surfaces comprising structures, as described herein), and in one aspect, the surface of the base implant provides a desirable cell- or bone-growth-accelerating characteristics.

2. Externally and Remotely Controllable Drug-Delivery Systems:

The invention provides products of manufacture/compositions comprising nanotube or nanopore arrays, or micro-wires or micro-ribbon arrays, e.g., on implant surface, which in alternative aspects are utilized as a reservoir for drug and other biological agents, which can have advantageous characteristics of magnetically actuated, on-demand drug release capability.

3. Elastically Compliant Implant Material for Bone Growth:

The invention provides products of manufacture/compositions comprising subdivided, spring-like fiber or mesh screen shape implants for stress-accommodation and minimal separation failures at the implant-hard tissue interface, which in alternative aspects provides strength and toughness reinforcement of the grown bone via bone-metal wire composite formation.

4. Non-Metallic or Non-Ti Based Substrates the Surfaces of which have been Converted to $TiO_2$ Type Nanotubes or Nanopores:

The invention provides products of manufacture/compositions comprising a thin film coating of Ti and/or $TiO_2$, which can be applied onto the surfaces of already nanoporous material, and/or a thick film Ti is deposited and anodized to create $TiO_2$ nanotube type, which in alternative aspects can exhibit desirable cell or bone growth accelerating characteristics.

5. Biocompatible Materials Configured in Loose Particles, Loose Short-Fibers, or Loose Flakes:

The invention provides products of manufacture/compositions comprising powder surfaces processed to comprise nanopore or nanotube array nanostructure, so that the loose powders exhibit cell- or bone-growth-accelerating characteristics, which in alternative aspects can be useful for bone cement and other tissue connection applications.

The invention provides products of manufacture/compositions comprising optically transparent or translucent, surface-nanostructured polymer, plastic or glass substrates, with coating comprising Ti, Ti oxide, Ti nitride or related refractory metal, oxide or nitride films; and in alternative aspects, also comprising cell-growth-enhancing culture substrates comprising elastically compliant protruding nanostructure substrates coated with, in alternative aspects, Ti, $TiO_2$ or related metal and metal oxide films.

1. Biomaterials with Strongly Bonded, Protruding Features

One exemplary embodiment comprises a solid substrate of biocompatible material which is macroscopically or microscopically extended in space with protruding, strongly and permanently attached, three-dimensional, high-surface-area wire array, mesh screen array, or particle-assembly array. Another exemplary embodiment comprises having the surface of each of these attached wires, mesh screens, or particles processed to have an array of $TiO_2$ nanotube type or nanopore type nanostructure on the surfaces of these protrusion features; and in one embodiment, the high-surface-area wire arrays, mesh screen arrays, or particle-assembly arrays are also on the surfaces of the base implant material itself so as to provide cell- or bone-growth-accelerating characteristics.

In one aspect, these configurations provide large-surface-area biocompatible materials not only from the surface nano-features such as titanium oxide nanotubes or nanopores but the protruding extended three-dimensional structures. The increased overall surface areas together with the conditions of secure cell or bone adhesion at the implant-tissue interface allow accelerated and viable cell growth and bone growth, with significantly enhanced mechanical bond strength due to the extended structure. Optionally, growth factors and other biological agents are added and stored in the nanotubes or nanopores for multifunctional advantages and for even further accelerated growth of healthy cells.

Shown schematically in FIG. 1(*a*) is an exemplary configuration of an extended and protruding, wire-like biocompatible structure for improved toughness, strength, and mechanical locking of bone growth around compliant, hairy-shaped, or mesh-screen-shaped Ti (or Ti alloy such as Ti—V—Al), or any biocompatible alloy such as metals and alloys comprising Zr, Hf, Nb, Ta, Mo, W, or stainless steel, attached on the Ti implant surface. The desired shape of the extended and protruding, wire-like biocompatible structure can be an array of isolated wires with their arrangement in vertical, inclined, or random orientation. The wires or fibers can be either straight, curved or bent. Alternatively, instead of isolated wires, they can be mutually connected, e.g., in the form of mesh screen, woven screen, or gauge shape.

Figure 5:
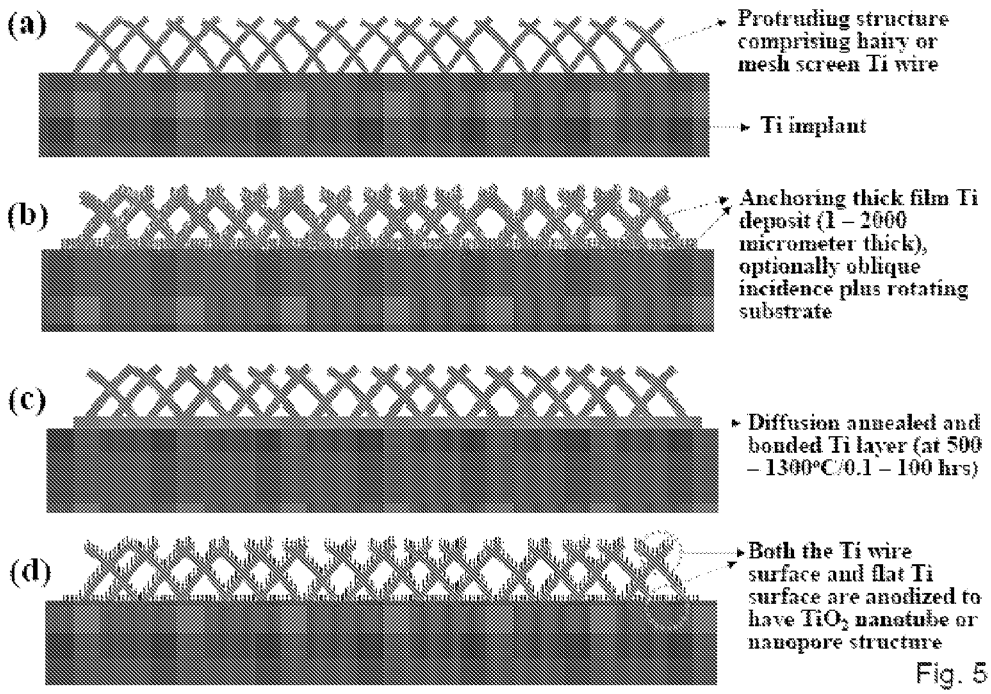
FIG. 5 illustrates an exemplary process of diffusional bonding of hairy Ti or mesh-screen Ti onto the Ti implant base using Ti film deposition followed by high temperature annealing; or hairy or mesh-screen material of any biocompatible alloy such as stainless steel, bonded on any biocompatible alloy such as Ti, Zr, Hf, stainless steel, etc.
Figure 6:
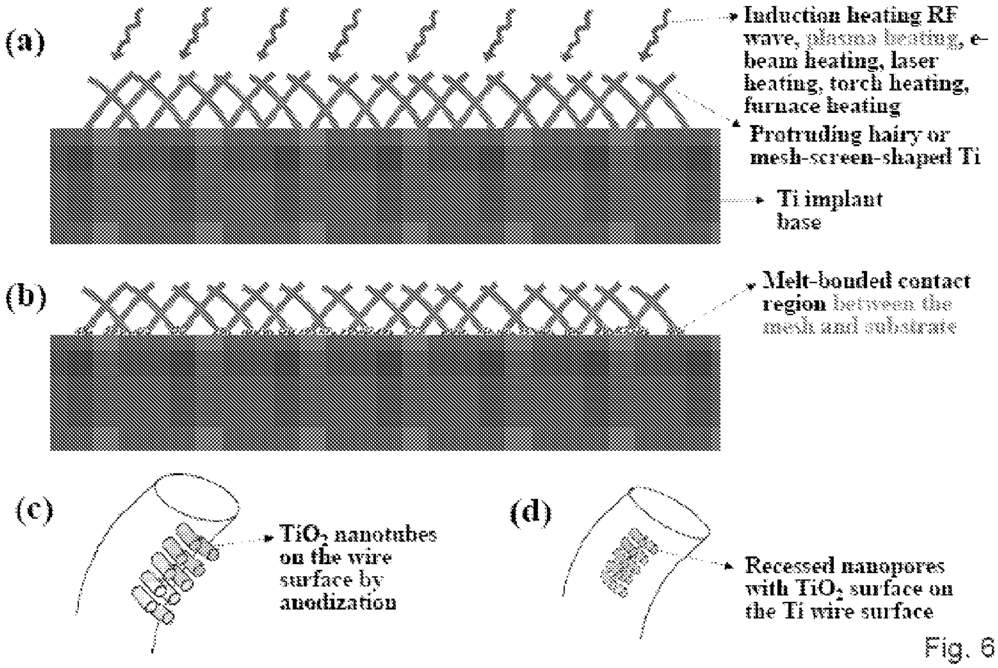
FIG. 6 schematically illustrates exemplary and various melt-bonding techniques for attaching protruding hairy-shaped or mesh-screen-shaped Ti onto the surface of Ti implant, or to any biocompatible alloy such as stainless steel, ceramic, etc., and melt-bonded onto the Ti implant.
Figure 7:
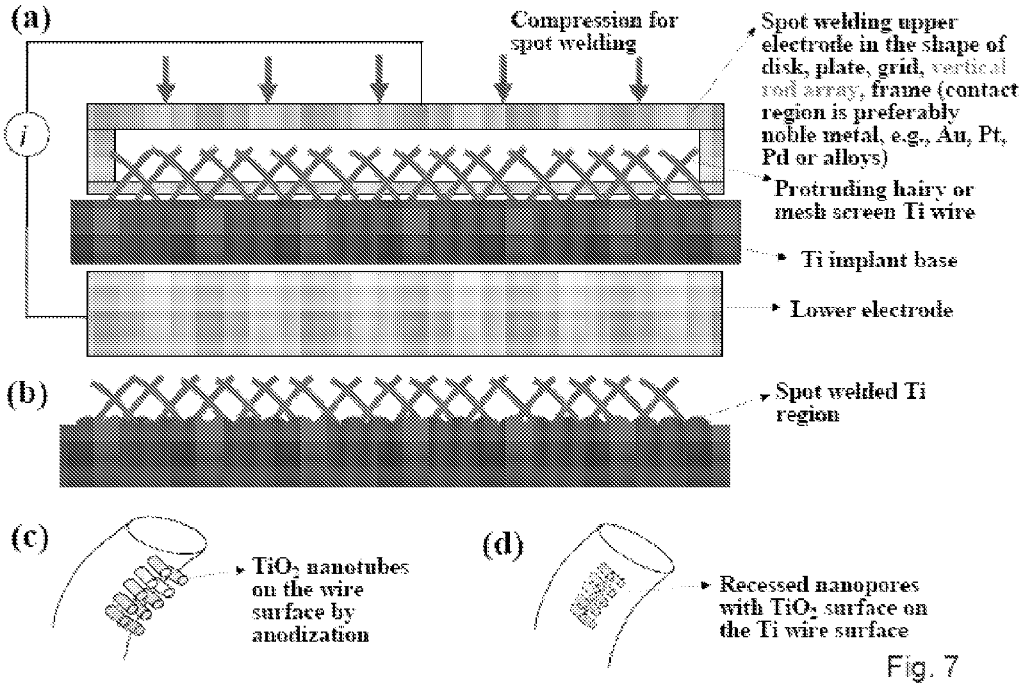
FIG. 7 depicts exemplary hairy Ti or mesh-screen Ti (or any biocompatible alloy such as stainless steel) spot-welded onto the Ti implant.

The protruding part of the structure can be pre-assembled (e.g., in a mesh-screen shape) and then bonded onto the substrate by various methods such as diffusion bonding, or partial melt bonding, such as by using as e-beam, laser, DC or RF plasma heating, or RF (radio frequency) induction heating, or electrical spot welding as illustrated in FIGS. 5-7. Alternative methods of preparing such a protrusion feature illustrated in FIG. 1(*a*) are not excluded, for example, a nearly parallel array of vertical wires or microwires of Ti (or other metals and alloys comprising Zr, Hf, Nb, Ta, Mo, W) can be brought down simultaneously and in a parallel manner onto the Ti implant substrate for physical contacts, the tips in contact with the substrate are electric-arc-bonded, then the extra length of the wires are sheared off to leave a forest of short wires attached onto the substrate.

Another alternative process consists of simple dropping of micro or macro fibers of Ti (or Ti-alloy, stainless steel or other biocompatible metallic materials, as described herein) onto the implant surface, and bond them onto the implant surface under compression, e.g., by utilizing electric arc spot welding or heating to high temperature for diffusion bonding. Such bonding processes for loose Ti fibers can be done even on a non-flat implant surfaces by utilizing mechanically adaptive compression unit. For heating and diffusion bonding of Ti and related metals or alloys onto the implant surface; exemplary heat treating atmosphere are either inert or reducing atmosphere, such as Ar, He, or $H_2$ containing gas atmosphere, or vacuum atmosphere.

The implants with the bonded protruding features of FIG. 1 (e.g., Ti implant with bonded, protruding Ti mesh screen) are then electrochemically anodized to produce a surface $TiO_2$ nanotube array structure to impart accelerated cell- or bone-growth characteristics on the surface of the protruding structure as well as the surface of the base implant material.

The implants with the protruding structure is then optionally heat treated to convert the generally amorphous $TiO_2$ material into a crystalline phase can be into the anatase $TiO_2$ phase, but not excluding other phases such as the rutile phase. The desired heat treatment conditions including annealing at 350-600° C. for 0.1-10 hr, or in another aspect, 450-550° C. for 0.5-5 hr. The heating rate has to be carefully chosen as slower than 5° C./hr so that crumbling of the crystallizing phase is prevented. Such a heat treatment also relieves much of the mechanical residual stresses that might have been introduced during the bonding of the protruding structure, thus improving the fracture toughness and fatigue life of the bone or teeth implants.

The desired diameter of the wires composing the protruding structure can in one aspect be in the range of 10-10,000 micrometers, or in another aspect, in the range of 25-500 micrometers. The desired thickness of the protruding structure depends on specific applications and the average diameter of the wires or fibers involved. In one aspect, the desired overall thickness of the protruding structure layer is 0.01-10 mm, or in another aspect, 0.05-2 mm.

Shown schematically in FIG. 1(*b*) is the locked-in bone growth around the protruding, hairy or mesh screen Ti with $TiO_2$ nanotube array surface structure for accelerated cell- or bone-growth characteristic. Such a mechanically locked-in composite structure of the grown bone together with the embedded implant protrusion ensures that the grown bone is strongly bonded onto the base implant surface with a drastically minimized possibility of undesirable interface separation at the hard-tissue/implant interface.

Figure 2:
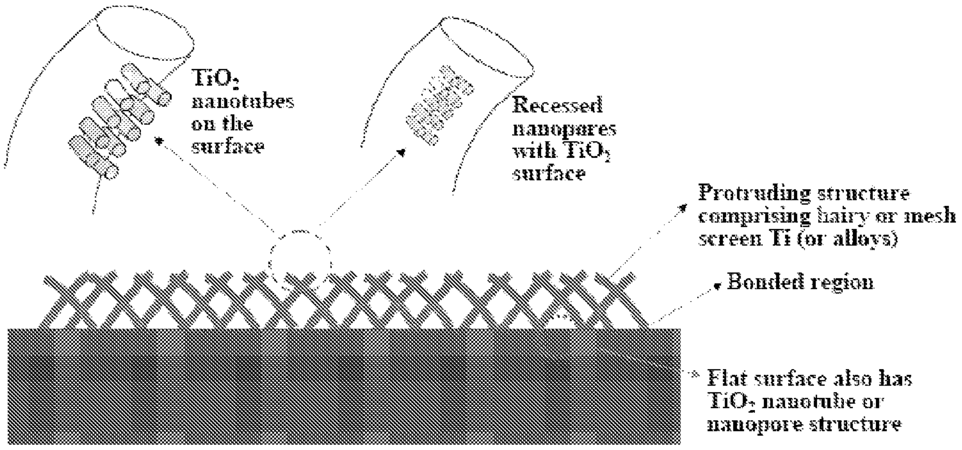
FIG. 2 illustrates exemplary $TiO_2$ nanotube or nanopore arrays on the surfaces of protruding hairy-shaped or mesh-screen-shaped Ti elements bonded onto the Ti implant surface; and optionally the biological agents can be stored in the nanotubes or nanopores for growth factor, drug delivery, etc. The bonded regions of the protruding structures are illustrated.

The drawing in FIG. 2 shows an enlarged view of the FIG. 1 drawing. It illustrates $TiO_2$ nanotube or nanopore arrays formed on the surfaces of hairy-shaped or mesh-screen-shaped, protruding Ti elements bonded onto the Ti implant surface. The $TiO_2$ nanotube or nanopore arrays can be formed using anodization processes described earlier, for example, see the article by S. Oh et al., "Growth of Nano-scale Hydroxyapatite Using Chemically Treated Titanium Oxide Nanotubes", *Biomaterials* (2005) 26:4938-4943, and "Significantly Accelerated Osteoblast Cell Growth on Aligned $TiO_2$ Nanotubes", *Journal of Biomedical Materials Research* (2006) 78A:97-103.

In one aspect, the pore spaces in the $TiO_2$ nanotubes or nanopores illustrated in FIG. 2 can be utilized to store desirable biological agents such as biomolecular growth factors like BMP (bone morphogenetic protein) or collagens, antibiotics, drug molecules, inorganic nanoparticles, etc. for steadily and passive supply to the in-vivo or in-vitro environment for further accelerated cell/bone growth or for medical therapeutics. The active, on-demand drug delivery utilizing a combination of such nanotubes/nanopores and inserted magnetic particles will be describes later as a separate embodiment section.

Figure 3:
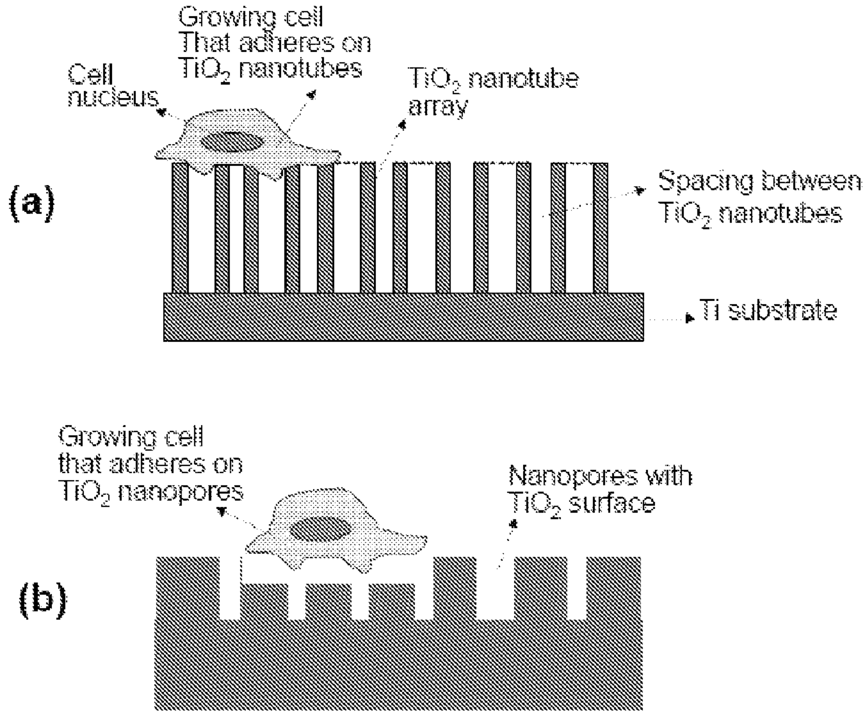
FIG. 3 schematically illustrates exemplary self-organized $TiO_2$ nanotube arrays grown on titanium substrate, which accelerates cell proliferation, e.g., as in accelerated cell proliferation on exemplary $TiO_2$ nanotubes or nanopores.

The $TiO_2$ nanotube arrays or nanopore arrays grown on titanium substrate by anodization and other processes significantly enhance cell adhesion, and accelerate cell proliferation as illustrated in FIG. 3. A part of the reasons for such accelerated bio activity appears to be the enhanced adhesion of the growing cell front (filopodia) into the $TiO_2$ nanopores at the early stage of cell growth and proliferation. See the article by S. Oh et al., "Significantly Accelerated Osteoblast Cell Growth on Aligned $TiO_2$ Nanotubes", *Journal of Biomedical Materials Research* (2006) 78A:97-103.

Figure 4:
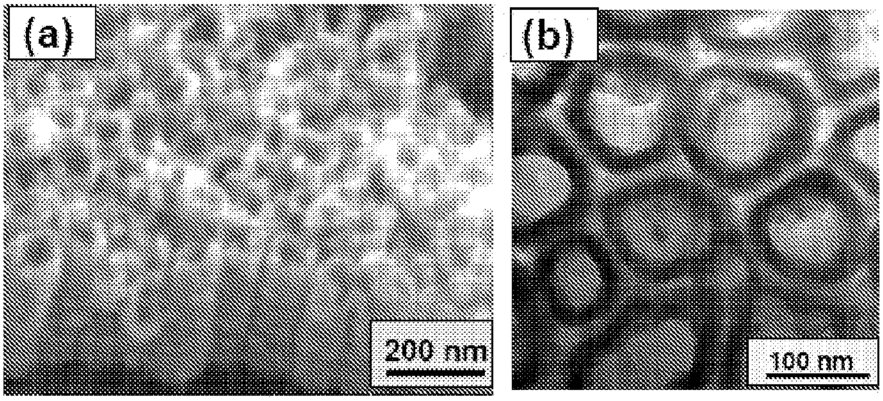
FIG. 4 illustrates pictures of an exemplary microstructure of the vertically aligned $TiO_2$ nanotubes on titanium substrate, as illustrated by FIG. 4(*a*) scanning electron microscope (SEM) micrograph, FIG. 4(*b*) cross-sectional transmission electron microscope (TEM) micrograph.

The invention provides structures having a secure mechanical lock-in for growing cells or bones relative to the implant surface due to the presence of the protruding structures, e.g., in the bioimplants of the invention. A secure attachment ensures continued proliferation and integration of healthy cells or bones. Depicted in FIG. 4 are the exemplary microstructures of the vertically aligned $TiO_2$ nanotubes on the protruding Ti wire or mesh screen structure as well as the titanium substrate itself. The microstructure of FIG. 4(*a*) represents a scanning electron microscope (SEM) micrograph of the $TiO_2$ nanotube arrays, while FIG. 4(*b*) represents a cross-sectional transmission electron microscope (TEM) micrograph of the $TiO_2$ nanotube arrays.

An exemplary process of the invention is to attach the protruding Ti structures in FIG. 1(*a*) and FIG. 2 to the Ti implant base to utilize a process of diffusional bonding as illustrated in FIG. 5. While diffusional bonding can be carried by simple contact and heating of two metals under compression, the invention calls for an addition of physical vapor deposited metal to enhance the diffusional bond strength. This exemplary process sequence, as illustrated in FIG. 5, can comprise five basic steps:

i) Step 1—The protruding structure of hairy Ti or mesh-screen Ti is first prepared as a layer material and cut to pieces that match the size of the Ti implant base. The protruding structure is then placed on top of the implant base as illustrated in FIG. 5(*a*). The protruding structure is urged to physically contact the surface of the implant base at as many contacts as possible by elastically compressing or gently clamping the mesh screen down during Ti thick film deposition, using a grid-shaped or a finger-shaped rod retainer structure (not shown in the figure). The rods in the retainer structure can comprise a surface oxidized, metal rod material, so that the retainer rods do not stick to the protruding mesh screen Ti structure during the subsequent diffusion bond process.

ii) Step 2—A thick film of Ti is then deposited onto the protruding structure and the implant base as illustrated in FIG. 5(*b*). The desired thickness of the Ti anchoring film is in the range of 100-2000 micrometer, which can be deposited either by physical vapor deposition such as sputtering or evaporation, or by chemical vapor deposition. In order to deposit the film relatively uniformly despite the interference of shadowing effect caused by the upper portion of the wire or mesh screen structure, a frequent rotation or tilting of the substrate during the film deposition in combination with an oblique incident deposition can be used. With regard to the choice of deposited film material, the use of the same material, e.g., Ti base protruding structure, Ti base implant, as well as Ti anchoring film can be used for ease and reliability of diffusional bonding without complications and unknowns, e.g., avoiding a possibility of forming a brittle intermetallic alloy compound. In addition to Ti, other alloys of Ti (such as Ti—Al—V), or any biocompatible metals or alloys such as Zr, Hf, Nb, Ta, Mo, W and their alloys, or stainless steels, may be utilized. Dissimilar metals or alloys, for example, bonding of stainless steel mesh screen on Ti implant using Ti film deposition, can also be used; in one aspect, appropriate precautions in the selection of the matching alloy composition and processing conditions can produce reliable bonding of the protruding structure.

iii) Step 3—The protruding structure and the base implant covered by deposited thin film is then subjected to a high temperature annealing for diffusional bonding of the Ti protruding structure onto the Ti implant, with the deposited thick film of Ti serving as the anchoring material, thus inducing a strong bonding attachment of the protruding structure onto the Ti implant base, as illustrated in FIG. 5(*c*). The desired diffusion annealing and bonding process includes heating and holding at a high temperature of between about 500 to 1300° C., or 500 to 1200° C., 500 to 1100° C., or 500 to 1000° C., for about 0.1 to 100 hrs, or in one aspect, in a reducing atmosphere (such as hydrogen-containing gas atmosphere) or an inert atmosphere (such as argon or helium atmosphere) to minimize oxidation of the Ti surface, which interferes with the intended metal diffusional bonding. In one aspect, furnace heating is used, and it can be simple, straightforward, and of low cost, however the use of other heating techniques such as induction heating, e-beam heating, laser heating, and torch heating for the diffusion bonding is not excluded.

iv) Step 4—The bonded structure is then subjected to the anodization process described earlier, so that both the surface of the Ti wire or mesh screen and the surface of the Ti implant base material are anodized to have $TiO_2$ nanotube or nanopore structure for accelerated cell- or bone-growth. The invention also provides alternative processes such as chemical etching, surface melt evaporation, plasma etching, etc, instead of anodizing, can also be utilized to induce the surface nanostructures of metallic or oxide nanopores, nanotubes, nanowires on the hairy or wire-mesh protrusion structure. The space within each of the nanotubes or nanopores can also be utilized to store biological agents such as growth factors, antibiotics, genes, DNAs, therapeutic drugs, metallic or magnetic nanoparticles, etc. to further accelerate the cell or bone growth, or to serve as an implanted medical therapeutic devices for applications such as cancer treatment.

v) Step 5—The anodized assembly is optionally heat treated, e.g., near the temperature of ~500° C. for 0.1-10 hrs to crystallize the nanotube and obtain a desirable crystal structure such as the anatase phase.

FIG. 6 illustrates another exemplary process of the invention comprising attaching the protruding Ti structures in FIG. 1(*a*) and FIG. 2, a non-contact heating process, to the Ti implant base is to utilize a process of melt bonding as illustrated in the figure. The expression "melt-bonding" used here is defined as having a broad meaning, which includes high temperature diffusion bonding as a result of such non-contact heating even if the overall metal temperature remains below the melting point of the hose substrate metal surface or the wire mesh metal and hence no melting occurs in a strict sense. This exemplary process of the inventive, comprising melt bonding for biomaterials fabrication, can comprise four steps:

i) Step 1—The protruding structure of hairy Ti or mesh-screen Ti in the overall form of a layer material is cut to pieces that match the size of the Ti implant base, and is placed on top of the implant base as illustrated in FIG. 6(*a*). The structure is urged to physically contact the surface of the implant base at as many contacts as possible by elastically compressing or gently clamping the mesh screen down using a grid-shaped or a finger-shaped rod retainer structure (not shown in the figure). The rods in the retainer structure can comprise a surface oxidized, metal rod material so that they do not melt and stick to the protruding mesh screen Ti structure during the subsequent melt-bonding heating process of FIG. 6(*a*).

ii) Step 2—This assembly structure is then subjected to the melt-bonding process to attach the protruding structure to the implant base, as illustrated in FIG. 6(*b*). The heating process can be carried out in vacuum, inert atmosphere (e.g., using Ar or He) or in a reducing atmosphere (e.g., using hydrogen gas or a mixture of hydrogen and other inert gases). Exemplary heating methods include induction heating using RF electromagnetic field, e-beam heating, laser heating, torch heating, and furnace heating. Other methods of heating are not excluded. With regard to the choice of materials involved, the use of the same material, e.g., Ti base protruding structure and Ti base implant can be used for ease and reliability of melt-bonding associated with the use of the same material. In addition to Ti, other alloys of Ti (such as Ti—Al—V), or any biocompatible metals or alloys of Zr, Hf, Nb, Ta, Mo, W, or stainless steels, may be utilized. Dissimilar metals or alloys, for example, melt-bonding of stainless steel mesh screen on Ti implant, can also be used since appropriate precautions in the selection of the matching alloy composition and processing conditions can produce reliable bonding of the protruding structure. The protruding structure and/or the Ti implant base are heated to a sufficiently high temperature so that there is local surface melting (or surface softening and diffusion bonding), for example, heating to a surface temperature of 800-2000° C. for a general duration in the range of about 0.01-100 minutes, or in another aspect, 0.1-10 minutes.

iii) Step 3—After the melt-bonding, the assembled structure is subjected to the anodization process described earlier, so that both the surface of the Ti wire or mesh screen and the surface of the Ti implant base material are anodized to have $TiO_2$ nanotube or nanopore structure for accelerated cell- or bone-growth as indicated in FIG. 6(*c*) and (d). Other alternative processes such as chemical etching, surface melt evaporation, plasma etching, etc, instead of anodizing, can also be utilized to induce the surface nanostructures of metallic or oxide nanopores, nanotubes, nanowires on the hairy or wire-mesh protrusion structure, and hence the use of such alternative processes is not excluded. The space within each of the nanotubes or nanopores can optionally be utilized to store biological agents such as growth factors, antibiotics, genes, DNAs, therapeutic drugs, metallic or magnetic nanoparticles, etc. to further accelerate the cell or bone growth, or to serve as an implanted therapeutic medical treatment device.

iv) Step 4—The anodized assembly is optionally heat treated, e.g., near the temperature of ~500° C. for 0.1-10 hrs to crystallize the nanotube and obtain a desirable crystal structure such as the anatase phase.

FIG. 7 schematically shows an alternative exemplary method of the invention comprising strongly bonding the protruding structure to the implant base by spot welding. The protruding structure can be hairy-shaped, fiber-shaped or mesh-screen-shaped Ti. Other similarly biocompatible Ti-base alloys (e.g., Ti—Al—V alloys) or other refractory metals (e.g., Zr, Hf, Nb, Ta, Mo, W and their alloys), or stainless steels can also be used for the protruding structure as well as for the implant base.

The process of spot welding is well established in the engineering field. It is a type of resistance welding used to attach thin pieces of metal or alloy parts. It uses two large electrodes which are placed on either side of the surface to be welded, and passes A large electrical current is passed through the metal parts involved and heats up the metal contact area The degree of heating near the contact area is determined by the amplitude and duration of the current used. Metals with higher electrical and thermal conductivity generally require larger electrical currents to obtain a comparable heating effect.

As the contact of the hairy or mesh-screen protruding structure with the base implant occurs at isolated spots, the spot welding is an efficient approach of bonding such a structure. Referring to FIG. 7(*a*), one of the spot welding electrode is placed underneath the implant base material while the upper electrode compresses down on the protruding structure as illustrated in FIG. 7(*a*). The shape of the spot welding upper electrode can be a disk, plate, grid, vertical rod array, or frame. A disk- or plate-shaped electrode contacts and presses down on most of the top portion of the hairy or mesh-screen shaped protruding structure. Alternatively, if the mesh screen is highly porous, a finger-shape (a vertical rod array) or linear grid-shape electrode can be prepared and inserted into the middle or lower portion of the mesh screen. The duration of spot welding can be in the range of about 0.1 to 5 seconds. The spot welding process can be repeated if necessary, either on the same spot or at nearby different spots.

In one aspect of the invention, the electrode materials (both the upper and lower electrodes) have to be carefully selected in order to avoid contamination by the commonly used electrode material such as a Cu electrode, the surface of which can be locally melted and alloyed onto the surface of the Ti implant and the Ti protruding structure during spot welding. As copper is not necessarily considered a fully biocompatible material, the invention calls for a preferable selection of the electrode material (at least near the electrode surface), among high electrical conductivity noble metals and alloys such as Au, Pt, Pd, and their alloys. The use of Ti, W, or other refractory metal electrodes is not excluded.

After the spot welding is carried out, FIG. 7(*b*), the assembled structure is optionally subjected to the anodization process as described earlier, so that both the surface of the Ti wire or mesh screen and the surface of the Ti implant base material are anodized to have $TiO_2$ nanotube or nanopore structure for accelerated cell- or bone-growth as indicated in FIGS. 7(*c*) and (*d*). The space within each of the nanotubes or nanopores can optionally be utilized to store biological agents such as growth factors, antibiotics, genes, DNAs, therapeutic drugs, metallic or magnetic nanoparticles, etc. to further accelerate the cell or bone growth, or to serve as an implanted therapeutic medical treatment device.

Figure 8:
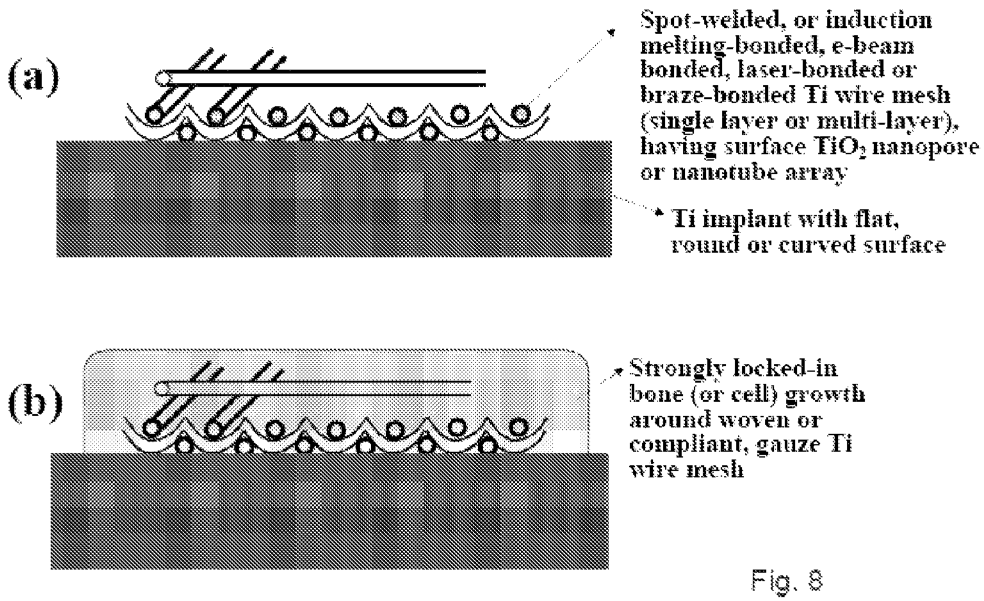
FIG. 8 schematically illustrates a side view of an exemplary hairy or wire-mesh Ti (or alloy), or an exemplary biocompatible alloy such as stainless steel, attached onto Ti implant surface for enhanced toughness, strength, and mechanical locking of bone growth around implant.

FIG. 8(*a*) schematically illustrates a side view of an exemplary hairy or wire-mesh-screen Ti (or alloy), or any biocompatible alloy such as stainless steel, attached onto Ti implant surface for enhanced toughness, strength, and mechanical locking of bone growth around implant. The spot-welded, induction melting-bonded, DC or AC plasma bonded, e-beam bonded, laser-bonded or braze-bonded Ti wire mesh (single layer or multi-layer), having surface $TiO_2$ nanopore or nanotube array, enables strongly locked-in bone (or cell) growth around wire-shape or mesh-screen shape Ti wires as illustrated in FIG. 8(*b*), at the same time allowing accelerated bone or cell-growth due to the presence of surface nanostructure.

Figure 9:
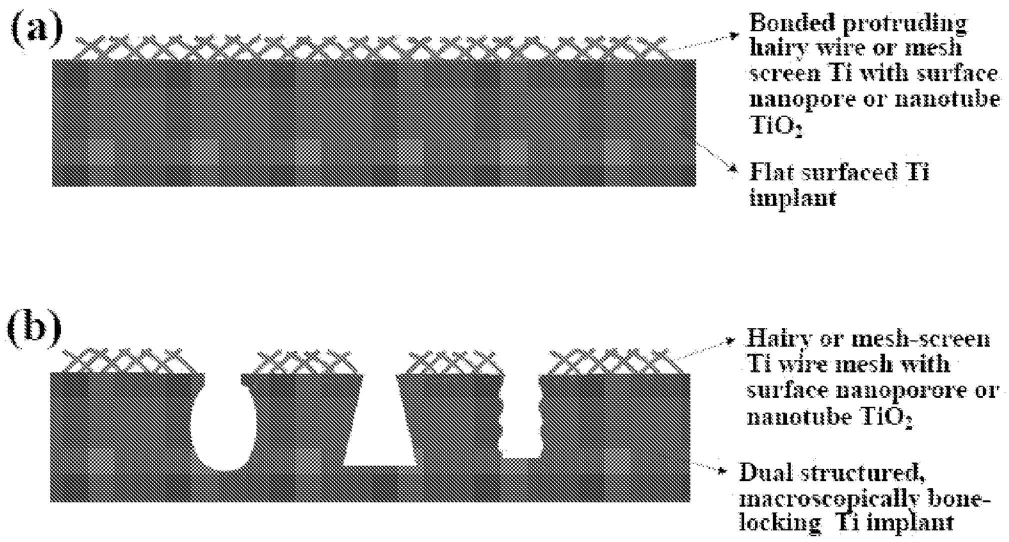
FIG. 9 schematically illustrates an exemplary flat Ti implant vs dual-structured, bone-locking Ti implant with attached hairy Ti or Ti mesh screen to further enhanced, local adhesion and mechanical locking.

The mechanical bond strength between a growing hard tissue (e.g., bone) and the implant material with protruding structure can further be improved by introducing a dual-structured, bone-locking Ti implant containing recessed cavities, especially those having re-entrant shaped cavities as illustrated in FIG. 9. These cavities have macroscale dimensions with the diameter and depth being in the size range of 10-5000 micrometers, or in another aspect, 25-500, and exhibit a desirable bone lock-in structure. These cavities can be formed by photolithography, shadow-mask lithography, or various other non-conventional lithography techniques followed by chemical etching.

Figure 10:
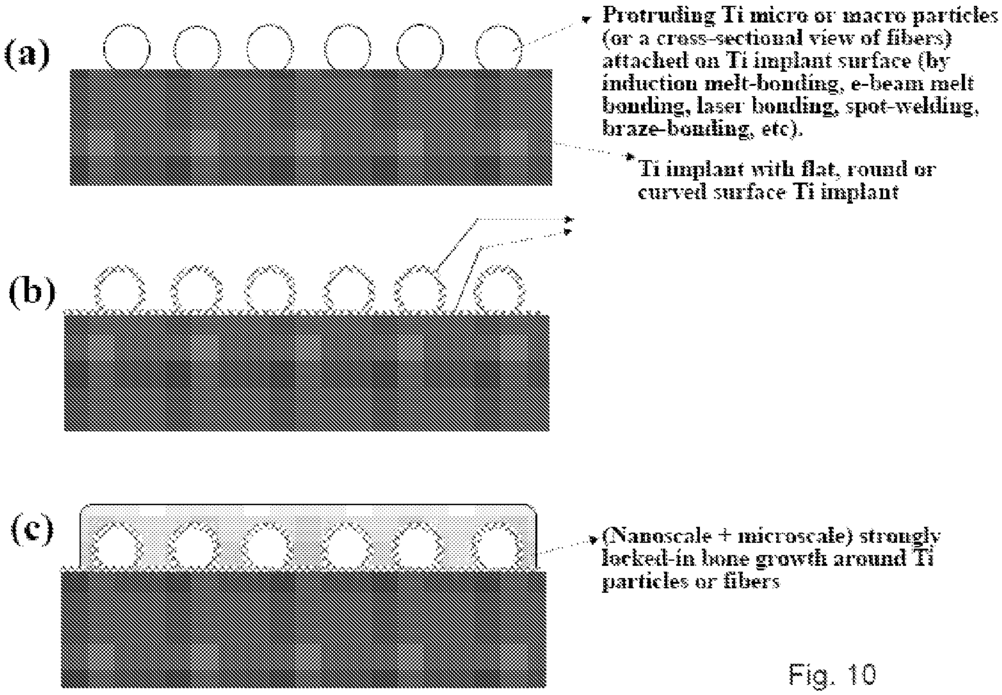
FIG. 10 illustrates an exemplary monolayered Ti (or alloy) particles or fiber arrays attached onto Ti implant surface for enhanced toughness, strength, and mechanical locking of bone growth around the particles.
Figure 11:
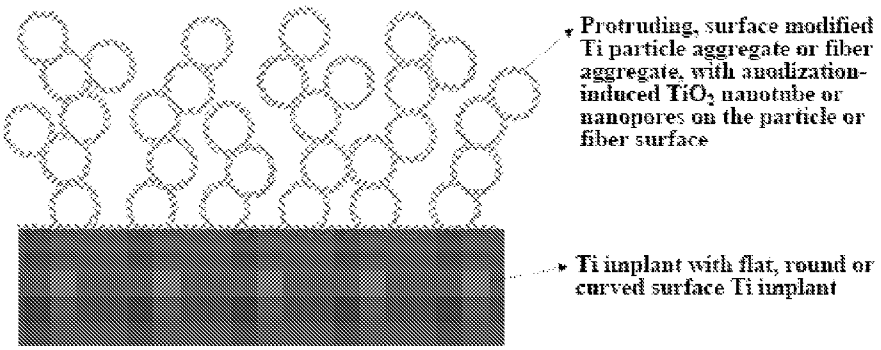
FIG. 11 illustrates an exemplary Ti (or alloy) particle or fiber aggregate sintered and attached onto Ti implant surface for enhanced toughness, strength, and mechanical locking of bone growth around the particle aggregate; protruding, surface modified Ti particle aggregate or fiber aggregate, with anodization-induced TiO2 nanotube or nanopores on the particle or fiber surface is shown on an exemplary Ti implant with flat, round or curved surface Ti implant.

FIG. 10 illustrates, instead of wire-based protruding structures, exemplary horizontally placed Ti (or alloy) particles (near spherical or short fiber shape) attached onto Ti implant surface serve as protruding structures in this exemplary structure of the invention. The particles can be in a monolayer configuration as illustrated in FIG. 10 or a three dimensionally-connected configuration as illustrated in FIG. 11. In one aspect, these particle or fiber aggregate structures attached onto Ti implant surface can provide enhanced toughness, strength, and mechanical locking of bone growth around the particle or fiber aggregate.

The particle shape is arbitrarily defined here as a near-spherical object with an aspect ratio of less than 2 and having regular or irregular surface. The fiber shape is arbitrarily defined here as an elongated object with an aspect ratio of at least 2 and having regular or irregular surface, straight or bent configuration. The protruding Ti micro/macro particles or fibers as shown in FIG. 10 can be attached onto the Ti implant surface by processing approaches involving induction melt-bonding, e-beam melt bonding, laser bonding, spot-welding, or diffusion-bonding.

The material for these micro/macro particles can be Ti or Ti-base alloys (e.g., Ti—Al—V alloys), other refractory metals (e.g., Zr, Hf, Ta, W and their alloys), or stainless steels can also be used for the protruding structure as well as for the implant base. The desired diameter of the micro/macro particles or fibers in FIG. 10 and FIG. 11 composing the protruding structure is in the range of 10-10,000 micrometers, or in another aspect, in the range of 25-500 micrometers. The desired thickness of the protruding structure depends on specific applications and the average diameter of the particles or fibers involved. In one aspect, the desired overall thickness of the protruding structure layer is 0.01-10 mm, or in another aspect, 0.05-2 mm.

An exemplary process of fabricating such a structure is described as follows.

i) The particles or fibers made of Ti or Ti alloys, or other biocompatible metals or alloys are prepared or procured, and then are placed on the top surface of the implant base structure.

ii) One alternative method of fabricating the protruding structure of FIG. 10 or FIG. 11 comprising particle or fiber aggregate structure is a simple dropping of the Ti or alloy powders or fibers on the Ti implant surface and sintering at a high temperature in the range of between about 500 to 1000° C., or about 500 to 1100° C., or about 500 to 1200° C., for an exemplary duration of between about 0.1 to 10 hrs, in an inert, vacuum, or reducing gas atmosphere. Ar, He or nitrogen gas can be used for inert gas heat treatment while hydrogen, forming gas (in one aspect, about 1 to 15% mixture of $H_2$ in $N_2$ or Ar gas), or ammonia gas can be used for reducing atmosphere heat treatment. Alternatively, instead of sintering, such a pile of Ti (or Ti alloy) powders or fibers can be spot welded under compression to attach the particles or fibers among themselves and to the surface of the Ti implant base. Such a spot welding is especially desirable from the practical point of view as the process is fast and convenient since the complicated step of heat treatment to bond loose powders or fibers is avoided.

iii) After the protruding structure composing of these particle or fiber aggregate layer is attached onto the Ti base implants, the assembly is subjected to the anodization process described earlier, so that both the surface of the Ti wire or mesh screen and the surface of the Ti implant base material are anodized to have $TiO_2$ nanotube or nanopore structure for accelerated cell- or bone-growth as indicated in FIG. 6(*c*) and (d). Other alternative processes such as chemical etching, surface melt evaporation, plasma etching, etc, instead of anodizing, can also be utilized to induce the surface nanostructures of metallic or oxide nanopores, nanotubes, nanowires on the hairy or wire-mesh protrusion structure.

iv) The assembly is optionally heat treated, e.g., near the temperature of ~500° C. for 0.1-10 hrs to crystallize the nanotube and obtain a desirable crystal structure such as the anatase phase. The space within each of the nanotubes or nanopores can optionally be utilized to store biological agents such as growth factors, antibiotics, genes, DNAs, therapeutic drugs, metallic or magnetic nanoparticles, etc. to further accelerate the cell or bone growth, or to serve as an implanted therapeutic medical treatment device as described below.

2. Externally and Remotely Controllable Drug-Delivery Systems

The invention also provides externally controllable drug-delivery systems comprising metallic, ceramic or polymeric materials, and methods for operating such systems, an exemplary embodiment being a structure of magnetic nanoparticles inserted together with drugs or biological agents into nanopores/micropores or into the gaps in nanowire/microwire arrays or nano-ribbon/micro-ribbon arrays, or a structure consisting of magnetic wire array or ribbon array.

Figure 12:
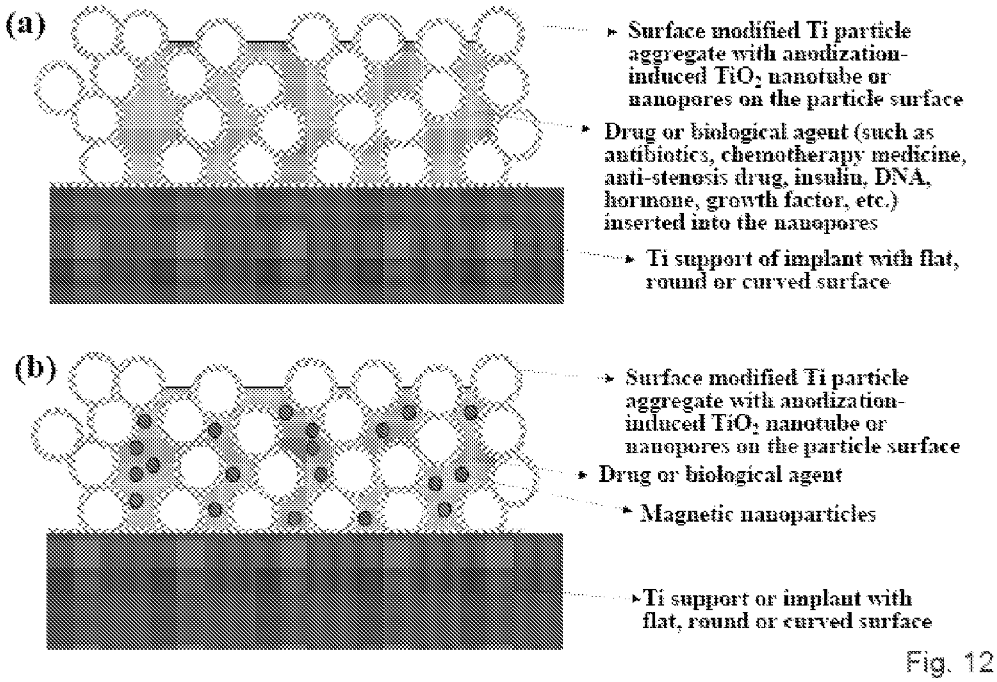
FIG. 12 schematically illustrates an exemplary magnetic remote controllable drug delivery system based on densely spaced Ti particles or wire mesh screen bonded onto Ti implant surface or any material surface, such as metal, ceramic or polymer.

This aspect of the invention can comprise structures as described, e.g., in PCT Patent Application no. PCT/US2006/016471, filed on Apr. 28, 2006, Jin et al., e.g., can incorporate a drug delivery system utilizing a $TiO_2$ nanotube arrays, e.g., as described in Jin et al. This invention provides drug delivery systems, either passive or active, remote-actuated, on/off controllable and programmable drug delivery systems comprising various nanopore structures (non-$TiO_2$-nanotube-based). FIG. 12 schematically illustrates exemplary drug delivery systems of the invention. The schematics shown in FIG. 12(*a*) describe passive, diffusion based, slow drug release device. The drawing in FIG. 12(*b*) illustrates an active, remotely and externally controllable, drug release device which is an on-command, drug delivery system.

In one aspect of the invention, densely spaced Ti particles, fibers or wire arrays are attached onto Ti implant surface by utilizing various processing methods such as diffusion bonding, melt-bonding by rapid heating with laser, electron beam, RF or induction field, DC or Ac plasma or spot welding to introduce a microporous structure for use as the basis of a drug delivery reservoir. The implant base mostly serves as a biocompatible carrier of the microporous structure although some of its own surface areas also serve to store and release drugs. The drugs or biological agents to be stored and released in a controlled manner in this invention include pharmaceutical therapeutic drugs such as antibiotics, chemotherapy medicine, anti-stenosis drug, insulin, and biologically active agents such as DNAs, genes, proteins, hormones, collagens and other growth factors, magnetic nanoparticles, infraredlight-absorbing nanoparticles, etc. Both the particles/fibers and the implant base material can be made of biocompatible metals or alloys such as Ti based alloys, or other refractory based metals and alloys, or stainless steel. The surface of the implant base can have flat, round or curved surface depending on specific applications.

The surface of each particle or fiber in the microporous aggregate is then further modified with anodization-induced $TiO_2$ nanotube or nanopores as illustrated in FIG. 12(*a*). The process of anodizing Ti surface to prepare $TiO_2$ nanotube arrays is well established. See articles by B. B. Lakshmi, et al., *Chemistry of Materials* (1997) 9:2544-2550, by Miao, et al., *Nano Letters* (2002) 2(7):717-720, by Gong, et al., *Journal of Materials Research* (2001) 16(12):3331-3334, by J. M. Macak, et al., *Angew. Chem. Int. Ed.* (2005) 44:7463-7465, *Electrochimica Acta* (2005) 50:3679-3684, and *Angew. Chem. Int. Ed.* (2005) 44:2100-2102, by A. Ghicov, et al., *Electrochemistry Communications* (2005) 7:505-509, by S. Oh et al., "Growth of Nano-scale Hydroxyapatite Using Chemically Treated Titanium Oxide Nanotubes", *Biomaterials* (2005) 26:4938-4943, and "Significantly Accelerated Osteoblast Cell Growth on Aligned $TiO_2$ Nanotubes", *Journal of Biomedical Materials Research* (2006) 78A:97-103.

For anodization, in one aspect, fluorine containing chemicals are utilized as an electrolyte, and a voltage of 10-25 volts is applied. The concentration of electrolytes has to be carefully chosen, as reported in articles by Gong, et al., Oh, et al., Macak, et al., and Ghicov, et al. mentioned above. Some exemplary electrolytes and their concentrations are; 0.5 wt % hydrofluoric acid (HF) in water, 0.5 wt. % ammonium fluoride ($NH_4F$) in 1 M ammonium sulphate ($(NH_4)_2SO_4$), and 1 wt. % NaF in 1M $Na_2SO_4$ solution. Various anodization processing parameters such as the applied voltage, reaction time, the pH and the temperature of the bath, etc. have to controlled and optimized as well.

The anodized nanopores in these structures, in combination with the micropore base structure, allow a storage of any desired drugs and biological agents, and their slow, diffusion-based release. Such a structure constitutes the basis of an efficient, biocompatible, time-controlled drug delivery system for pharmaceutical therapeutic drugs such as antibiotics, chemotherapy medicine, anti-stenosis drug, insulin, and biologically active agents such as DNAs, genes, proteins, hormones, collagens and other growth factors, magnetic nanoparticles, infrared-light-absorbing nanoparticles, etc.

The desired dimension of the particle/fiber aggregate porous structure of FIG. 12(*a*) is as follows. The average diameter of the particles or fibers can be in the range of about 1-1000 micrometers, or in another aspect, 10-250 micrometers. The average diameter of the pores is in the range of about 0.1-100 micrometers. The desired pore volume in the aggregate structure is at least 20%, or in another aspect, at least 50%. The overall thickness of the aggregate structure attached onto the implant base is in the range of about 10-10,000 micrometers, or in another aspect, 100-2500 micrometers. The diameter of the nanopores in anodized $TiO_2$ nanotubes or nanopores is in the range of about 20-500 nm, and the depth of the nanopores (or the height of the nanotubes) is in the range of about 100-10,000 nm.

The insertion of drugs can be in an aqueous liquid form; insertion into nanopores can be difficult because of the surface tension of the liquid involved and the trapped air within the nanopores which tends to block the incoming liquid. While a long-time immersion (e.g., 10-100 hrs) of the porous aggregate of FIG. 12(*a*) in a pool of liquid containing the desired drug is helpful for inserting the drug or biological agent liquid into the nanopores, this invention calls for a unconventional approaches to ensure efficient insertion of drugs or biological agents into the nanopores.

(a) Use of supercritical $CO_2$ deposition technique—Supercritical carbon dioxide ($scCO_2$) exhibits a novel hybrid characteristics of liquid-like and also vapor-like properties. Like a liquid, it can dissolve solutes, e.g., some drugs in the present invention. Like a vapor, it possesses low viscosity, high diffusivity and negligible surface tension, so it can deliver chemicals and drugs into nanoscale cavities or high-aspect-ratio nanopores. Examples of $scCO_2$ processing to deliver materials into small nanopores are described, for example, in articles by Ye et al., Xiang-Rong Ye, Yuehe Lin, Chongming Wang, Chien M. Wai, *Adv. Mater.* (2003) 15:316, and Xiang-Rong Ye, Yuehe Lin, Chongming Wang, M. H. Engelhard, Chien M. Wai, *J. Mater. Chem.* (2004) 14:908.

(b) Use of vacuum or boiling water process—Often the trapped air inside nanopores or micropores can prevent the insertion of drug-containing aqueous solution. In this invention, vacuum (such as $10^{-4}$-$10^{-6}$ torr level vacuum obtained by pumping a chamber using a mechanical pump, diffusion pump, cryopump, or turbo pump) can be used to remove the trapped air prior to letting the drug-containing aqueous solution into the chamber and hence inside the nanopores or micropores of FIG. 12(*a*) type drug delivery reservoir material placed in the chamber. Another technique utilized in this invention is to place the drug delivery reservoir material inside a drug-containing aqueous solution, and boil the solution so that the trapped air from the nanopores is removed and the solution gets inside the nanopores. This technique is of course suitable only when the drug or biological agents to be inserted does not get damaged on exposure to the boiling temperature.

(c) Use of pressure injection process—A liquid containing the drug, biological agent or magnetic nanoparticles can be loaded into the nanopores or micropores by using high pressure injection or infiltration technique.

The speed of the drug release is controlled/programmed by design of the micro particle aggregate structure and the $TiO_2$ nanotube type nanostructure. In this invention, two major materials parameters are controlled to optimize the drug release rate.

i) The volume fraction and diameter of the Ti micro particles or fibers in the aggregate, and hence the size, the lengths of the micropores and volume fraction of the micropores between the microparticles, and ii) The diameter, spacing and depth of the $TiO_2$ nanotubes on the surface of each of the micro particles or micro fibers, within which the drugs or biological agents are stored. These dimensions dictate the overall diffusion distance and time required for the released drug to reach the surface of the particle/fiber aggregate to become available for in-vivo bio interactions or chemical reactions.

Referring again to FIG. 12(*b*), the device illustrates an active, remotely and externally controllable, drug release device operated by applied magnetic field. In one aspect of the invention, the drugs or biological agents to be stored and released such as pharmaceutical therapeutic drugs (such as antibiotics, chemotherapy medicine, anti-stenosis drug, insulin), and biologically active agents (such as DNAs, genes, proteins, hormones, collagens and other growth factors) are inserted into the micropore or nanopore reservoirs in FIG. 12(*b*) type structures together with magnetic nanoparticles. The drugs or biological agents can be dissolved in liquid or contained as a colloidal suspension mixture. Various techniques including soaking in drug-containing liquid, supercritical $CO_2$ processing, vacuum suction, pressure injection, boiling water processing, etc. can be utilized for the insertion.

In one aspect, the invention provides an on-command, drug delivery system. The exemplary device of FIG. 12(*b*) requires the incorporation of magnetic nanoparticles such as biocompatible $Fe_3O_4$ (magnetite) or $Fe_2O_3$ (maghemite) nanoparticles with an average diameter in the range of about, e.g., 2-50 nm, or in another aspect, 5-20 nm. These magnetic particles can be magnetically moved or vibrated utilizing a DC magnetic field (or very low frequency ac field) with time-dependent changing field directions to allow the movement and release of the drug-containing solution from the nanopore or micropore reservoir which, in the absence of such magnetic stimulation, tends to be retained within the nanopores or micropores by capillary confinement.

An alternative embodiment is that instead of movement of magnetic particles, they can be stationary, but can be selectively heated by external ac magnetic field, e.g., at ~100 KHz, which also selectively heats up the drug-containing aqueous solution nearby. Magnetic particles have been used for local heating, for example for in-vivo magnetic hyperthermia treatment of cancer; or as described in, e.g., Pankhurst et al., *Journal of Physics D: Appl. Phys*. (2003) 36: R167-R181; Tartaj, et al., *Journal of Physics D: Appl. Phys*. (2003) 36:R182-R197; PCT/US04/043459, filed on Dec., 23, 2004, Jin, et al.

The heated drug-containing solution in the nanopore or micropore reservoir is then diffused out at an accelerated pace. In one aspect of the invention, these magnetically remote-controllable drug release device can be basically turned on or turned off at will by switching on/off of the applied magnetic field. Another advantageous characteristics of the inventive magnetic drug release device is a quantitatively control of the amount of the drug released by the duration and the number of repeated cycles of magnetic heating operations actuated by externally applied magnetic field.

Figure 13:
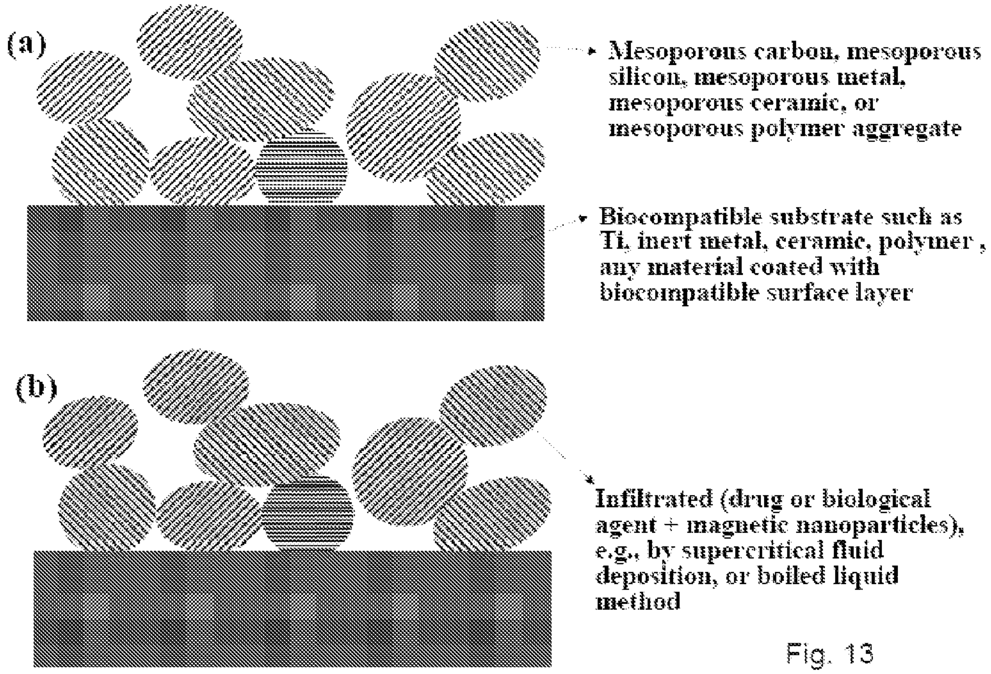
FIG. 13 schematically depicts an exemplary magnetic remote controllable drug delivery system based on mesoporous aggregate material filled with magnetic nanoparticles.

FIG. 13 schematically illustrates another embodiment of the inventive, remote-controllable, on-command drug delivery system. Here, a mesoporous aggregate material filled with magnetic nanoparticles are utilized as the reservoir for storage of drugs or biological agents. First, mesoporous aggregate material is attached onto a substrate or support material which can be selected from biocompatible material such as Ti, noble metal, ceramic, polymer, or any material coated with biocompatible surface layer. This is schematically illustrated in FIG. 13(*a*). The attachment can be accomplished by, e.g., diffusion bonding, melt-bonding, adhesive bonding, etc. Examples of mesoporous aggregate materials useful for this embodiment of the invention include mesoporous carbon, mesoporous silicon, mesoporous metal, mesoporous ceramic, or mesoporous polymer aggregates. Exemplary size of the magnetic nanoparticles can in one aspect be in the range of about 5-20 nm. The typical desired diameters in the mesoporous aggregate to store the drugs or biological agents together with magnetic nanoparticles, is in the range of about 5-500 nm, or in another aspect, 5-100 nm.

An aqueous solution of drugs or biological agents, together with magnetic nanoparticles is then infiltrated into the nanopores or micropores in the mesoporous aggregate using the techniques described earlier, i.e., supercritical $CO_2$ infiltration technique, vacuum suction, pressure injection, or boiling water technique. Such mesoporous aggregate containing drugs or biological agents, together with magnetic nanoparticles is illustrated in FIG. 13(*b*). The magnetic particles in the nanopores or micropores of the mesoporous aggregate can be magnetically moved or vibrated utilizing a DC magnetic field (or very low frequency ac field) with time-dependent changing field directions to allow the movement and release of the drug-containing solution from the nanopore or micropore reservoir which, in the absence of such magnetic stimulation, tends to be retained within the nanopores or micropores by capillary confinement.

In one aspect, instead of movement of magnetic particles to release the drug, the magnetic nanoparticles are heated to initiate the drug release. The magnetic particles can be selectively heated by external ac magnetic field, e.g., at ~100 KHz, which also selectively heats up the drug-containing aqueous solution nearby. The heated drug-containing solution in the nanopore or micropore reservoir of the mesoporous aggregate is then diffused out at an accelerated pace. In one aspect, these magnetically remote-controllable drug release device can be basically turned on or turned off at will by switching on/off of the applied magnetic field. Alternative characteristics of the inventive comprise a magnetic drug release device having the ability to release a quantitatively controlled amount of the drug by the duration and the number of repeated magnetic heating cycles applied to the in-vivo drug reservoir using external applied field.

Figure 14:
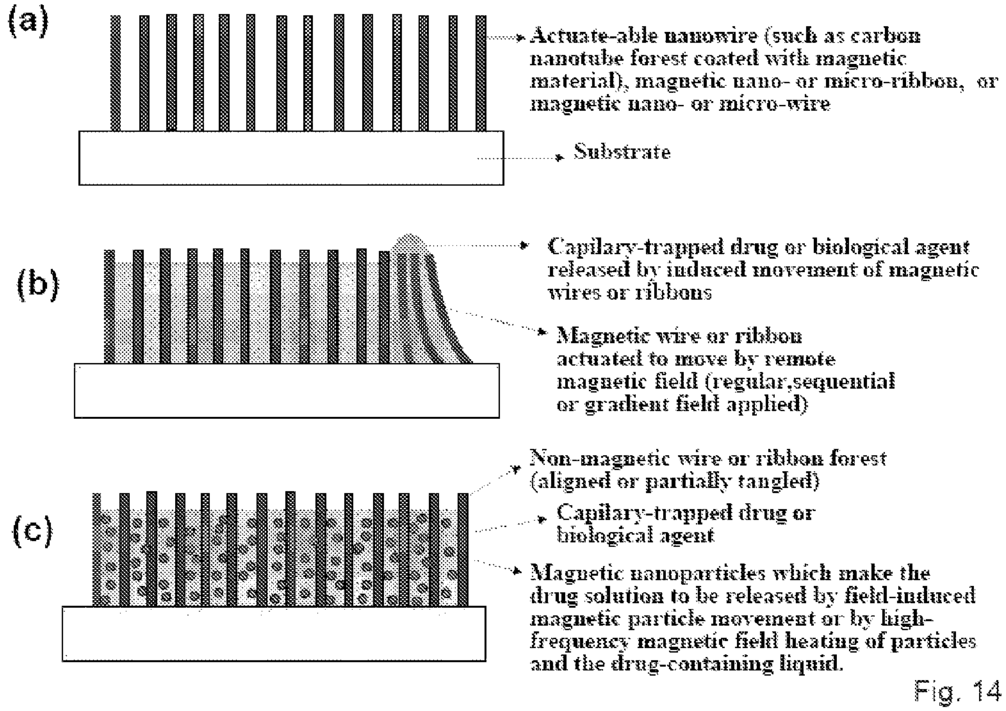
FIG. 14 schematically illustrates an exemplary drug delivery system with nanowire, micro-wire or micro-ribbon array that holds a drug or biological agent and releases it by remotely activated magnetic field.

FIG. 14 schematically illustrates an exemplary drug delivery system with nanowire, microwire or micro-ribbon array that holds a drug or biological agent and releases it by remotely activated magnetic field. The forest can exhibit either vertically aligned structure or somewhat tangled, non-vertical-aligned structure. Two different types of drug release actuation are described, i.e., by the movement of magnetic wires or ribbons themselves (FIGS. 14(*a*) and (*b*)), or by the movement of magnetic nanoparticles placed within the drug-containing liquid stored in the wire or ribbon forest (FIG. 14(*c*)). The drugs or biological agents to be stored and released such as pharmaceutical therapeutic drugs (such as antibiotics, chemotherapy medicine, anti-stenosis drug, insulin), and biologically active agents (such as DNAs, genes, proteins, hormones, collagens and other growth factors) are inserted into the forest of nanowire, microwire or micro-ribbon arrays by various techniques including soaking, supercritical $CO_2$ processing, vacuum suction, pressure injection, boiling water processing, etc.

In FIG. 14(*a*), a forest of magnetically actuate-able nanowire (such as carbon nanotube forest coated with magnetic material), magnetic nanowire, magnetic micro-wire, or magnetic micro-ribbon is prepared on a biocompatible substrate. The drug or biological agent is capillary-trapped in the forest of the in-vivo drug storage device of the type illustrated in FIG. 14, which is released by magnetically induced movement of magnetic wires or ribbons when they are actuated to move by remotely applied magnetic field of regular, sequential or gradient in nature.

The material for the magnetic nanowires, micro-wires or micro-ribbons has to ferromagnetic such that a sufficiently strong response to applied magnetic field is exhibited to squeeze out the stored, drug or biological agent in the forest structure, as illustrated in FIG. 14(*b*). Exemplary ferromagnetic materials include Ni—Fe permalloys, Fe-base, Ni-base, or Co-base soft magnetic amorphous alloys (e.g., Metglas type materials). They should also be biocompatible or coated with biocompatible material such as Ti, Au, Pd, Pt, stainless steel or bio-inert polymers. The desired diameter or thickness of the nanowires, micro-wires or micro-ribbons is in the range of about 0.005-250 micrometers, or in another aspect, 0.01-50 micrometers. An exemplary gap between adjacent wires or ribbons is in the range of about 0.01-50 micrometers.

In FIG. 14(*c*), the nanowires, microwires or micro-ribbons that form the drug-containing forest are non-magnetic. Carbon nanotubes or other metallic or polymer nanowires, microwires or micro-ribbons can be utilized as the forest material. In order to induce the magnetic field induced drug release, magnetic nanoparticles such as $Fe_3O_4$ nanoparticles are added to the drug solution. An application of high frequency ac magnetic field (e.g., in the range 10 KHz-10 MHz, or in another aspect, near 100 KHz) make the magnetic nanoparticles and the drug-containing liquid nearby to get preferentially heated so that a diffusion based drug release is accelerated.

Figure 15:
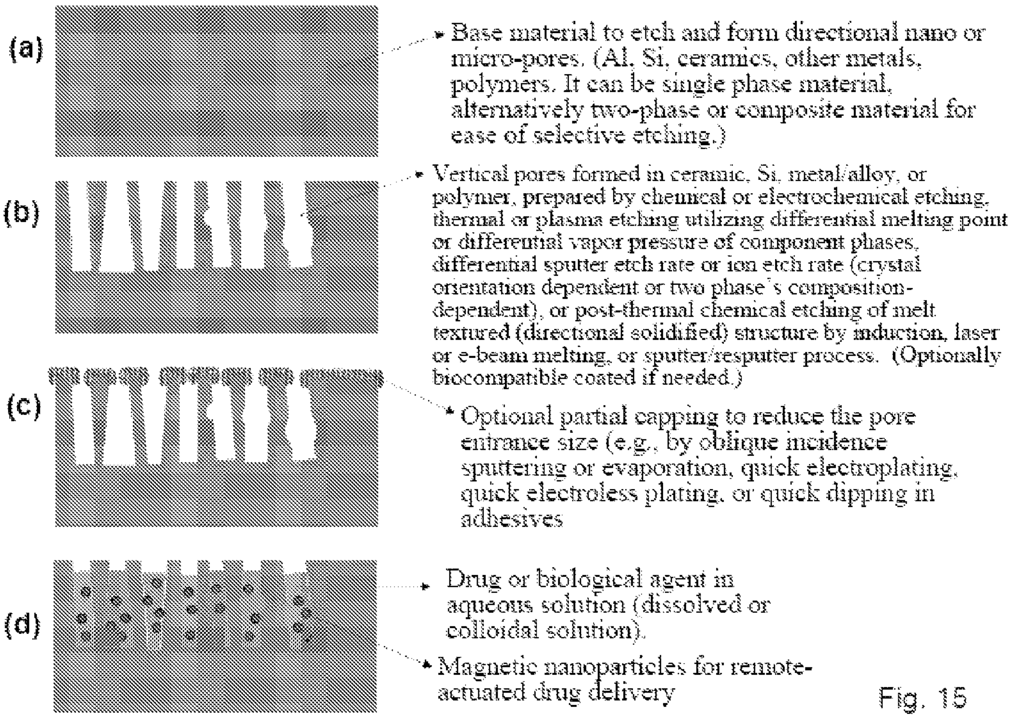
FIG. 15 illustrates an exemplary magnetic remote controllable drug delivery system based on directionally formed porous material filled with magnetic nanoparticles.

Yet another embodiment configuration of drug release device using magnetic remote control is illustrated in FIG. 15. This approach is based on the formation of directionally etched porous material which is then filled a liquid containing drug or biological agent, together with magnetic nanoparticles. The directional pores do not have to be precisely vertical from the drug release point of view. They can be tilted or irregular shaped. As long as the pores are generally aligned and continuously open to the bottom of the pore, they will serve the purpose. The process of fabricating such a drug delivery system is illustrated by FIG. 15(*a*)-(*d*).

First, a suitable base material that can be directionally etched is selected as illustrated in FIG. 15(*a*). Example base materials to etch and form directional nano or micro-pores include Al, Si, ceramics, various metals including Ti or Ti-base alloys (e.g., Ti—Al—V alloys), other refractory metals (e.g., Zr, Hf, Ta, W and their alloys), or stainless steels, metal-ceramic composites, or polymers. It can be a single phase material. Alternatively, two-phase or composite materials with vertically textured, two-phase alloys or ceramic, or diblock copolymers can advantageously be utilized for ease of selective and directional etching for vertically aligned pore formation.

In FIG. 15(*b*), desirably directionally porous structure is formed by various types of chemical, physical or thermal etching. Vertically porous ceramic (e.g., anodized aluminum oxide or Ti oxide), porous Si, porous metal/alloy, porous polymer, prepared by chemical or electrochemical etching, thermal or plasma etching utilizing differential melting point or differential vapor pressure (evaporation rate) of component metallic phases, differential sputter etch rate or ion etch rate (crystal orientation dependent or two phase's composition-dependent), or post-thermal-process chemical etching such as on melt textured (directional solidified) structure by induction, laser or e-beam melting, or sputter/resputter process.

In one aspect, the surface of these pores needs to be biocompatible for an in vivo drug delivery system. If the base material itself is not biocompatible, they can be coated with a layer of biocompatible material such as Ti, Au, Pd, Pt, stainless steel or bio-inert polymers bicoated if needed.

FIG. 15(*c*) illustrates one aspect of the invention where an optional partial capping that reduces the pore entrance size. Such a partial capping helps to prevent the escaping of magnetic particles to retain the remote control capability, and also to minimize any side effect on release of loose magnetic particles in the in-vivo system. In one aspect, the partial capping of drug-releasing pores can be accomplished by oblique incidence sputtering or evaporation, quick electroplating, quick electroless plating, or quick dipping in adhesives.

In FIG. 15(*d*) illustrates one aspect of the invention where various drugs or biological agents are be stored and released, e.g., in one aspect pharmaceutical therapeutic drugs (such as antibiotics, chemotherapy medicine, anti-stenosis drug, insulin) and/or biologically active agents (such as DNAs, genes, proteins, hormones, collagens and other growth factors) are inserted into the micropore or nanopore reservoirs into the FIG. 15(*b*) or FIG. 15(*c*) type structures together with magnetic nanoparticles. The drugs or biological agents can be dissolved in liquid or contained as a colloidal suspension mixture. Various techniques including soaking in drug-containing liquid, supercritical $CO_2$ processing, vacuum suction, pressure injection, boiling water processing, etc. can be utilized for the insertion.

In one aspect, the drug delivery system of the type described in FIG. 15(*c*) or FIG. 15(*d*) is then in-vivo implanted, and remote magnetic field actuated for on-command release of drugs or biologically active agents by magnetic field on/off operation or quantitative dose control using selected magnetic field intensity/frequency/repetition/duration.

Figure 16:
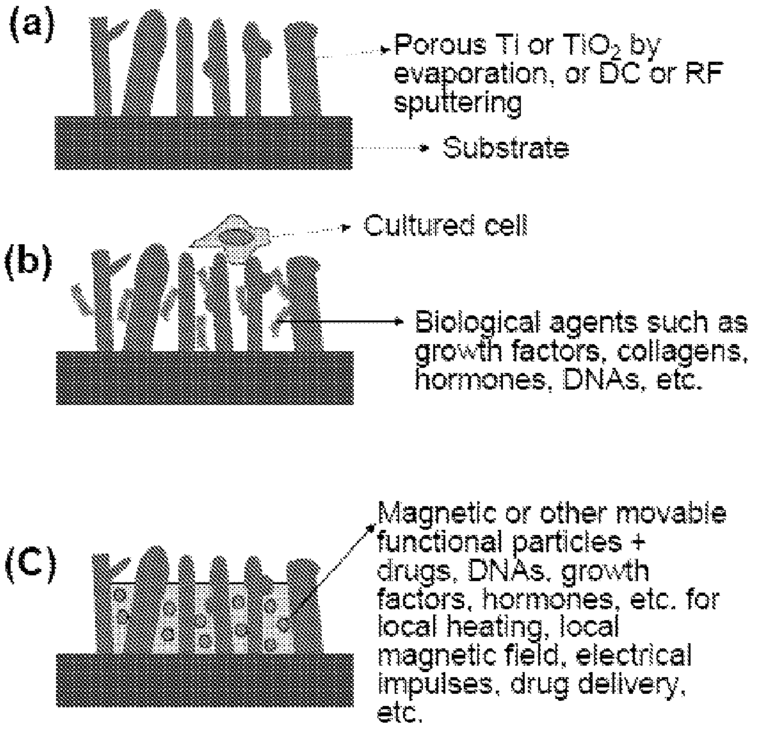
FIG. 16 schematically illustrates an exemplary magnetic remote controllable drug delivery system based on porous structures made by evaporated or sputtered thin or thick films, either as made or post-deposition-etched for removal of one of the phases.

FIG. 16 schematically illustrates an exemplary magnetic remote controllable drug delivery system based on porous structures made by evaporated or sputtered thin or thick films. In one aspect, both the film and the substrate has to be biocompatible for in-vivo drug delivery use. Ti or $TiO_2$ based thin films (or other refractory metal/alloys and their oxides, noble metals/alloys, stainless steels) can be used as the thin film or substrate material. The porous films in FIG. 16(*a*) can be fabricated either as an as-deposited film or as a post-deposition-etched film with one of the phases in a multi-phase microstructure etched away.

In one aspect, a proper selection of sputtering pressure and temperature can introduce porous or rough microstructure in deposited thin films. The self shadowing effect of the obliquely deposited thin film material, e.g., by evaporation can be used to form highly porous or rough films. The sputtering deposition can be carried out by DC, pulse DC, RF sputtering, or ion beam deposition methods. The evaporation can be done by thermal or electron beam evaporation process. Depending on the deposition conditions, a smooth continuous film, rough topology film, or highly porous structure can be obtained. See e.g., J. A. Thornton, *J. Vac. Sci. Technol.* (1986) A4(6):3059, L. J. Meng et al., "Investigations of titanium oxide films deposited by dc active magnetron sputtering in different sputtering pressures," *Thin Solid Films* (1993) 226:22, by K. Robbie et al., "Fabrication of thin films with highly porous microstructure," *J. Vacuum Science & Technology* (1995) 13(3):1032, and J. Rodriguez et al., "Reactively sputter deposited titanium oxide coatings with parallel Penniform microstructure," *Adv. Mater.* (2000) 12(5):341.

In one aspect, once such a porous film structure of formed, as illustrated in FIG. 16(*a*), biological agents such as growth factors, collagens, hormones, DNAs, etc. can be inserted into the porous film structure as illustrated in FIG. 16(*b*) for enhanced in-vivo or in-vitro bio activities such as accelerated cell growth, enhanced hormone or albumin secretion, increased protein synthesis from the cells involved, etc.

Figure 17:
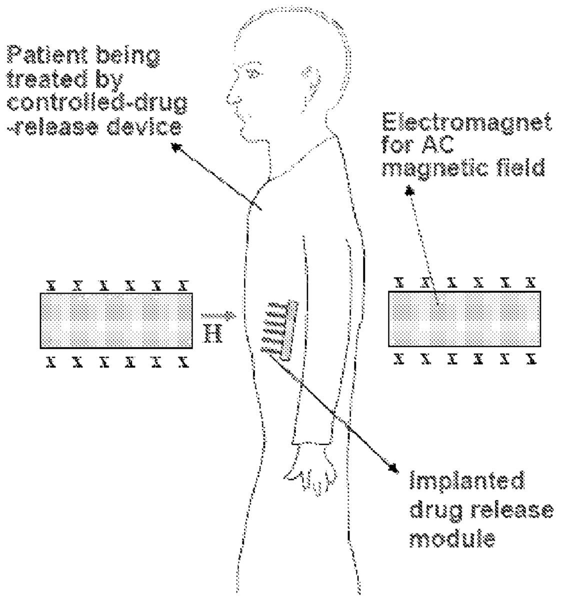
FIG. 17 schematically illustrates an exemplary, remote magnetically actuated, on-off controllable or programmable drug release device using operational methods of moving or high-frequency heating of magnetic particles trapped in nanopores or micropores in the drug delivery system implants.

FIG. 16(*c*) illustrates one embodiment where a drug in liquid (either dissolved or as a colloidal mixture with the carrying liquid such as water or body fluid), together with magnetic nanoparticles, is inserted into the nano or micro pores in the thin film. Various techniques including soaking in drug-containing liquid, supercritical $CO_2$ processing, vacuum suction, pressure injection, boiling water processing, etc. can be utilized for the insertion. The drug delivery system of the type described in FIG. 16(*c*) is then in-vivo implanted as illustrated in FIG. 17, and remote magnetic field actuated for on-command release of drugs or biologically active agents by magnetic field on/off operation or quantitative dose control using selected magnetic field intensity, frequency, repetition cycles, and duration of the magnetic field.

3. Elastically Compliant Implant Material for Bone Growth

Alternative embodiments of the invention comprise a unique configuration of elastically compliant implant material for, e.g., bone growth, which provides subdivided, more reliable, and stress-accommodating implant fibers more or less vertically arranged in a spring configuration, and which also provides a strong mechanical reinforcement of the grown bone via bone-metal wire composite formation. In one aspect, Ti based metal or alloy or any biocompatible alloy such as stainless steel can be utilized, e.g., minimal separation failures at the implant-hard tissue interface, which also provides strength and toughness reinforcement of the grown bone via bone-metal wire composite formation.

Figure 18:
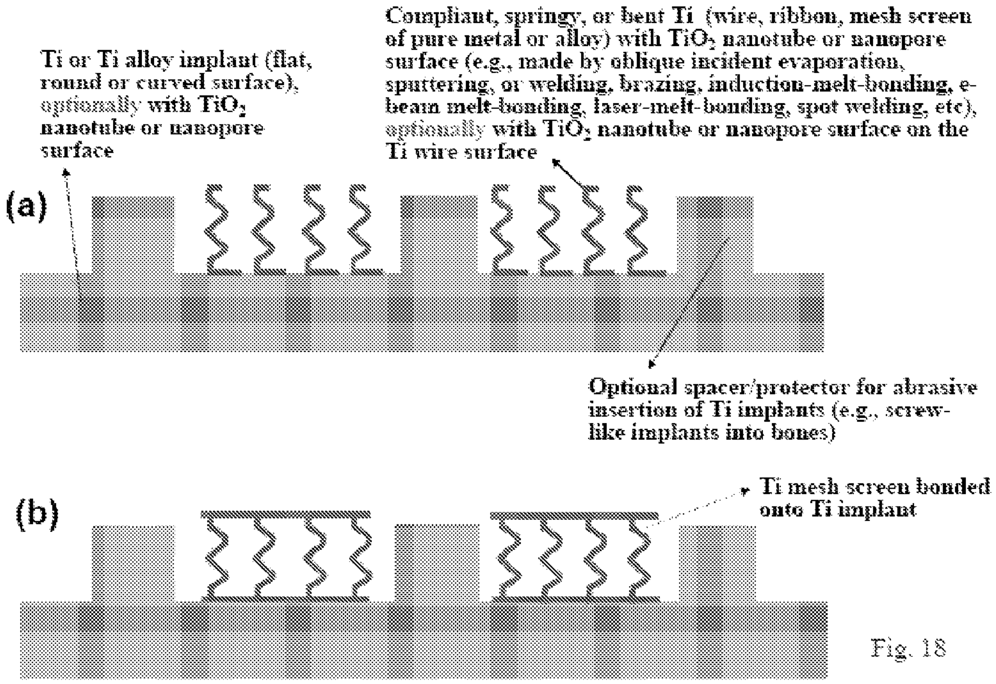
FIG. 18 depicts exemplary structures of elastically compliant implant material for bone growth using Ti based metal or alloy or any biocompatible alloy such as stainless steel.
Figure 18:
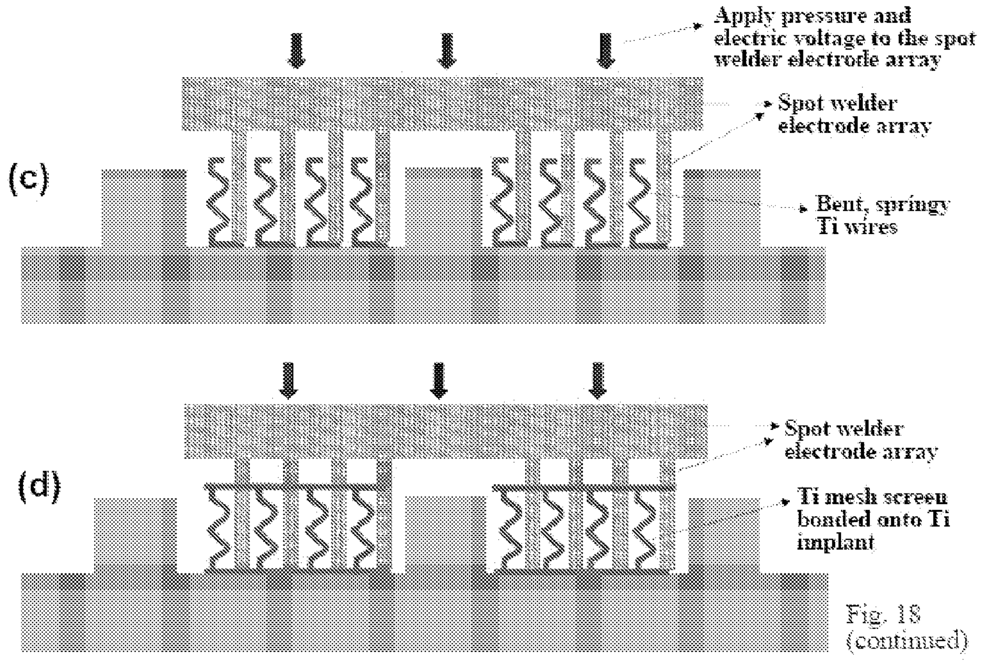

Exemplary structures of such elastically compliant implant material for bone growth is illustrated in FIG. 18. On the surface of Ti or Ti alloy implant (flat, round or curved surface), an array of vertically spring-configured Ti wires (FIG. 18(*a*)) or spring-configured Ti mesh screens (FIG. 18(*b*)) or any other spring-like structure of Ti wires or ribbons are bonded, for example, by using spot welding procedure as illustrated in FIG. 18(*c*) and FIG. 18(*d*). Optional spacer/protector may also be added onto the surface of the Ti implant base in order to protect the Ti spring members during abrasive insertion of Ti implants (e.g., screw-like implants into bones or teeth).

Compliant, springy, or bent Ti (wire, ribbon, mesh screen of pure metal or alloy) in macroscale (e.g., the diameter/thickness of the wire/ribbon is more than ~1-10 micrometers) can be made by employing pre-multiple-bent Ti wires or ribbons cut to desired length. In the case of micro or nanowires of Ti, these can be made by oblique incident evaporation or sputtering. These spring-configured Ti springs in wire or mesh-screen form can be attached onto the Ti implant surface by diffusion bonding, brazing, induction-melt-bonding, e-beam melt-bonding, laser-melt-bonding, spot welding, etc.

The surface of the Ti wires or ribbons as well as the surface of the Ti implant base can be optionally anodized to form cell- or bone-growth accelerating $TiO_2$ nanotubes or nanopores, as made by using the anodization process described earlier.

Instead of using Ti based metals or alloys (e.g., Ti—Al—V alloys), or any biocompatible alloy selected from refractory metals (e.g., Zr, Hf, Ta, W and their alloys), or stainless steels can be employed as the spring material or the implant base material. If the spring material selected is not biocompatible, its surface can be coated with a biocompatible or noble metal, alloy or polymer.

Figure 19:
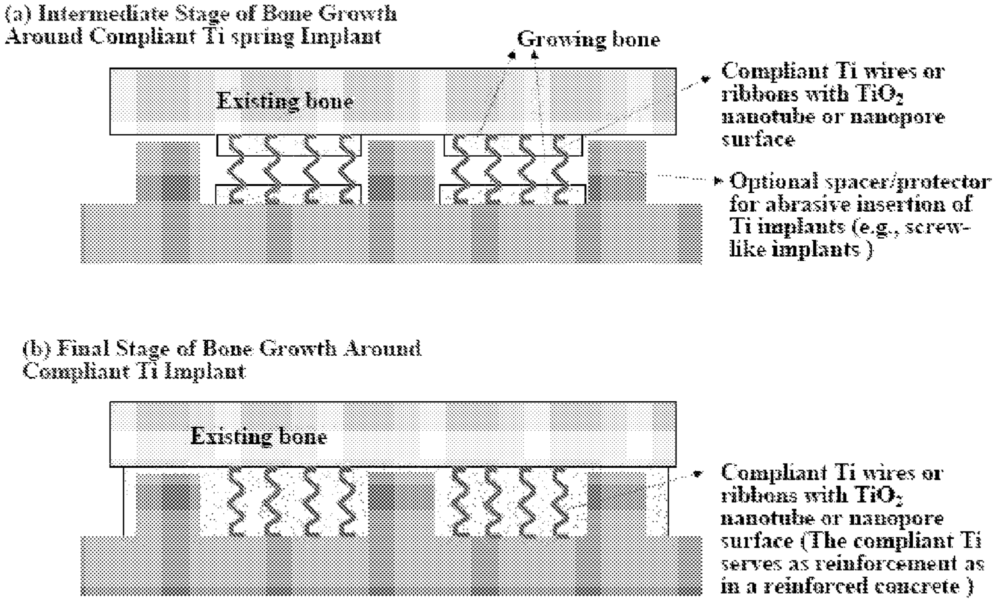
FIG. 19 schematically illustrates exemplary bone growth steps around compliant implant material using Ti based metal or alloy or any biocompatible alloy such as stainless steel.

FIGS. 19(*a*) and (*b*) describe the alternative embodiments comprising bone growth steps around compliant Ti spring material, the spring nature of the wires or ribbons accommodate any stress applied (shear, tensile or compressive stresses) during the bone growth, thus preventing the fracture or delamination of the newly growing bone. In one aspect, once the bone growth is completed filling the gap between the implant and existing bone, the presence of Ti wires, ribbons, mesh-screens within the grown bone serves as reinforcement as in a reinforced concrete, thus minimizing failures of the attached bone.

Figure 20:
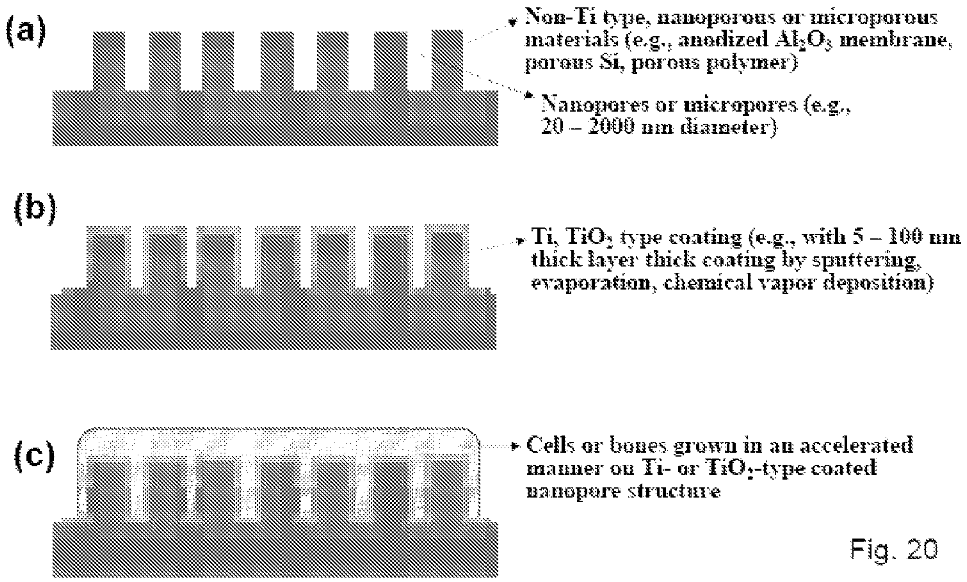
FIG. 20 illustrates an exemplary fabrication method for converting the surface of a non-Ti type nanoporous or microporous materials to cell- or bone-growth-accelerating structure by thin biocompatible surface coating of Ti, $TiO_2$ or other related biocompatible metals and alloys.

4. Non-Metallic or Non-Ti Based Substrates with their Surfaces Converted to $TiO_2$-Type Nanotubes or Nanopores Additional exemplary embodiments comprise utilizing non-metallic or non-Ti based substrates and converting their surfaces into $TiO_2$ type nanotubes or nanopore so as to exhibit desirable cell or bone growth accelerating characteristics. Examples of non-Ti type, nanoporous or microporous materials include anodized $Al_2O_3$ membrane, porous Si, porous polymer, and porous metals and alloys in general, as illustrated in FIG. 20(*a*).

In one aspect, two methods of accomplishing such a biocompatible modified structure are disclosed. One method is to coat the surface of the materials (which in one embodiment have been processed to have nanopores before the coating) (in alternative aspects the materials can comprise anodized alumina, porous silicon, diblock-copolymer-based porous polymer, or any combination thereof) with a thin and biocompatible Ti or $TiO_2$ type layer, which in alternative embodiments can be between about 1 to 50 nm thick layer, by sputtering, evaporation, chemical vapor deposition, plasma spray, thermal spray, etc. An exemplary process is illustrated in FIG. 20. A thin biocompatible surface coating of Ti, $TiO_2$ or other related biocompatible metals and alloys are deposited by physical vapor deposition (such as sputtering or evaporation) or chemical vapor deposition, as illustrated in FIG. 20(*b*). The accelerated cell growth on such a nanostructure with biocompatible coating is shown in FIG. 20(*c*).

Another exemplary method of the invention is to apply a thick layer coating of Ti or related metals, including a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic, or any combination thereof; which in alternative embodiments are applied at 100-2000 nm thicknesses; and in alternative aspects are applied on a generally smooth, but not nanoporous and at most macro-porous, Si, Si oxide, carbon, diamond, noble metals (such as Au, Ag, Pt and their alloys), polymer or plastic materials, or composite metals, ceramics or polymers, and then anodizing the thick Ti or related metals and converting at least a portion of the Ti or related metal surface into $TiO_2$ type nanotubes or $TiO_2$-surfaced nanopores.

The products of manufacture of the invention can have either the thin or thick layer coating, or combination thereof, and can be used for any variety of applications as described herein, including for in vitro testing of drugs, chemicals or toxins, or as in vivo implants, use in making and using artificial tissues and organs—which includes cell, bone and tooth growth, and as drug delivery devices.

Figure 21:
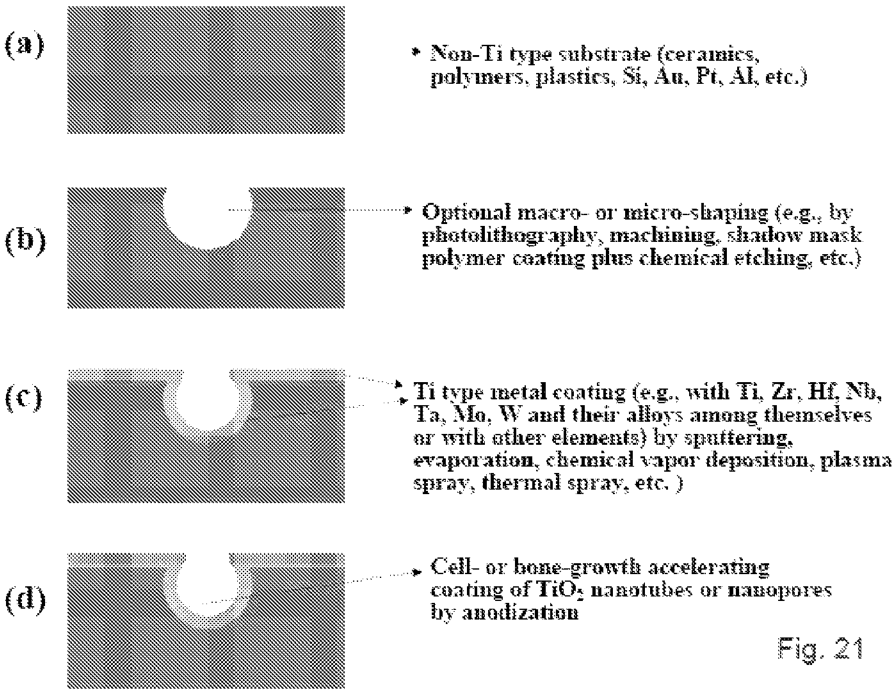
FIG. 21 schematically illustrates an exemplary process of creating a $TiO_2$ nanotube or nanopore surface structure on non-Ti type surfaces by thick Ti film deposition followed by anodization, including formation of $TiO_2$ nanotubes or nanopores by anodization of thick, deposited Ti on a non-Ti type substrate comprising ceramics, polymers, plastics, Si, Au, Pt and/or Al, etc.

The drawings in FIG. 21 schematically illustrate this exemplary process of creating a $TiO_2$ nanotube or nanopore surface structure on non-Ti type surfaces by thick Ti film deposition followed by anodization. The exemplary process used in FIG. 21 also can comprise a formation of re-entrant loop shape cavity, which might be useful to, e.g., further lock-in growing bones, teeth or other tissues.

Figure 22:
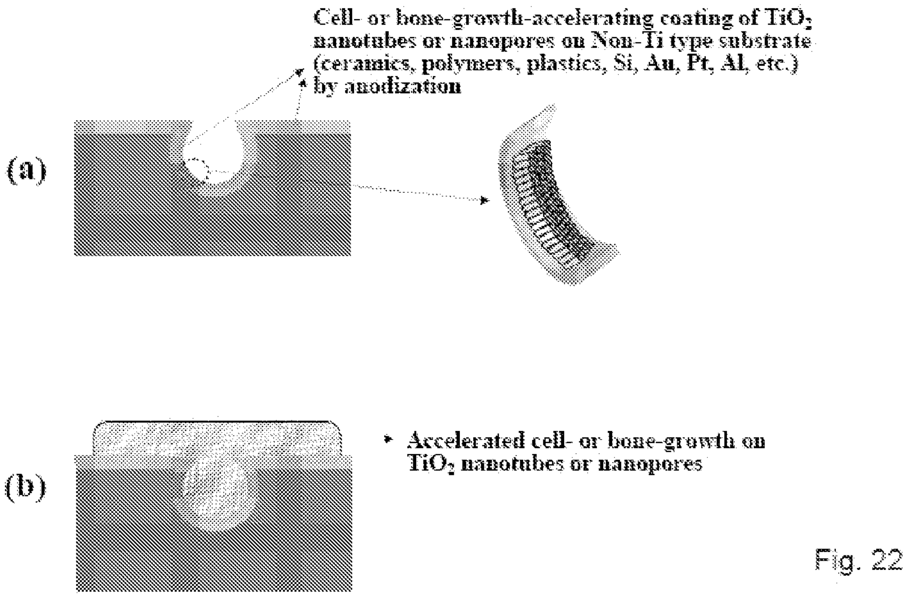
FIG. 22*a* describes the nature of cell- or bone-growth-accelerating coating of $TiO_2$ nanotubes or nanopores by anodization of thick-film Ti coating on an exemplary pre-patterned, non-Ti type substrate (ceramics, polymers, plastics, Si, Au, Pt, Al, etc.), and resultant cell or bone growth with a mechanically more reliable lock-in structure.
FIG. 22*b* shows how accelerated cell- or bone-growth is achieved on $TiO_2$ nanotubes or nanopores of the invention.

Shown in FIG. 22 is the nature of cell- or bone-growth-accelerating coating of $TiO_2$ nanotubes or nanopores by anodization of thick-film Ti coating on an exemplary pre-patterned, non-Ti type substrate (ceramics, polymers, plastics, Si, Au, Pt, Al, etc.), and resultant cell or bone growth with a mechanically more reliable lock-in structure.

Figure 23:
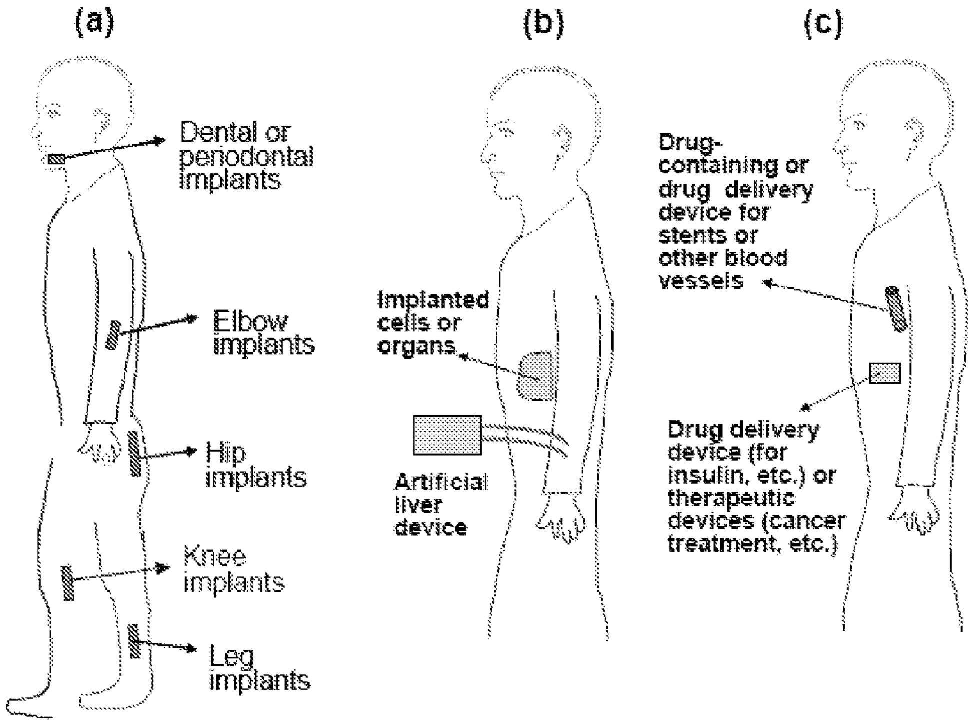
FIG. 23 illustrates exemplary bio implants for in vivo growth of bones, teeth, cells, organs, ex vivo functional bio devices such as artificial liver devices, orthopedic/dental implants, as well as drug delivery devices and therapeutic devices based on biocompatible implants.

FIG. 23 schematically illustrates various potential in vivo or ex-vivo bio implant applications of the inventive, biomaterials capable of accelerated cell/bone/teeth growth, strongly locked-in bone or cell growth, or functional drug delivery and therapeutics. Various inventive nanopore or nanotube structures described in relation to FIGS. 1-22 can be utilized for these biomedical device applications. Examples shown include orthopedic and dental implants, cell or organ implants, drug delivery devices such as controlled release of insulin by magnetic actuation, artificial liver devices, drug-protected stents (e.g., to prevent/minimize restenosis) or other tubules inserted into blood vessels and in various other body parts, and therapeutic devices such as magnetic field induced local heating for cancer treatment. Cell growth inhibiting drugs can also be inserted in the inventive nanopores or nanotubes of other implants (e.g., drug delivery modules) to prevent/minimize scar tissue formation.

Figure 24:
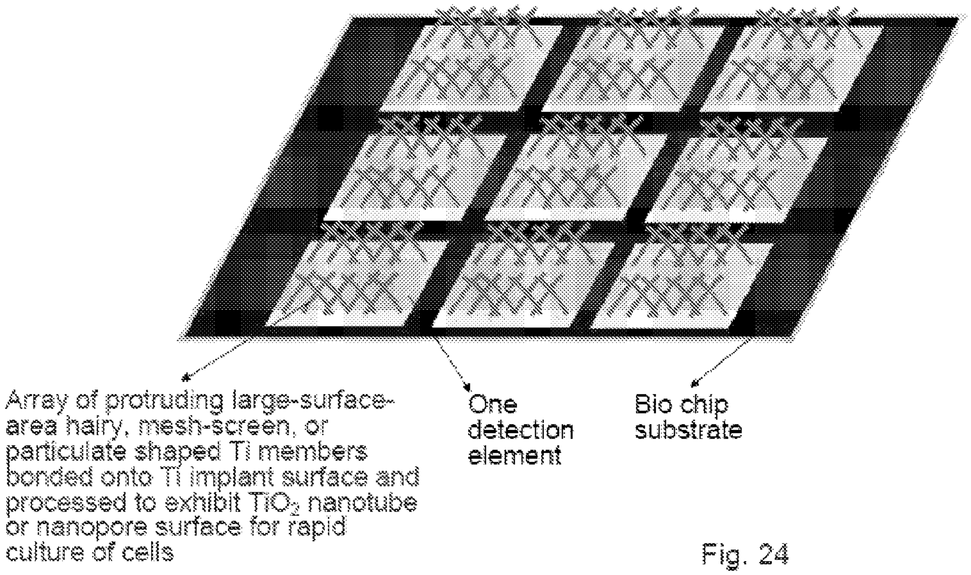
FIG. 24 illustrates an exemplary accelerated cell growth device comprising an array of protruding, large-surface-area, hairy, mesh-screen or particulate shaped Ti members bonded onto Ti substrate and processed to have $TiO_2$ nanotube or nanopore surface, for applications such as cell supply, rapid cell identification, harvesting of cell components, secreted proteins, albumin and other bio components generated by cultured cells; including illustrating exemplary arrays of the invention comprising protruding large-surface-area hairy, mesh-screen, or particulate shaped Ti members bonded onto Ti implant surface and processed to exhibit $TiO_2$ nanotube or nanopore surface for rapid culture of cells, with at least one detection element, and with a biochip substrate.

The various large-surface-area biomaterials described in relation to FIGS. 1-22 can be useful for ex-vivo accelerated cell growth devices. Rapid production of healthy cells including liver cells, bone cells, kidney cells, blood vessel cells, skin cells, periodontal cells, and stem cells can be realized. A device application of such an ex-vivo accelerated cell growth is shown in FIG. 24, which uses an example of an array of protruding, large-surface-area, hairy, mesh-screen or particulate shaped Ti members bonded onto Ti substrate and processed to have $TiO_2$ nanotube or nanopore surface, for applications such as cell supply, rapid cell identification, harvesting of cell components, secreted proteins, albumin and other bio components generated by cultured cells. Other types of large-surface-area biomaterials such as illustrated in FIGS. 10-22 can also be utilized for such rapid cell growth.

Figure 25:
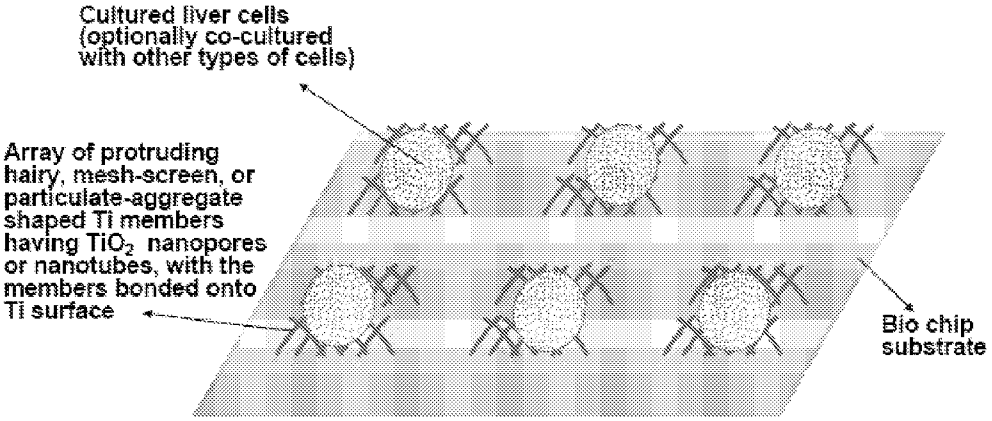
FIG. 25 schematically illustrates an exemplary accelerated liver cell growth device comprising an array of protruding, large-surface-area, hairy, mesh-screen or particulate shaped Ti members bonded onto Ti implant surface and processed to exhibit $TiO_2$ nanotube or nanopore surface, for culturing a cell, e.g., a liver cell, optionally also comprising other cell types, for applications such as rapid toxicity testing of drugs or chemicals, on a biochip substrate.

FIG. 25 schematically illustrates an exemplary accelerated liver cell growth device comprising an array of protruding, large-surface-area, hairy, mesh-screen, particulate, or particulate-aggregate shaped Ti members bonded onto Ti implant surface and processed (e.g., by anodization) to exhibit $TiO_2$ nanotube or nanopore surface, for applications such as rapid toxicity testing of drugs or chemicals. Many new types of therapeutic or analytical drugs are explored and developed every year by pharmaceutical companies and other biotech R&D institutes. If a drug is toxic to human or animal body under in vivo situation, the liver is one of the first organs to sense it and try to isolate the toxic materials. A bio-chip containing an array of healthy, three-dimensionally cultured liver cells, e.g., 10×10, 100×100 or 1000×1000 sensing elements can thus allow simultaneous evaluation of many drugs for much accelerated screening and development of biologically acceptable drugs. Likewise, many chemicals, polymers, injection fluids, and composites that may be useful for in vivo applications can be rapidly tested for toxicity using the inventive device of FIG. 25. The accelerated, healthy liver cell growth made possible with various large-surface-area biomaterials described in relation to FIGS. 1-22 can also be utilized as the basis of artificial liver devices for patients waiting for transplant or as a temporary aid to liver function after transplant. Other functional organs applications such as artificial kidney can also be considered.

Figure 26:
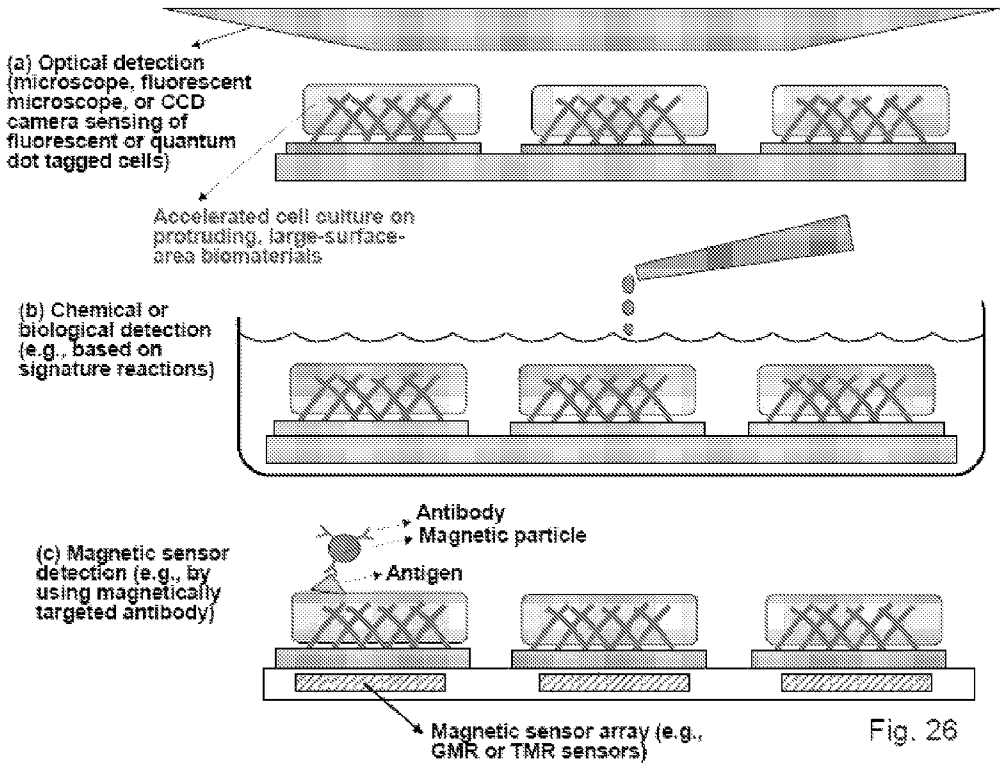
FIG. 26 schematically illustrates exemplary embodiments of the inventive bio-chip test apparatus useful for drug toxicity, chemical toxicity, or cell identification testing, with the apparatus comprising an array of the inventive, protruding, large-surface-area biomaterials, with the analytes detected by FIG. 26(*a*) optical means, including use of any device for optical detection, e.g., using a microscope, fluorescent microscope, or CCD camera sensing of fluorescent or quantum dot tagged cells, and illustrating the accelerated cell culture on these exemplary protruding, large-surface-area biomaterials.

FIG. 26 schematically illustrates exemplary embodiments of the inventive bio-chip test apparatus useful for drug toxicity, chemical toxicity, or cell identification testing, with the apparatus comprising an array of the inventive, protruding, large-surface-area biomaterials or nanoporous, microporous materials, with the analytes detected by (a) optical means (such as microscopy using visible, infrared or UV light), laser, (b) chemical or biological analysis (such as using assays for chemical or biological reactions in combination with various analytical tools), or (c) magnetic sensor technique (such as magnetoresistance probes based on GMR sensors, TMR sensors or SQUID magnetometers) which measure the change in the position or binding of magnetic nanoparticles via the change in the magnitude of detected magnetism.

5. Biocompatible Materials Configured in Loose Particles, Loose Short-Fibers, or Loose Flakes The invention also provides biocompatible materials configured in loose particles, loose short-fibers, or loose flakes, with each of these particles or short fibers having their surfaces covered with cell- or bone-growth-accelerating nanotube or nanopore array structure. These loose powder configurations allow convenient in-vivo or in-vitro implementations of, e.g., a paste type or bone cement type applications. Because of the presence of the very-large-surface-area, biocompatible, cell-activity-accelerating structure such as titanium oxide nanotubes or nanopores on the surface of such particles, short fibers, or flakes, significantly accelerated and viable cell growth and bone growth occurs. In one aspect, the compositions of the invention (e.g., products of manufacture, such as arrays, drug delivery devices) comprise structures as described, e.g., in PCT/US2006/016471, filed on Apr. 28, 2006, Jin et al.; Oh et al., "Growth of Nano-scale Hydroxyapatite Using Chemically Treated Titanium Oxide Nanotubes", *Biomaterials* (2005) 26:4938-4943; "Significantly Accelerated Osteoblast Cell Growth on Aligned $TiO_2$ Nanotubes," *J. Biomedical Materials Research* (2006) 78A: 97-103

One embodiment comprises a loose particle, short-fiber or flake shaped biomaterial configuration that allows pharmaceutical drugs, growth factors and other biological agents to be added and stored within the nanotubes or nanopores for multifunctional advantages, and in alternative aspects allows slow, diffusional, time-dependent release for even further accelerated growth of healthy cells.

One embodiment comprises an optically transparent or translucent cell-culturing substrate with nano imprint patterned nanostructure. These devices of the invention provide the optical transparency needed by a cell culture substrate, and this embodiment allows a microscopic examination of the cell behavior using inverted microscope with transmitted light illumination. In one aspect, a surface of such a nanostructure is coated with an optically transparent or translucent, very thin film of, in alternative embodiments: Ti or Ti-base alloys (e.g., Ti—Al—V alloys), other refractory metals (e.g., Zr, Nb, Hf, Ta, W and their alloys), or $TiO_2$, $Nb_2O_5$, $ZrO_2$, $HfO_2$, $Ta_2O_5$, $W_2O_3$ or mixed alloy oxide. In one aspect, the desired thickness of such Ti or $TiO_2$ related coating is about 1 to 50 nm, or about 1 to 20 nm, or in alternative embodiments: at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 or more nm.

One embodiment comprises an elastically compliant nanostructure substrate coated with Ti, $TiO_2$ or related metal and metal oxide films, including a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic. These devices of the invention help ameliorate the stress or strain that the growing/propagating cells experience, and thus have a positive effect on the cell growth behavior. By providing elastically soft substrate which is made even more flexible by virtue of added surface nanostructure, a further enhanced cell growth is obtained using these exemplary devices of the invention.

In one embodiment, drugs or biological agents are stored inside the loose or fixed structures on the surfaces of devices of this invention, and/or in the pores of $TiO_2$ type nanotubes, nanowires and/or nanopores on the surface of the particles, short fibers, or flakes. In one embodiment, the slowly released compounds include pharmaceutical therapeutic drugs (such as antibiotics, chemotherapy medicine, anti-stenosis drug, insulin), and/or biologically active agents (such as DNAs, genes, proteins, hormones, collagens and other growth factors such as BMP (bone morphological protein)). The drugs or biological agents can be dissolved in liquid or contained as a colloidal suspension mixture. Various techniques including soaking in drug-containing liquid, supercritical $CO_2$ processing, vacuum suction, pressure injection, boiling water processing, etc. can be utilized for the insertion.

Another embodiment comprises use of magnetic nanoparticles inserted into the nanopore reservoirs together with drugs or biological agents so that a remote, magnetic-field-controlled, on-demand delivery of drugs or biological agents can be accomplished with enhanced kinetics of delivery in vivo, based on a mechanism of magnetic particle movement in the drug- or biological-agent-containing liquid when a gradient or orientation-changing magnetic field is applied, or on a mechanism of magnetic hyperthermia type, preferential heating of magnetic nanoparticles when a high frequency ac field actuation, e.g., at 100 KHz, is applied.

One exemplary step to make a cell-growth-accelerating cement comprising Ti is to prepare the Ti particles, short fibers or flakes, with a desired size of average diameter (or thickness in the case of flakes) in the range of approximately 0.2 to 2000 micrometers, or in another aspect, or in the range of about 2 to 500 micrometers. They can be synthesized by using a number of different methods such as; i) atomization, ii) plasma spray, iii) chemical precipitation and decomposition or heating, iv) evaporated or sputtered film deposition and scraping off the substrate or chamber wall where the coating id deposited. These loose particles, loose short-fibers, or loose flakes are then subjected to anodization treatment to convert the surface into $TiO_2$ nanotube, nanowire and/or array structure. An exemplary anodization process is to use 5 wt % HF in water, at an applied voltage of about 20 V, and anodization duration of 1-100 minutes. After the anodization, the loose particles, loose short-fibers, or loose flakes with a $TiO_2$ nanotube, nanowires and/or array surface can optionally be heated to ~300-800° C. for phase changes from amorphous to crystallized phase such as the anatase phase.

Figure 27:
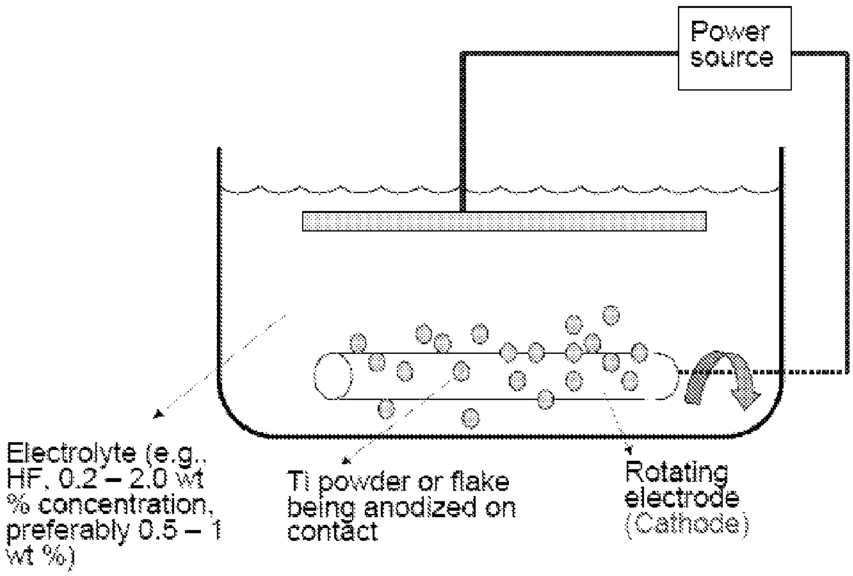
FIG. 27 describes an exemplary method of creating loose, $TiO_2$-nanofiber-coated or $TiO_2$-nanotube-coated Ti powder (using, e.g., spherical, elongated, random or short-wire shape particles) by rotating or moving the electrode (alternatively, the bottom electrode can stay still but the powders are now agitated instead, and made to move around to occasionally touch the electrode); noting optionally: electrolytes at, e.g., HF, 0.2 to 2.0 wt % concentration, or alternatively at 0.5 to 1 wt %), Ti powder or flake being anodized on contact, and a rotating electrode (a cathode).

The drawing of FIG. 27 describes an exemplary method of creating loose, $TiO_2$-nanofiber-coated or $TiO_2$ nanotube-coated Ti powder (spherical, elongated, random or short-wire shape particles) by rotating or moving the electrode (alternatively, the bottom electrode can stay still but the powders are now agitated instead, and made to move around to occasionally touch the electrode). The surface of the Ti particles can be anodized when they are in electrical contact with the rotating electrode. Repeated tumbling of the particles can allow additional surface regions of the Ti particle to be anodized.

Figure 28:
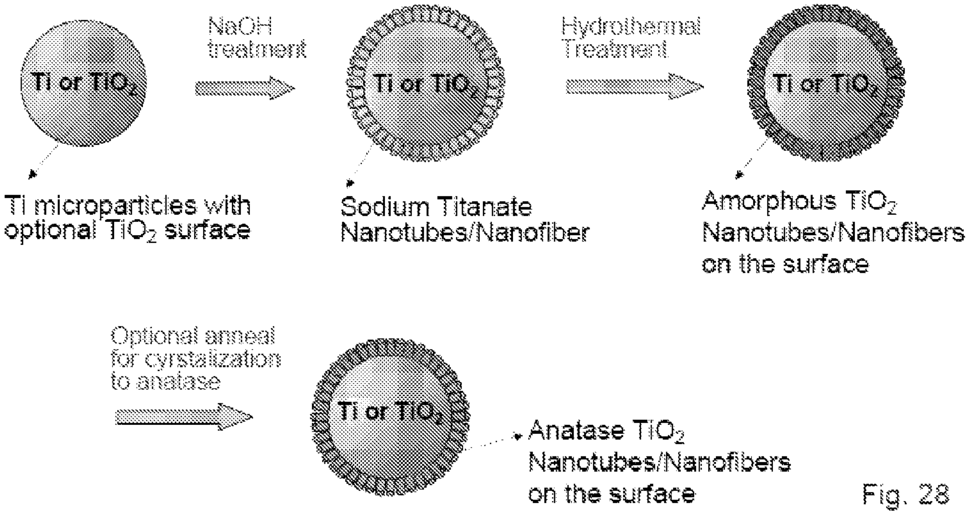
FIG. 28 schematically illustrates an alternative technique of creating $TiO_2$-nanofiber-coated or nanotube-coated Ti powder of micro-sized or macro-sized (e.g., spherical, elongated, random or short-wire shape or flake-shape or needle particles, by NaOH chemical treatment to form sodium titanate intermediate phase nanotubes first on the Ti powder surface, then converting them into $TiO_2$ nanofibers or nanotubes by hydrothermal treatment, followed by optional heat treatment to convert amorphous $TiO_2$ into crystallized $TiO_2$; and the exemplary steps of NaOH treatment (to generate sodium titanate nanotubes/nanofiber), hydrothermal treatment (to generate Amorphous $TiO_2$ nanotubes/nanofibers on the surface), and optional annealing for crystallization to an anatase (Anatase $TiOO_2$ nanotubes/nanofibers on the surface).

FIG. 28 schematically illustrates an alternative technique of creating $TiO_2$ nanotube-coated or $TiO_2$-nanofiber-coated Ti powder of micro-sized or macro-sized (spherical, elongated, random or short-wire shape or flake-shape particles. The starting Ti particles (which may have some native oxidized $TiO_2$ oxide or suboxide surface can be spherical or random in shape, and have desirable, average particle diameter in the range of about 0.2 to 2000 micrometers, or in another aspect, about 2 to 500 micrometers. The Ti powder is first subjected to a NaOH chemical treatment, e.g., by soaking in about 0.01-5 Normal (in one aspect, about 0.5-2 N) NaOH solution, for about 20-120° C./1 sec-1 hr, e.g., for about 5 sec-500 sec, to form a surface intermediate phase of sodium titanate nanotubes or nanofibers. The sodium titanate can be expressed with an exemplary formula of $Na_2Ti_2O_5.H_2O$ type hydroxide or $Na_2Ti_3O_7$, but other variations are also possible.

These sodium titanate nanotubes or nanofibers are then converted into $TiO_2$ nanofibers or nanotubes by hydrothermal treatment, e.g., by heating in boiling water at about 20-120° C. for about 1 sec-1 hr, or about 5 sec-500 sec. The water takes away sodium from the sodium titanate and leaves only titanium oxide material behind.

After the anodization, the loose particles, loose short-fibers, or loose flakes with a $TiO_2$ nanotube or nanofiber array surface can optionally be heated to about 300-800° C. for phase changes from amorphous to crystallized phase such as the anatase phase. The heating rate to the crystallization temperature is important as too fast heating tends to destroy the crystal shape and introduces an undesirable internal stress in the material. A heating rate of slower than 10° C./min, or in another aspect, slower than about 2° C./min is desired.

Figure 29:
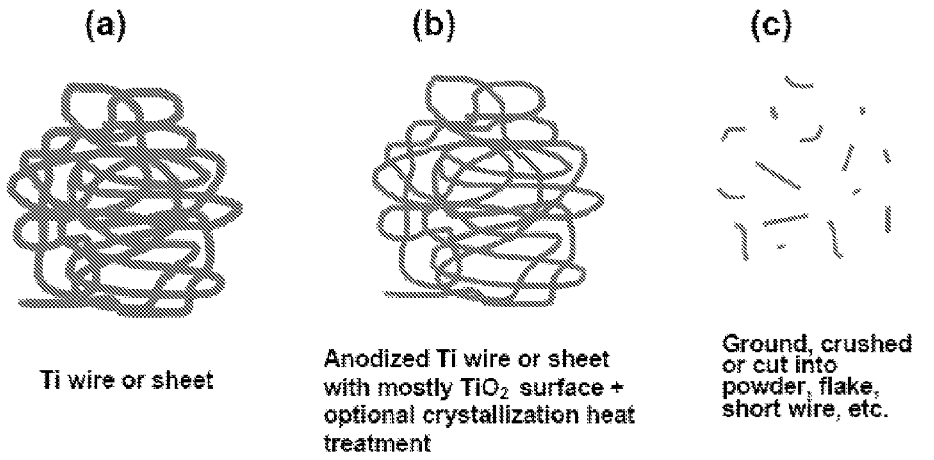
FIG. 29 schematically illustrates an exemplary inventive process of utilizing an extended anodization to create thinner and grindable $TiO_2$ wire or ribbon to produce powder, flake, short fiber, etc., each segment having a cell-growth-accelerating $TiO_2$ nanotube or nanopore surface structure.

An alternative exemplary method of synthesizing the desired $TiO_2$-nanotube-covered loose particles or loose short-fibers, or loose flakes for biocompatible, cell- or bone-growth accelerating cement type applications, is to utilize a novel processing method, e.g., as described in FIG. 29. The drawing schematically illustrates an exemplary process of utilizing an extended anodization to create thinner and grind-able $TiO_2$ wire or ribbon. Thin Ti wires (with a spherical, oval, irregular or random cross-sectional shape) or ribbons, with a diameter or thickness in the range of about 0.2-2000 micrometers, or in another aspect, about 2-500 micrometers, average size, are subjected to an exemplary anodization process, e.g., 5 wt % HF in water, at about 20 V applied voltage for a duration of 1-100 minutes.

The anodization process is a combination of etching away surface material and an addition of oxidized layer on the material surface. A use of extended anodization time creates a sufficient $TiO_2$ penetration into the thickness of the Ti wires or ribbons to make the wires or ribbons less ductile. In order to make a good use of such induced brittleness, a sufficient thickness of the oxide layer relative to the remaining, ductile, metallic core materials is essential. The desired volume of the $TiO_2$ surface layer formed is at least 50% of the overall diameter or thickness of the Ti wire or ribbon, or in another aspect, at least 90%. The predominantly $TiO_2$ wires or ribbons are then subjected to mechanical grinding, pulverization, or ultrasonic sonication in a liquid so as to produce powders, short fibers, or flakes, each segment having a cell-growth-accelerating $TiO_2$ nanotube, nanofiber or nanopore surface structure. The desired diameter of the p powders, short fibers, or flakes can in one aspect be in the range of about 0.1-100 micrometers, and the desired length in the case of fibers or flakes can in one aspect be in the range of about 10-5,000 micrometers.

An optional crystallization heat treatment can be given before or after the grinding operation. The crystallization heat treatment by heating to ~300-800° C. introduces a phase changes from amorphous to crystallized phase such as the anatase phase.

Figure 30:
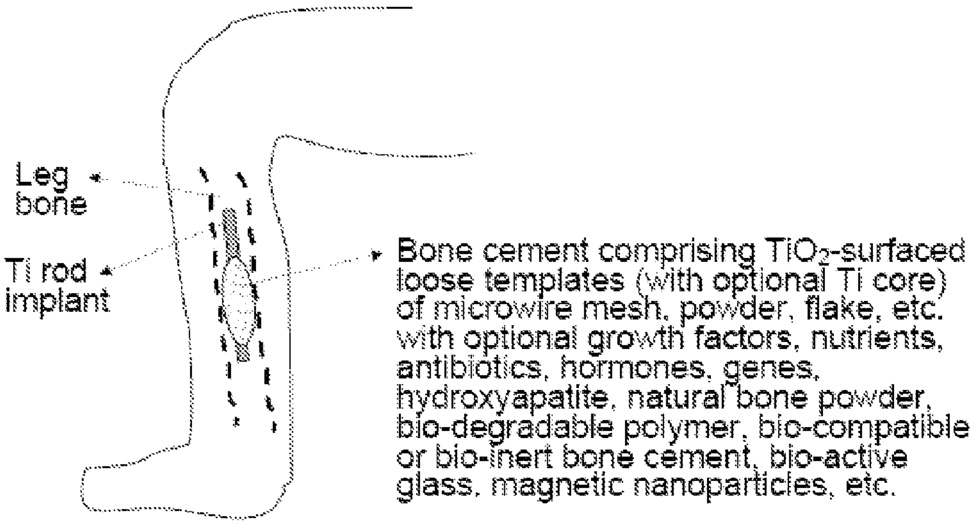
FIG. 30 illustrates an exemplary use of $TiO_2$-nanotube-coated powders or mesh screen of $TiO_2$ (with optional Ti core) to accelerate the bone growth and regenerative-healing process; and use of an exemplary product of this invention comprising bone cement comprising $TiO_2$-surfaced loose templates (with optional Ti core) of microwire mesh, powder, flake, etc. with optional growth factors, nutrients, antibiotics, hormones, genes, hydroxyapatite, natural bone powder, biodegradable polymer, bio-compatible or bio-inert bone cement, bio-active glass, magnetic nanoparticles, etc.

Such $TiO_2$-nanotube-coated loose powders, short fibers, or flakes of Ti can be useful as a component of accelerated-bone-growth cement. As illustrated in FIG. 30, the $TiO_2$-nanotube-coated powders, short fibers, or flakes of Ti, as well as small fragmented pieces of mesh screen of $TiO_2$ (with optional Ti core), can be applied near the in-vivo location where accelerated bone growth is desired. The powders, short fibers, or flakes, or fragmented pieces of mesh screen of $TiO_2$ can also be mixed with bone-growth nutrient, hydroxyapatite, natural bone powder, bio-degradable polymer, bio-compatible or bio-inert bone cement, bio-active glass, or optionally with biological agents of growth factors such as BMP (bone morphogenic protein) or collagen, or other biological agents such as antibiotics, therapeutic drugs, DNAs, genes, hormones, etc. Magnetic nanoparticles may also be added in the bone cement comprising powders, short fibers, or flakes, or fragmented mesh screens of $TiO_2$ if a remote, magnetically actuated release of therapeutic drugs or biological agents is desired.

Shown in FIG. 31 is an exemplary dental use of a cement comprising $TiO_2$-nanotube-coated powders, short fibers, or flakes, or fragmented mesh screens of $TiO_2$ (with optional Ti core) for accelerated dental bone growth. The formation of regenerated dental bone occurs in an accelerated manner on these loose templates of $TiO_2$ having nanotube or nanopore surface. For further accelerated kinetics of healthy dental bone growth, the powders, short fibers, or flakes, or fragmented pieces of mesh screen of $TiO_2$ can also be mixed with bone-growth nutrients, hydroxyapatite, natural bone powder, bio-degradable polymer, bio-compatible or bio-inert bone cement, bio-active glass, or optionally with biological agents of growth factors such as BMP (bone morphogenic protein) or collagen, or other biological agents such as antibiotics, therapeutic drugs, DNAs, genes, hormones, etc. Magnetic nanoparticles may also be added in the dental bone cement if a remote, magnetically actuated release of therapeutic drugs or biological agents is desired.

Figure 32:
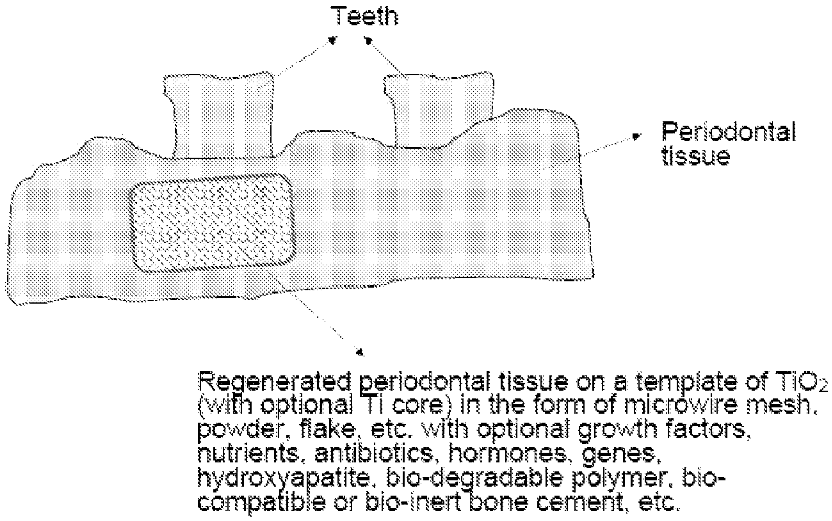
FIG. 32 schematically illustrates an exemplary periodontal use of $TiO_2$-nanotube-coated powders or mesh screen of $TiO_2$ (with optional Ti core) to accelerate the periodontal tissue growth and regenerative-healing process; and use of an exemplary product of this invention for regenerating periodontal tissue on a template of TiO2 (with optional Ti core) in the form of microwire mesh, powder, flake, etc. with optional growth factors, nutrients, antibiotics, hormones, genes, hydroxyapatite, bio-degradable polymer, bio-compatible or bio-inert bone cement, etc.

FIG. 32 schematically illustrates an exemplary periodontal use of the bone cement comprising loose $TiO_2$-nanotube-coated powders, flakes, short fibers, or fragmented mesh screen of $TiO_2$ (with optional Ti core) to accelerate the periodontal tissue growth and cure. For further accelerated kinetics of healthy growth of periodontal tissues, the powders, short fibers, or flakes, or fragmented pieces of mesh screen of $TiO_2$ can also be mixed with optional growth factors, nutrients, antibiotics, hormones, genes, hydroxyapatite, bio-degradable polymer, bio-compatible or bio-inert bone cement, etc.

This invention provides biomaterials comprising large-surface-area titanium oxide nanotubes, etc., alternative metals and alloys, fabrication methods, device application methods, and biomedical in-vivo or in-vitro applications for strongly adhered, and kinetically accelerated bone growth, periodontal cell growth, organ cell growth (liver, kidney, etc.), drug toxicity testing, cell detection, artificial organs, etc.

6. Optically Transparent or Translucent Cell-Culturing Substrate with Nano Imprint Patterned Nanostructure The invention provides optically transparent or translucent cell-culturing substrates with nano patterned surface nanostructures, for example, by nano-imprinting with stamps or nanoscale etching. The invention provides structures with the optical transparency needed by a cell culture, and this embodiment allows a microscopic examination of the cell behavior using inverted microscope with transmitted light illumination. In one aspect, a transparent cell culture substrate is nano-patterned or nano-etched first, the surface of which is then coated with an optically transparent or translucent, very thin film of Ti or Ti-base alloys (e.g., Ti—Al—V alloys), other refractory metals (e.g., Zr, Nb, Hf, Ta, W and their alloys with Ti, among themselves or with other alloying elements), or oxides such as $TiO_2$, $Nb_2O_5$, $ZrO_2$, $HfO_2$, $Ta_2O_5$, $W_2O_3$ or mixed alloy oxides, or nitrides. In one aspect, the desired thicknesses (or thinnesses) of the inorganic coatings (e.g., Ti or $TiO_2$ related alloys, oxides, etc) can be in a range of about 1 to 50 nm, or preferably in the range of about 1 to 20 nm.

In one aspect, the devices of the invention have optically transparent or translucent films; a metallic coating is generally opaque unless it is made "very thin" (which, in alternative embodiments, can be in the range from about 1 to 100 nm, 1 to 50 nm, or about 1 to 20 nm, or in alternative embodiments: at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 or more nm). In one aspect, the optically transparent or translucent cell-culturing substrate with nano patterned surface nanostructure comprise one or more of these selected inorganic coating materials (e.g., Ti or Ti-base alloys, e.g., Ti—Al—V alloys, other refractory metals, e.g., Zr, Nb, Hf, Ta, W and their alloys with Ti, among themselves or with other alloying elements, or oxides such as $TiO_2$, $Nb_2O_5$, $ZrO_2$, $HfO_2$, $Ta_2O_5$, $W_2O_3$ or mixed alloy oxides, or nitrides); this can allow biocompatible and cell-culture-enhancing substrate which allows microscopic examination with transmitted light.

The transparent substrate material to be surface nano-patterned and coated with a Ti, Ti oxide, Ti nitride or related inorganic film can be selected from transparent thermosetting polymer, transparent thermoplastic polymer, transparent UV-light-curable polymer, or transparent glass, and equivalent compounds. Exemplary thermosetting polymers that can be used in the manufacture of compositions of this invention include polydimethylsiloxane (PDMS), polymethyl methacrylate (PMMA), melamine, bakelite, or epoxy resins, and equivalent compounds. Exemplary thermoplastic polymers that can be used in the manufacture of compositions of this invention include polyethene, polypropene, polystyrene, or poly vinyl chloride, and equivalent compounds. Exemplary UV-light-curable polymers that can be used in the manufacture of compositions of this invention include polydimethylsiloxane (PDMS) or polymethyl methacrylate (PMMA), and equivalent polymers.

In alternative embodiments, the nano-patterned, see-through cell culture substrate with nano-patterned surface structure and coated with biocompatible, cell-culture-enhancing inorganic thin film, provides an optical transparency is at least 10%, 20%, 25%, 30%, 35%, 40%, or 50% or more, or alternatively at least about 40% of the light is sent through (passes through) the substrate.

Figure 33:
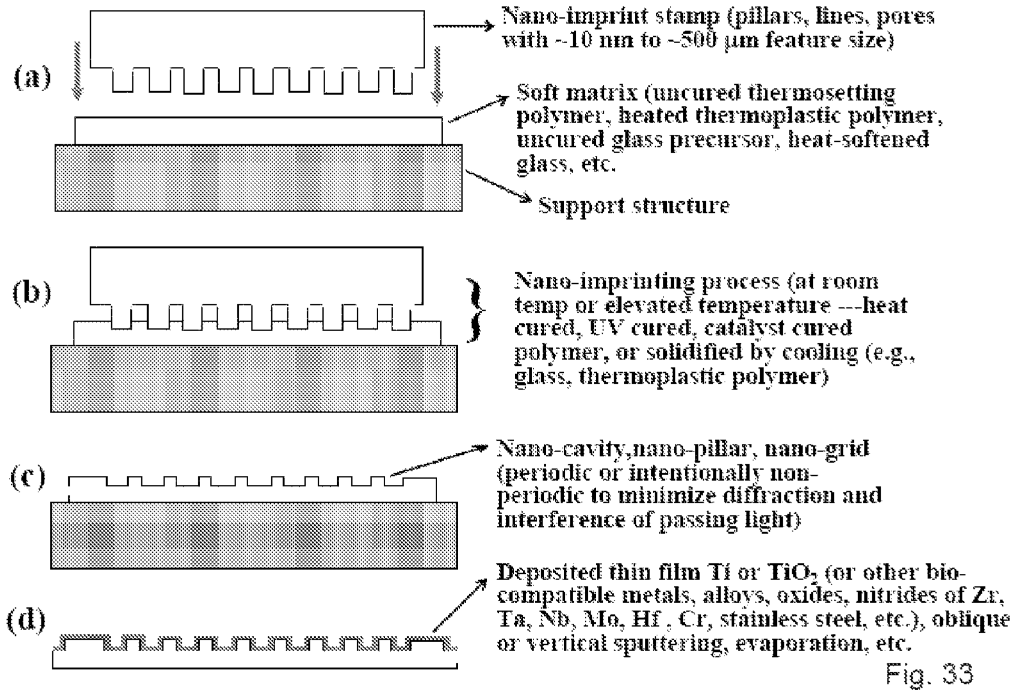
FIG. 33 schematically illustrates an exemplary nano or micro imprinting method to fabricate nano-patterned, completely or partially "see-through", or transparent, cell culture substrates of this invention based on plastic or glass, e.g., a culture dish or equivalent, which are coated with a thin layer of Ti, $TiO_2$ or related metals or oxides (including, e.g., a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic).
Figure 34:
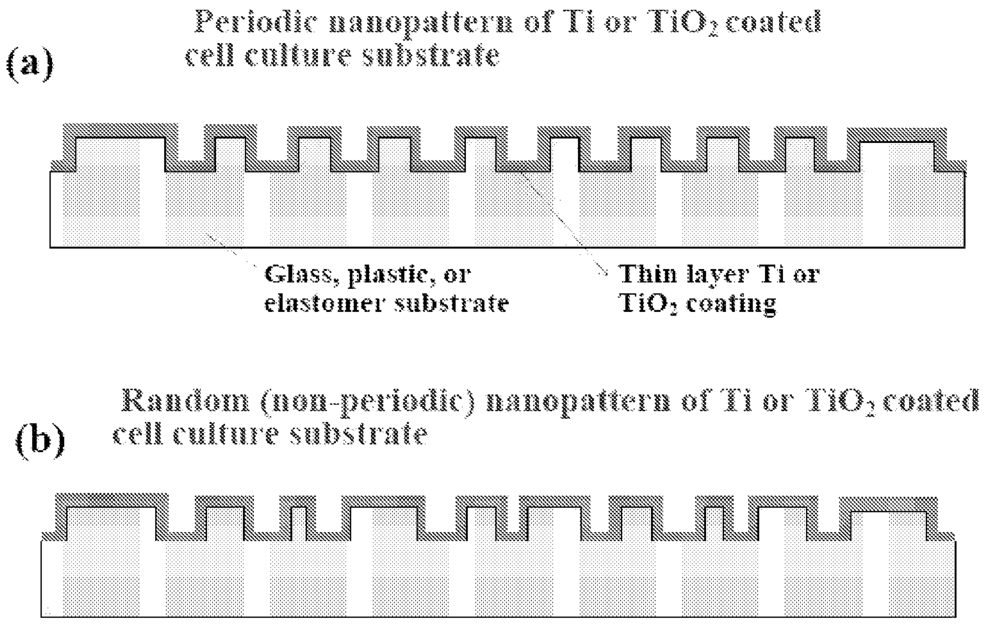
FIG. 34 compares two alternative nano-pattern embodiments of the invention, periodic versus (vs) random nano or micro imprinted patterns in a see-through cell culture substrate based on plastic or glass, coated with a thin layer of Ti, $TiO_2$ or related metals or oxides or nitrides (including, e.g., a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic).

Shown in FIG. 33 is an example method of fabricating such transparent or translucent cell-culturing substrate with nano imprinted patterned nanostructure. In this example, a nano or micro stamp made of silicon, metal or ceramic, e.g., fabricated by photolithography or electron-beam lithography process is utilized to impress into a soft matrix as illustrated in FIG. 33(*a*). Either an uncured thermosetting polymer, heated and softened thermoplastic polymer, uncured glass precursor, or heat-softened glass can be used as the substrate material to be imprinted. After imprinting (FIG. 33(*b*) and releasing FIG. 33(*c*)), the nano patterned substrate is coated by a very thin layer of Ti or Ti-base alloys, other refractory metals, oxides or nitrides as illustrated in FIG. 33(*d*). The coating of these inorganic material layer(s) on the surface-nano-patterned and transparent substrate (e.g., plastic, elastomeric polymer or glass) can be done by known methods such as sputtering, evaporation, atomic layer deposition, chemical vapor deposition, electroless plating or electroplating and other physical or chemical thin film deposition techniques. A good adhesion of the thin film coating on the transparent substrate surface is important. Ti, Ti-oxide or Ti-nitride coating and related refractory metals and compounds generally provide good adhesion onto substrate surface. The coating can be multi-laminar (multilayered) with one or a mixture of these compounds.

The nanopattern introduced by imprinting into the plastic, polymer or glass cell-culture substrate can be either periodic or random in its order aspect. While a periodic structure can be useful, sometimes a random structure is useful as this will minimize optical diffraction and other optical interferences, and hence make the cell-culture substrate material more transparent/translucent.

Figure 35:
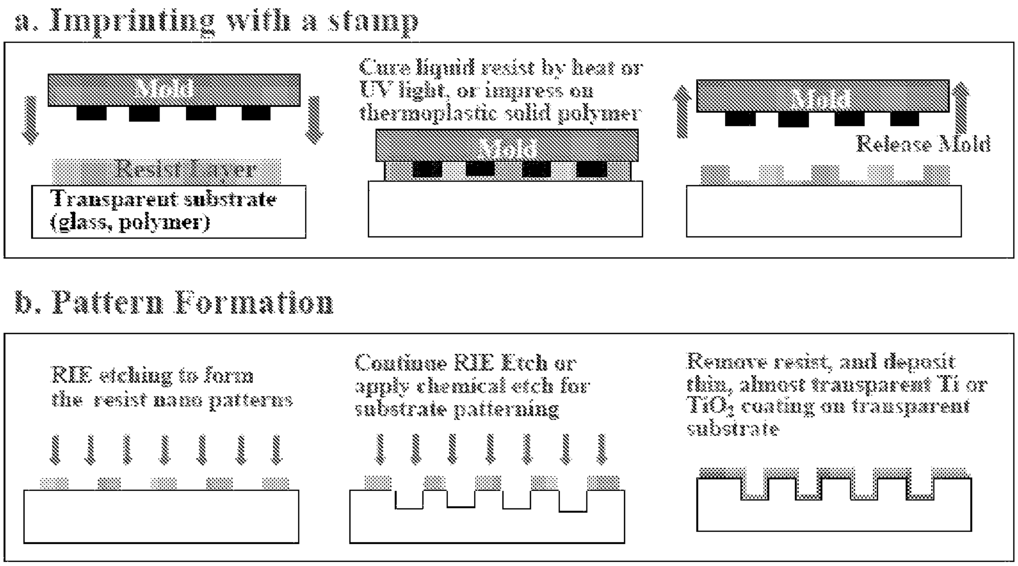
FIG. 35 schematically illustrates an alternative method of fabricating transparent or translucent cell-culture substrate by nano or micro imprinting plus chemical or reactive ion etched (RIE) etching method plus coating of a thin layer of Ti, $TiO_2$ or related metals or oxides or nitrides (including, e.g., a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic). This exemplary method comprises a nano imprint patterning of a mold onto a "resist layer" of a transparent substrate, to etch-pattern the transparent substrate (e.g., glass or polymer substrate) through the resist layer.

Shown schematically in FIG. 35 is a method for nano imprint patterning of a resist layer and etch-patterning the transparent glass or polymer substrate through the resist. Once a liquid resist layer (such as spin-coated or dip-coated) is cured by heat or UV light while being impressed, the layer can be reactive ion etched (RIE) to remove any residual material near the bottom of the impressed cavity so that the plastic or glass substrate is exposed and can now be etched by RIE or chemical etching for substrate patterning. The pattern can be either protruding or recessed, can be circular, oval, rectangular, or line array pattern. The resist layer can be then removed and a thin, almost transparent Ti or $TiO_2$ coating is deposited to obtain bio-compatible and cell-culture-enhancing transparent (or near transparent) substrates. The nano pattern can be made periodic or random, depending on the need for minimizing light diffraction and interference.

Figure 36:
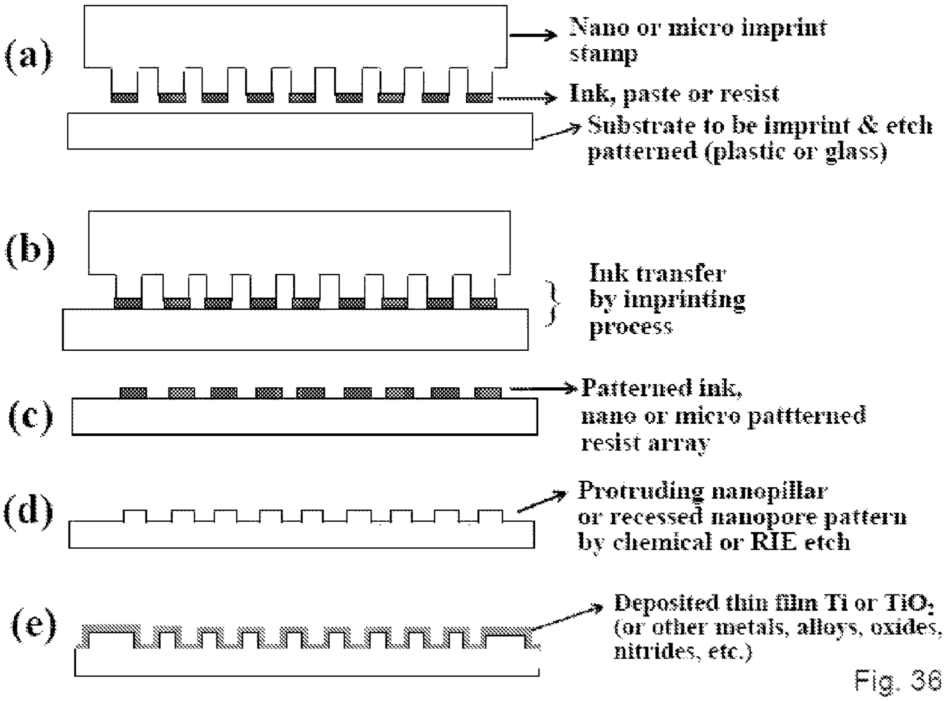
FIG. 36 illustrates an alternative method of fabricating transparent or translucent cell-culture substrate by nano or micro imprint based resist pattern transfer followed by chemical or RIE etching plus coating of a thin layer of Ti, $TiO_2$ or related metals or oxides or nitrides (including, e.g., a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic). In the embodiment of FIG. 36*a*, the resist pattern is made, or transferred, with an imprint stamp for patterning.

Shown in FIG. 36 is an alternative method of fabricating transparent or translucent cell-culture substrate by nano or micro imprint based resist pattern transfer followed by chemical or RIE etching, plus coating of a thin layer of Ti, $TiO_2$ or related metals or oxides. Nano or micro imprint stamp picks up ink or paste containing chemical-etch-resistant resist material and transfers onto the surface of a plastic or glass substrate to be imprint. Similarly as in FIG. 35, the pattern can be periodic or random, and can have either protruding or recessed, and can be circular, oval, rectangular, or line array pattern. The substrate is then chemical or RIE etched to form a pattern and a thin film of Ti or $TiO_2$ (or related metals, alloys, oxides, nitrides, etc.) is deposited to obtain bio-compatible and cell-culture-enhancing transparent (or near transparent) substrates.

Figure 37:
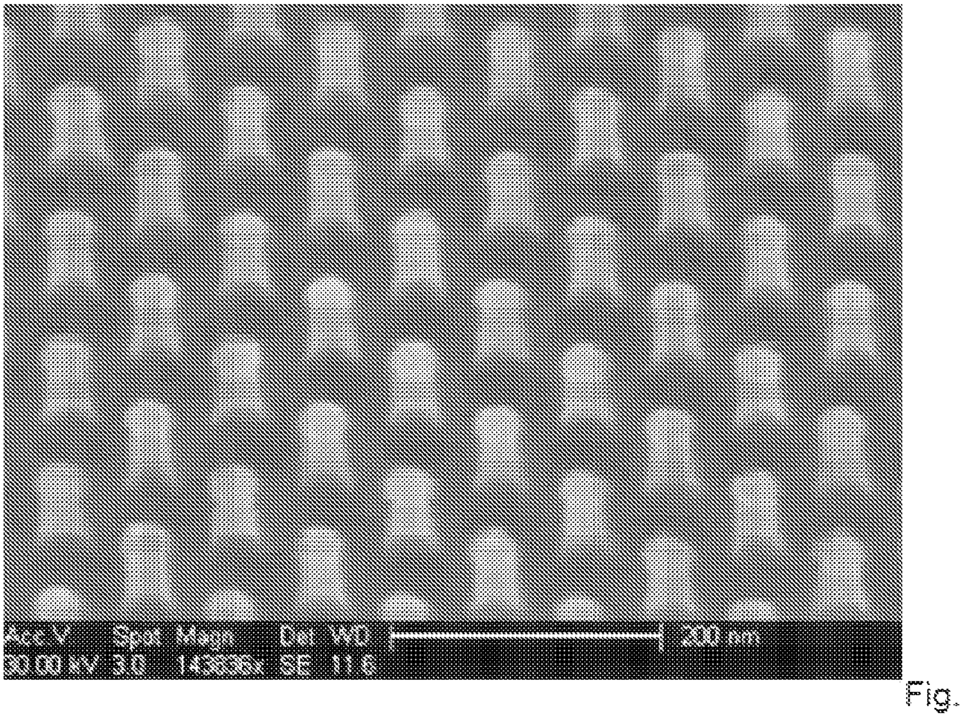
FIG. 37 illustrates a picture of an exemplary silicon nano imprint stamp containing 25 nm dia. periodic islands.

The nano or micro stamp for imprinting can be obtained by various patterned etch process, such as by electron beam lithography. FIG. 37 is an SEM micrograph showing an example silicon nano imprint stamp containing 25 nm diameter periodic pillar array, which is suitable for imprinting process to fabricate a patterned cell-culture-substrate as described in, e.g., FIGS. 33 to 36.

The invention provides biocompatible and cell-growth-enhancing culture substrate comprising elastically compliant protruding nanostructure substrate coated with Ti, $TiO_2$ or related metal and metal oxide films, as described herein. Exemplary nanostructure substrates of the invention can comprise a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic.

7. Biocompatible and Cell-Growth-Enhancing Culture Substrate Comprising Elastically Compliant Protruding Nanostructure Substrate Coated with Ti, $TiO_2$ or Related Metal and Metal Oxide Films The invention provides biocompatible and cell-growth-enhancing culture substrate comprising elastically compliant nanostructures coated with Ti, $TiO_2$ or related metal and metal oxide films, or in alternative embodiments, a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic material. The coating can be multi-laminar. The elastically compliant nanostructures of the invention ameliorate the stress or strain that the growing/propagating cells experience; the elastically compliant nanostructures have a beneficial effect on cell viability and growth behavior. By providing an elastically soft substrate, which is made even more flexible by virtue of protruding surface nanostructure, elastically compliant nanostructures of the invention can further enhance cell growth and viability.

Figure 38:
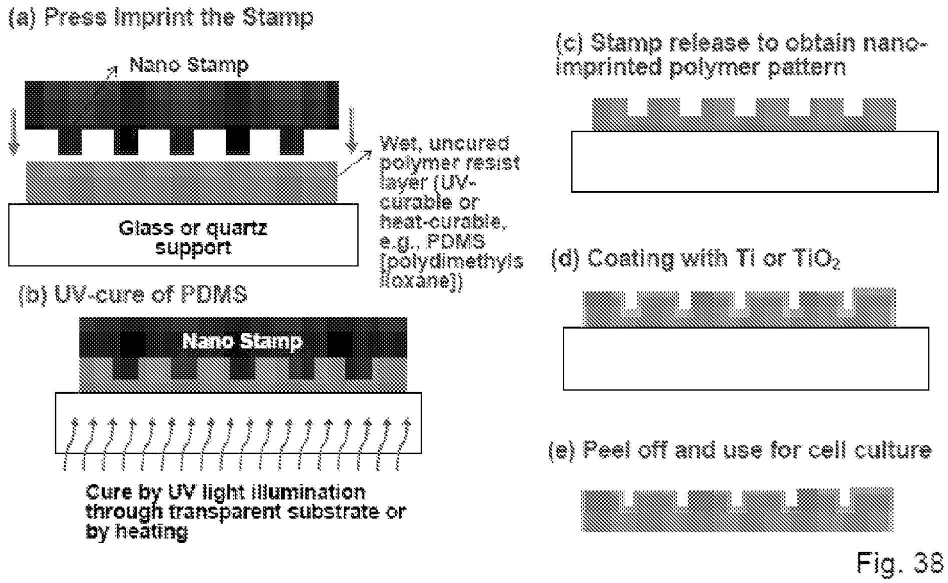
FIG. 38 is a schematic illustration of an exemplary polymer-based cell culture substrate of the invention cured while imprinted using UV light or heat, and coated with a thin layer of Ti or $TiO_2$, or a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic. This embodiment can alternative use from between about 20 nm to 20 μm feature nano stamps or micro stamps, which can be imprinted on spin-coated, uncured polymer, e.g., heat curable or UV light curable PDMS (polydimethylsiloxane), and cured while being imprinted.

The drawing shown as FIG. 38 represents a schematic illustration of an example method for fabricating elastomer-based cell culture substrate cured while imprinted using UV light or heat. The master pattern into which the elastomer is impressed into can be a recessed-cavity-pattern type so that the imprinted elastomer has protruding features; or alternatively, a recessed-pattern elastomer culture substrate is used. The pattern can be periodic or random, and can be circular, oval, rectangular, or line array pattern.

An exemplary method of making a biocompatible and cell-growth-enhancing culture substrate of this invention comprises an elastically compliant protruding nanostructure substrate coated with, e.g., Ti, $TiO_2$ or related metal and metal oxide films, and the methods comprises providing a surface nano-patterned stamp, impressing into a wet, uncured elastomer layer with the nanostamp, curing the polymer while being impressed by thermal curing or UV light curing, releasing and removing the stamp, and depositing a thin film of, e.g., Ti, Zr, Hf, Nb, Ta, Mo or W metal material, a Ti, Zr, Hf, Nb, Ta, Mo or W alloy, a Ti, Zr, Hf, Nb, Ta, Mo W oxide, or Ti, Zr, Hf, Nb, Ta, Mo or W nitride, or equivalent compounds, by a physical or chemical thin film deposition method.

In FIG. 38(*a*), the stamp is press imprinted to the wet, uncured polymer resist layer UV-curable or heat-curable elastomer, such as PDMS (polydimethylsiloxane). The PDMS layer is cured while being imprinted by UV light illumination through transparent substrate (from the bottom) or by heating (FIG. 38(*b*)). The stamp is then release to obtain nano-imprinted polymer pattern (FIG. 38(*c*)), and then is coated with Ti, $TiO_2$ or related bio-compatible surface coating (FIG. 38(*d*)). The cured, nanopatterned elastomer is then peeled off and used for cell culture (FIG. 38(*e*)), in-viro for cell culture supply or in-vivo as a part of an implant structure.

Figure 39:
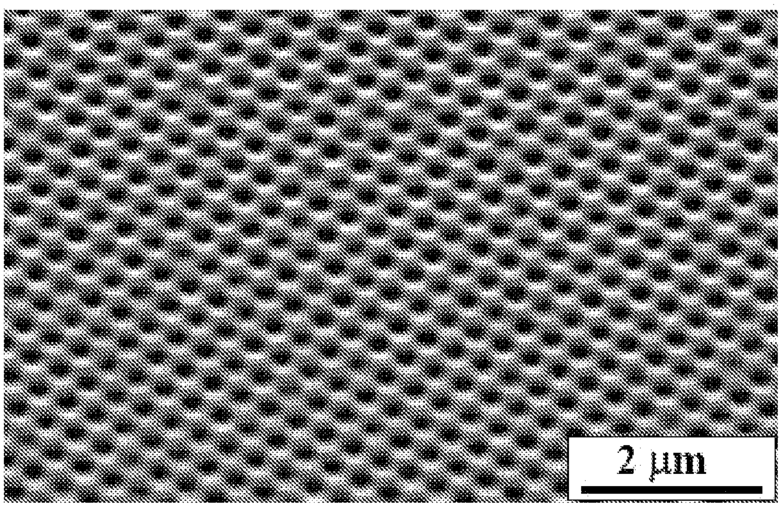
FIG. 39 illustrates a scanning electron microstructure of an exemplary nano-imprinted pattern on a PDMS (polydimethylsiloxane); this illustrates an exemplary nano-imprinted pattern on PDMS (Polydimethylsiloxane) at 200 nm diameter periodic pores, approximately 100 nm deep features.
Figure 40:
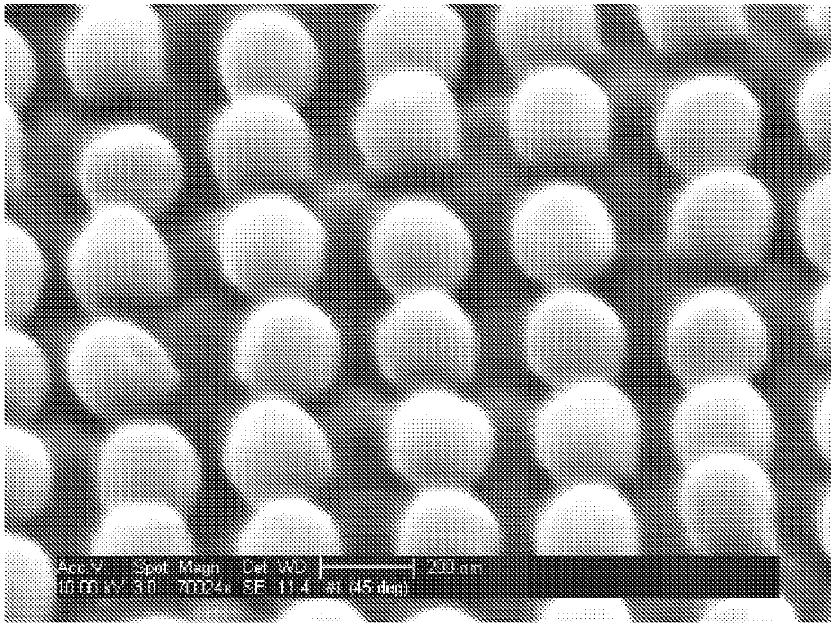
FIG. 40 illustrates an SEM micrograph showing an exemplary nano-patterned PDMS (polydimethylsiloxane) cell-culture substrate with protruding array of soft and compliant balls of ~200 nm diameter.

Shown in FIG. 39 is an example SEM (scanning electron microscopy) structure of nano-imprinted, recessed cavity array pattern on PDMS (polydimethylsiloxane) obtained by nano imprinting using a protruding-pillar-array metal stamp and UV light curing. FIG. 40 represents an SEM micrograph showing a nanopatterned PDMS (polydimethylsiloxane) cell-culture substrate with protruding array of soft and compliant balls of ~200 nm diameter, which was obtained by using a recessed-cavity-array silicon stamp and UV curing.

The various types of surface nanostructured or microstructured cell-culture or bone-culture substrates described in this invention can be used either for in vitro culture of cells and bones, or as a part of in vivo implant or drug or biological material delivery structure.

The types of cells or hard tissues that can be cultured in an enhanced manner by the substrates of this invention include osteoblast cells, periodontal cells, hepatocyte (or mixed cells for liver cell culture), kidney cells, blood vessel cells, skin cells, stem cells, endothelial cells and other rare cells, as well as rapid formation/growth of strongly adherent bones. The structures according to the invention can be useful for reliable and faster orthopedic or dental bone repair, for preparation of partial or full implant organs for in-vivo insertion, or ex-vivo operation as artificial lever or kidney, for externally controllable drug release and therapeutic treatments, for efficient toxicity testing of drugs and chemicals, and for diagnosis/detection of disease or forensic cells.

Alternative embodiments of the invention include:

1. Biomaterials with Strongly Bonded, Protruding Features

The macroscopically or microscopically extended biomaterial topography provides a lock-in mechanical integrity at the implant-hard tissue interface, while the $TiO_2$ nanotube type nano structure on the surface of the protrusion features and the surface of the base implant provides a desirable cell- or bone-growth-accelerating characteristics.

The invention provides various surface-protruding structures including hairy wire or mesh screen Ti protrusion structure with surface nanopore or nanotube $TiO_2$, particle- or fiber-aggregate protrusion structure, protrusion+implant base with re-entrant holes, fabrication techniques, method of bonding the protrusion structure to the base implant by diffusion bonding, melt-bonding, spot welding, and applications for mechanically locked-in, strongly adhered cell growth or bone growth, drug toxicity testing, artificial organs, dental or periodontal applications.

2. Externally and remotely controllable drug-delivery systems—In alternative embodiments, the nanotube or nanopore arrays, or micro-wires or micro-ribbon arrays on the implant surface are utilized as a reservoir for drug and other biological agents, with an advantageous characteristics of magnetically actuated, on-demand drug release capability. In alternative embodiments, the structures of the invention comprise various drug-reservoir nanopore structures+drugs/biological agents+optional magnetic nanoparticles. The invention provides remote controlled drug release mechanisms based on movement of magnetic particles versus high frequency (alternating current) AC magnetic field induced hyperthermia heating effect. The nanostructures include particle aggregate, mesoporous structure, nanowire or ribbon forest, directionally etched porous materials, and porous thin films with the incorporated drugs/biological agents+magnetic nanoparticles. Various fabrication/processing methods, and biomedical applications.

3. Elastically compliant implant material for bone growth—In alternative embodiments, the invention provides subdivided, spring-like fiber or mesh screen shape implants for stress-accommodation and minimal separation failures at the implant-hard tissue interface, which also provides strength and toughness reinforcement of the grown bone via bone-metal wire composite formation. The invention provides elastically compliant implant structures, fabrication methods, strong-interface bone growth applications.

4. Non-metallic or non-Ti based substrates the surfaces of which have been converted to $TiO_2$ type nanotubes or nanopores—In alternative embodiments, the invention provides products of manufacture comprising a thin film coating of Ti or $TiO_2$, or thin, a macro or a microscale coating comprising a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic, applied onto the surface(s) of already nanoporous material. In alternative embodiments, the term "thin" means having a thickness of at least about 1, 2, 3, 4, 5, 6, 7, 8, 9 or 10 or more nm, or having a thickness of between about 1 to 10 nm., or having a thickness of between about 1 to 15 nm., or having a thickness of between about 1 to 20 nm.

Alternatively, the invention provides products of manufacture comprising a thick film coating of Ti or $TiO_2$, or a "thick" film comprising a macro or a micro scale coating comprising a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic, deposited and anodized to create a nanotube, e.g., a $TiO_2$ nanotube type, to exhibit a desirable cell or bone growth accelerating characteristics. The invention provides porous or patterned substrates which have been made biocompatible and cell- or bone-growth-accelerating by $TiO_2$ surface nanotubes, etc., and various fabrication methods, and biomedical applications.

5. Biocompatible materials configured in loose particles, loose short-fibers, or loose flakes—The powder surfaces are processed to comprise nanopore or nanotube array nanostructure, so that the loose powders exhibit cell- or bone-growth-accelerating characteristics, which is useful for bone cement and other tissue connection applications. Claims to be incorporated—Various types of fabrication methods for $TiO_2$ surface nanotubes on loose powders, short-fibers, flakes, fragmented mesh screens. Also, the invention provides various application methods, and biomedical applications including accelerated bone growth, dental bone growth, periodontal tissue growth.

It should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed:

1. A product of manufacture comprising:

(a) a biocompatible surface;

(b) a plurality of macro or microscale structures fixed or loosely placed on the biocompatible surface, wherein the plurality of macro or microscale structures comprise:

(i) a plurality of hairy-shaped or gauze shaped, mesh or mesh screen, wire, woven wire, spring, ribbon, powder, or flake shaped macro or microscale structures, wherein the macro or a microscale structure comprises a Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic;

(ii) a plurality of macro or microscale loose, short-fibers, or flake shaped structures, or macro or microscale particles, or macro or microscale spring-like fibers, made of a material comprising Ti, Zr, Hf, Nb, Ta, Mo and/or W metal material, a Ti, Zr, Hf, Nb, Ta, Mo and/or W alloy, a Ti, Zr, Hf, Nb, Ta, Mo and/or W oxide or nitride, and/or stainless steel or ceramic;

(iii) a plurality of macro or microscale micro-wires, micro-fibers or micro-ribbons;

(iv) a plurality of macro or microscale spring-like fibers or mesh screen shapes comprising a Ti or metal material, an alloy and/or a ceramic;

or (v) any combination of the structures of (i) to (vi); and (c) a plurality of nanostructures on the surfaces of the plurality of macro or microscale structures, wherein the nanostructures comprise:

(i) a biocompatible vertically aligned nanotube array structure;

(ii) a lock-in nanostructure comprising a plurality of nanopores or nanotubes, wherein the nanopore or nanotube entrance has a smaller diameter or size than the rest (the interior) of the nanopore or nanotube to exhibit a re-entrant configuration;

(iii) a dual structured biomaterial comprising (A) micro- or macro-pores, wherein the micro or macro pores has an average diameter, or equivalent diameter if the pores are not circular, in the range of between about 0.5-1,000 μm, or between about 1-100 μm; and, (B) a surface area covered with nanotubes;

(iv) a plurality of enlarged diameter nanopores and/or nanotubes, wherein the nanopores and/or nanotubes comprise at least 150 nm; or (v) any combination of (i) to (iv)

wherein the nanotube structures of any of (c)(i) to (c)(iv) have a thickness of at least about 0.5, or between about 1 and 50 nm, or between about 1 and 100 nm, or between about 10 nm to 500 nm, wherein at least a portion of, or substantially all of, or all of, the surface of the macro or microscale structures of (b) are covered or coated by one or a plurality of nanostructures structures of (c).

2. The product of manufacture of claim 1:

wherein a macro or microscale members and/or a nanotube array structure, or a structure of any of (b) or (c) comprises a Ti, Zr, Hf, Nb, Ta, Mo and/or W metal; a Ti, Zr, Hf, Nb, Ta, Mo and/or W alloy; and/or, a Ti, Zr, Hf, Nb, Ta, Mo and/or W oxide or nitride, and/or stainless steel or ceramic.

3. The product of manufacture of claim 1, wherein the plurality of nanostructures comprise elastically compliant nanostructures.

4. The product of manufacture of claim 1, wherein the product of manufacture is an optically transparent or translucent cell-culturing substrate.

5. The product of manufacture of claim 1, wherein the plurality of nanostructures are nano imprint patterned nanostructures.

6. The product of manufacture of claim 1, wherein the biocompatible surface is a particle aggregate or a mesoporous structure.

7. The product of manufacture of claim 1, wherein the plurality of macro or microscale structures are shaped or manufactured as a nanowire or ribbon forest.

8. The product of manufacture of claim 1, wherein the plurality of nanostructures partially or completely coating the macro or microscale surfaces have a thickness of at least about 1, 2, 3, 4, 5, 6, 7, 8, 9 or 10 or more nm, or a thickness of between about 1 to 20 nm.

9. The product of manufacture of claim 1, wherein the product of manufacture is an orthopaedic (orthopedic) implant or a dental implant.

10. The product of manufacture of claim 1, further comprising:

a bone cell, a liver cell, a kidney cell, a blood vessel cell, a skin cell, a periodontal cell or a periodontal tissue cell, a stem cell, an organ cell, or wherein the cell is a bone cell, a liver cell, a kidney cell, a blood vessel cell, a skin cell, an organ cell.

11. The product of manufacture of claim 1, wherein the macro or microscale members have a diameter and depth in the size range of between about 10 to 5000 micrometers.

12. The product of manufacture of claim 1, wherein at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or all, of the biocompatible surface comprises or is covered or coated by a plurality of macro or microscale structures of 1(b).

13. The product of manufacture of claim 1, wherein the biocompatible surface comprises a matrix material comprising:

(1) a Ti, Zr, Hf, Nb, Ta, Mo and/or W metal;

(2) an oxide of (1), or (3) an alloy of (1);

or a structure of any of (b)(i) to (b) (vii) comprises:

(1) a Ti, Zr, Hf, Nb, Ta, Mo and/or W metal;

(2) an oxide of (1); or (3) an alloy of (1).

14. The product of manufacture of claim 1, wherein the biocompatible surface comprises:

a Si, a Si oxide, an Al, an Al oxide, a carbon, a diamond, a noble metal, an Au, an Ag, a Pt and/or an Al, Au, an Ag, a Pt alloy, a polymer or a plastic material, a composite metal, a ceramic, a polymer and/or a combination thereof.

15. The product of manufacture of claim 1, wherein the vertically aligned nanotube array structures comprise or are manufactured as a laterally separated nanotube arrangement.

16. The product of manufacture of claim 1, further comprising a plurality of cells, wherein the plurality of cells comprise a human or an animal cell.

17. The product of manufacture of claim 16, wherein the plurality of human or animal cells are bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof.

18. The product of manufacture of claim 1, further comprising a hydroxyapatite or a bio-degradable polymer.

19. The product of manufacture of claim 1, further comprising a bio-compatible or bio-inert bone cement.

20. The product of manufacture of claim 1, further comprising a biological agent, a growth factor, a collagen, a nucleic acid, an antibiotic, a hormone, a drug, a magnetic particle, a metallic particle, a ceramic particle, a polymer particle, or a drug delivery particle.

21. The product of manufacture of claim 1, wherein the macro or microscale fibers or particles are straight, curved and/or bent.

22. The product of manufacture of claim 1, wherein the macro or microscale spring or spring-like fibers, or macro or microscale mesh or mesh screen members, are fixed or loosely placed, or elastically compliant, or a combination thereof, on the biocompatible surface.

23. The product of manufacture of claim 1, wherein the macro or microscale wires, ribbons or fibers are straight, curved and/or bent.

24. The product of manufacture of claim 1, wherein the macro or microscale micro-wires, micro-fibers or micro-ribbons are fixed or loosely placed, or elastically compliant, or a combination thereof, on the biocompatible surface.

25. The product of manufacture of claim 1, wherein for the plurality of enlarged diameter nanopores and/or nanotubes of (c)(iv), the nanopores and/or nanotubes comprise at least about 200 nm, or at least about 400 nm.

26. The product of manufacture of claim 16, wherein the plurality of cells are suitable for implantation and regeneration of an organ or a dental tissue in a subject.

27. The product of manufacture of claim 16, wherein the plurality of cells are suitable for implantation and regeneration of a bone and/or a joint tissue in a subject.

28. The product of manufacture of claim 1, further comprising one or more biologically active agents selected from the group consisting of therapeutic drugs, growth factors, proteins, enzymes, hormones, nucleic acids, RNA, DNA, genes, vectors, antibiotics or antibodies, small molecules, radioisotopes and magnetic nanoparticles.

29. The product of manufacture of claim 1, wherein the nanotube structures of any of b(i) to b(ix) have a thickness of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nm.

30. The product of manufacture of claim 1, wherein the plurality of nanotube structures have an average diameter in the range of between about 20 to 500 nm.

31. The product of manufacture of claim 8, wherein the plurality of nanostructures partially or completely coating the biocompatible surface and have a thickness of at least about 1 to 10 nm, or a thickness of between about 1 to 15 nm.

32. The product of manufacture of claim 11, wherein the plurality of nanostructures have a thickness of at least about 1 to 10 nm, or a thickness of between about 1 to 15 nm.

33. The product of manufacture of claim 1, wherein substantially all of the macro or microscale structures of (b) are covered or coated by one or a plurality of nanostructure structures of (c).

34. The product of manufacture of claim 33, wherein the plurality of nanostructures of (c) are nanotubes.

* * * * *